United States Patent [19]
Suominen et al.

[11] Patent Number: 5,837,515
[45] Date of Patent: Nov. 17, 1998

[54] ENZYME PREPARATIONS AND METHODS FOR THEIR PRODUCTION

[75] Inventors: Pirkko Suominen, Helsinki, Finland; Helena Nevalainen, North Epping, Australia; Ritva Saarelainen; Marja Paloheimo, both of Helsinki, Finland; Richard Fagerström, Espoo, Finland

[73] Assignee: Alko-Yhtiöt Oy, Helsinki, Finland

[21] Appl. No.: 121,436

[22] Filed: Sep. 16, 1993

Related U.S. Application Data

[63] Continuation-in-part of Ser. No. 78,478, which is a continuation-in-part of PCT/FI93/00221, May 24, 1993, abandoned, which is a continuation-in-part of Ser. No. 889,893, May 29, 1992, abandoned, which is a continuation-in-part of Ser. No. 524,308, May 16, 1990, Pat. No. 5,298,405.

[51] Int. Cl.$^6$ .............................. C12N 1/21; C12N 9/24; C12N 15/56; C12N 15/63
[52] U.S. Cl. ................. 435/200; 435/252.3; 435/254.11; 435/254.6; 435/320.1; 435/325; 536/23.2; 536/23.74
[58] Field of Search ............................. 536/23.74, 23.2; 435/320.1, 252.3, 240.2, 254.6, 254.1, 200, 254.11, 325

[56] References Cited

U.S. PATENT DOCUMENTS

| | | | |
|---|---|---|---|
| 5,202,249 | 4/1993 | Kluepfel et al. | 435/201 |
| 5,358,864 | 10/1994 | van den Broeck et al. | 435/209 |
| 5,610,046 | 3/1997 | van Ooyen et al. | 435/200 |
| 5,610,048 | 3/1997 | Schülein et al. | 435/209 |

FOREIGN PATENT DOCUMENTS

| | | |
|---|---|---|
| 0 244 234 | 11/1987 | European Pat. Off. . |
| 0 262 040 | 3/1988 | European Pat. Off. . |
| 0 33 4739 | 9/1989 | European Pat. Off. . |
| 0 334 739 | 9/1989 | European Pat. Off. . |
| 0 351 655 | 1/1990 | European Pat. Off. . |
| 0 383 999 | 8/1990 | European Pat. Off. . |
| 0 386 888 | 9/1990 | European Pat. Off. . |
| 0 395 792 | 11/1990 | European Pat. Off. . |
| 0 463 706 | 1/1992 | European Pat. Off. . |
| WO 89/08738 | 9/1989 | WIPO . |
| WO 91/02791 | 3/1991 | WIPO . |
| WO 91/05908 | 5/1991 | WIPO . |
| WO 91/19782 | 12/1991 | WIPO . |
| WO 92/03541 | 3/1992 | WIPO . |
| WO 92/06209 | 4/1992 | WIPO . |

OTHER PUBLICATIONS

Dekker, R.H., in Hignehi, T., ed., Biosynthesis and Biodegradation of Wood Components (Academic Press, Inc., Orlando, FL, pp. 505–533 (1985).

Paloheimo, M. et al., Production of Xylanase by *Trichoderma Reesei*, First European Conference on Fungal Genetics, Nottingham, UK; Aug. 20–23, 1992.

Saarelainen, R., et al., "Cloning and Expression of the Xylanase Genes in *Trichoderma Reesei*," 9th Intl. Biotechnol. Symp., Aug. 16–21, 1992, Crystal City, Virginia.

Shareck, F. et al., "Sequences of three genes specifying xylanases in *Streptomyces Lividans*," *Gene* 107:75–82 (1991).

Viikari, L., et al., Bleaching with Enzymes The Third Intl. Conference on Biotechnology in the Pulp and Paper Industry, Stockholm, Sweden, Jun. 16–19, 1986, pp. 67–69.

Viikari, L., et al., Fourth Intl. Symp. Wood and Pulping Chemistry, Paris, France Apr. 27–30, 1987; vol. 1, pp. 151–154.

Woodward, J. et al., "Xylanases: Functions, Properties and Applications," In: Topics in Enzyme and Fermentation, *Biotechnol.* 8:9–30 (1984).

Baker, C.J. et al., Xylanase from Trichoderma pseudokoningii: Purification, Characterization, and Effects on Isolated Plant Cell Walls, *Phytopathology* 67:1250–1258 (Oct. 1977).

Bastawde, K.B., Xylan structure, microbial xylanases, and their mode of action, *World J. Microbiol. and Biotechnol.* 8:353–368 (1992).

Biely, P., Artificial substrates for cellulolytic glycanases and their use for the differentiation of *Trichoderma* enzymes, in Kubicek, C.P. et al., eds., *Trichoderma reesei Cellulases: Biochem., Genet., Physiol. and Appl.*, Proceedings of a Symposium, Technical Univ. of Vienna, Sep. 14–16/89, Royal Soc. of Chem., pp. 30–46 (1990).

Boucher, F. et al., Complete nucleotide sequence of the xylanase gene from the yeast *Cryptococcus albidus*, *Nucleic Acids Research* 16(20):9874 (1988).

Dekker, R.F.H. et al., Hemicellulases: Their Occurrence, Purification, Properties And Mode Of Action, *Adv. Carbohydrate Chem. Biochem.* 32:277–352 (1976).

Durand, H. et al., A Genetic Approach Of The Improvement Of Cellulase Production By *Trichoderma reesei*, in Egneuse, H. et al., eds., *Proceedings of BioEnergy World Conference*, vol. 3, Elsevier Applied Sciences Publishers, London, pp. 246–253 (1984).

Fukusaki, E. et al., The complete nucleotide sequence of the xylanase gene (*xynA*) of *Bacillus pumilus*, *FEBS Letters 171* (2):197–201 (Jun. 1984).

Ghangas, G.S. et al., Cloning of a *Thermomonospora fusca* Xylanase Gene and Its Expression in *Esherichia coli* and *Streptomyces lividans*, *J. Bacteriol.* 171 (6): 2963–2969 (Jun. 1989).

(List continued on next page.)

*Primary Examiner*—Eric Grimes
*Attorney, Agent, or Firm*—Sterne, Kessler, Goldstein & Fox P.L.L.C.

[57] ABSTRACT

The structure of the *T. reesei* xln1 and xln2 genes and the primaru structure of proteins are described. Enzyme preparations enriched in hemicellulase enzymes are described. Such enzyme preparations may also be partially or completely deficient in cellulose degrading activity. Such preparations may be utilized in an crude, unpurified form and are especially useful in the production of pulp and paper.

37 Claims, 21 Drawing Sheets

OTHER PUBLICATIONS

Harkki, A. et al., Genetic engineering of *Trichoderma* to produce strains with novel cellulase profiles, *Enzyme Microb. Technol.* 13:227–233 (Mar. 1991).

Henrissat, B., Analysis of hemicellulases sequences. Relationships to other glycanases, in Visser, J. et al., eds., *Xyland and Xylanases,* Elsevier Science Publishers, pp. 97–110 (1992).

Henrissat, B. et al., Cellulase families revealed by hydrophobic cluster analysis, *Gene* 81:83–95 (1989).

Hrmová, M. et al., Specificity of cellulase and β-xylanase induction in *Trichoderma reesei* QM 9414, *Arch. Microbiol.* 144:307–311 (1986).

Ito, K. et al., Cloning and Sequencing of the *xynA* Gene Encoding Xylanase A of *Aspergillus kawachii, Biosci. Biotech. Biochem.* 56(6):906–912 (1992).

John, M. et al., Xylanases and β–Xylosidase of *Trichoderma lignorum, Methods in Enzymol.* 160:662–671 (1988).

Kantelinen, A., Enzymes in bleaching of kraft pulp, Dissertation for the degree of Doctor of Technology Helsinki University of Technology, Espoo, Finland, VTT Publications 114 (Oct. 1992).

Katsube, Y. et al., Estimation of Xylanase Active Site From Crystalline Structure, in *Proceedings of the 2nd International Conference on Protein Engineering,* Japan Scientific Societies Press, Tokyo, pp. 91–96 (1990).

Kubicek, C.P. et al., Interrelationships And Differences In The Regulation Of Xylanase And Cellulase Formation By *Trichoderma Reesei,* Presented May 30, 1992 at the Fifth International Conference on Biotechnology in the Pulp and Paper Industry, Kyoto, Japan (May 27–30 1992).

Lahtinen, T. et al., Using Selective *Trichoderma* Enzyme Preparations In Kraft Pulp Bleaching, Presented at the Fifth International Conference on Biotechnology in the Pukp and Paper Industry, Kyoto, Japan (May 27–30, 1992).

Lahtinen, T. et al., Using Selective *Trichoderma* Enzyme Preparations In Kraft Pulp Bleaching, Text of a lecture presented May 28, 1992 at the Fifth International Conference on Biotechnology in the Pulp and Paper Industry, Kyoto, Japan (May 27–30, 1992).

Lahtinen, T. et al., Using Selective *Trichoderma* Enzyme Preparations in Kraft Pulp Bleaching, *Proceedings of the Fifth International Conference on Biotechnology in the Pulp and Paper Industry,* Kyoto, Japan, pp. 128–137 (May 27–30 1992).

Lappalainen, A., Purification and Characterization of Xylanolytic Enzymes from *Trichoderma reesei, Biotechnol. Appl. Biochem.* 8:437–448 (1986).

Lin, L. et al., Cloning, sequencing and expression of a gene encoding a 73 kDa xylanase enzyme from the rumen anaerobe *Butyrivibrio fibrisolvens* H17c, *Mol. Gen. Genet.* 228:55–61 (1991).

Maat, J. et al., Xylanases and their application in bakery, in Visser, J. et al., *Xylans and Xylanases,* Elsevier Science Publishers, pp. 349–360 (1992).

Merivuori, H. et al., Different Temperature Profiles of Enzyme Secretion By Two Common Strains Of *Trichoderma reesei, Biotechnology Letters* 12 (2):117–120 (1990).

Nevalainen, H. et al., The Molecular Biology Of *Trichoderma* And Its Application To The Expression Of Both Homologous And Heterologous Genes, in Leong et al., eds., *Mol. Indust. Mycology: Systems and Applications for Filamentous Fungi,* Marcel Dekker, Inc., New York, pp. 129–148 (1990).

Nevalainen, H., Genetic improvement of enzyme production in industrially important fungal strains, Presented in the Department of Genetics, University of Helsinki, Espoo, Finland, Publication No. 26 (Nov. 29, 1985).

Nitisinprasert, S., Characterization of the cellulolytic enzyme systems of the anaerobic bacterium CM126 and the filamentous fungus *Trichoderma reesei,* Academic Dissertation in Microbiology, Department of Microbiology, University of Helsinki, Helsinki, Finland (Nov. 30, 1990).

Oku, T. et al., Amino Acid Sequence And Proposed Catalytic Residues Of Xylanase A From *Schizophillum Commune, Canadian Fed. Biol. Soc. Annu. Meeting,* p. 184, Abstract No. 676 (1988).

Paice, M.G. et al., A xylanase gene from *Bacillus subtilis:* nucleotide sequence and comparison with *B. pumilus* gene, *Arch. Microbiol.* 144:201–206 (1986).

Paloheimo, M. et al., Enzyme Production by *Trichoderma reesei* using the *cbhI* promoter, in Suominen, P. et al., eds., *Trichoderma reesei Cellulases and Other Hydrolases,* Foundation for Biotechnical and Industrial Fermentation Research, vol. 8, Proceedings of the TRICEL93 Symposium, Espoo, Finland, pp. 229–239 (Jun. 2–5, 1993).

Poutanen, K., Characterization of xylanolytic enzymes for potential applications, Dissertation of the degree of Doctor of Technology, Helsinki University of Technology, Espoo, Finland, Technical Research Centre of Finland, Publication No. 47 (Apr. 1988).

Poutanen, L. et al., Evaluation of different microbial xylanolytic systems, *J. Biotechnol.* 6:49–60 (1987).

Program from the Fifth International Conference on Biotechnology in the Pulp and Paper Industry, Kyoto International Community House, Kyoto, Japan, May 27–30, 1992.

Scheirlinck, T. et al., Cloning and expression of cellulase and xylanase genes in *Lactobacillus plantarum, Applied Microbiol. Biotechnol.* 33:534–541 (1990).

Senior, D.J. et al., Production and application of xylanases from *Trichoderma harzianum,* in Kubicek, C.P. et al., eds., *Trichoderma reesei Cellulases: Biochemistry, Genetics, Physiology and Application,* Proceedings of a Symposium held at the Technical University of Vienna, Sep. 14–16, 1989, Royal Society of Chemistry.

Shareck, F. et al., Sequences of three genes specifying xylanases in *Streptomyces lividans, Gene* 107:75–82 (1991).

Sinner, V.M. et al., Enzymatische Hydrolyse von Laubholzxylanen, *Holzforschung* 29:207–214 (1975).

Suominen, P. et al., Genetic Engineering Of *Trichoderma longibrachiatum* To Produce Suitable Enzyme Combinations For Different Application In The Pulp And Paper Industry, Abstract presented May 30, 1992 at the Fifth International Conference on Biotechnology in the Pulp and Paper Industry, Kyoto, Japan (May 27–30, 1992).

Suominen, P. et al., Genetic Engineering of *Trichoderma reesei* to Produce Suitable Enzyme Combinations for Applications in the Pulp and Paper Industry, *Proceedings of the Fifth International Conference on Biotechnology in the Pulp and Paper Industry,* Kyoto, Japan, pp. 439–445 (May 27–30, 1992).

Tan, L.U.L. et al., Purification and characterization of two D–xylanases from *Trichoderma harzianum, Enzyme Microb. Technol.* 7;425–430 (1985).

Tenkanen, M. et al., Two major xylanases of *Trichoderma reesei, Enzyme Microb. Tehcnol.* 14:566–574 (1992).

Törrönen, A. et al., The Two Major Xylanases From *Trichoderma reesei*: Characterization Of Both Enzymes And Genes, *Bio/Technology* 10:1461–1465 (Nov. 1992).

Van Doorslaer, E. et al., Hydrolysis of β–D–xylo–oligosaccharides by β–D–xylosidase from *Bacillus pumilus, Carbohydrate Research 140*:342–346 (1985).

Viet, D.N. et al., Purification and Properties of β–1,4–Xylanase from *Aeromonas caviae* W–61, *Appl. Environ. Microbiol. 57*(2):445–449 (Feb. 1991).

Viikari, L. et al., Hemicellulases for Industrial Applications, in Saddler, J., ed., *Bioconversion of Forest and Agricultural Wastes,* CAB International, USA, pp. 131–182 (1993).

Viikari,L. et al., Important Properties of Xylanases for Use in the Pulp and Paper Industry, in Kuwahara, M. et al., eds., *Biotechnology in Pulp and Paper Industry,* Proceedings of the Fifth International Conference on Biotechnology in the Pulp and Paper Industry, Uni Publishers Co., Ltd., Tokyo, pp. 101–106 (1992).

Viikari, L. et al., Xylanase enzymes promote pulp bleaching, *Paper and Timber 73*:384–389 (1991).

Wakarchuk, W. et al., The 20 KD Xylanase of *Bacillus subtilis:* A Structure/Function Analysis, in Visser, J. et al., eds., *Xylans and Xylanases,* Elsevier Science Publishers, pp. 439–442 (1992).

Whitehead, T. R. et al., Cloning and Comparison of Xylanase Genes from Ruminal Clonic *Bacteroides* Species, *Current Microbiol. 23*:15–19 (1991).

Wood, T.M. et al., Studies Of Two Low–Molecular–Weight Endo–(1→4)–β–D–Xylanases Constitutively Synthesized By The Cellulolytic Fungus *Trichoderma koningii, Carbohydrate Research 148*:321–330 (1986).

Yaguchi, M. et al., Amino Acid Sequence of the Low–Molecular–Weight Xylanase from *Trichoderma viride,* Symposium lecture given at "The Xylans and Xylanases Symposium," Wageningen, Holland, Dec. 8–11, 1991.

Yaguchi, M. et al., Amino Acid Sequence of the Low–Molecular–Weight Xylanase from *Trichoderma viride,* in Visser, J. et al., eds., *Xylans and Xylanases,* Elsevier Science Publishers, pp. 149–154 (1992).

Yaguchi, M. et al., The Amino Acid Sequence of the 20 KD Xylanase from *Trichoderma harzianum* E58, in Visser, J. et al., eds., *Xylans and Xylanases,* Elsevier Science Publishers, pp. 435–438 (1992).

Yang, R.C.A. et al., Nucleotide sequence of a *Bacillus circulans* xylanase gene, *Nucleic Acids Research 16*(*14*):7187 (1988).

Zappe, H. et al., Nucleotide sequence of a Clostridium *acetobutylicum* P262 xylanase gene (*xynB*), *Nucleic Acids Research 18*(*8*):2179 (1990).

Dialog file 350/351 Abstract of EP 262040 (1988), Accession No. 88–086285/13.

Dialog file 350/351 Abstract of EP 334739 (1989), Accession No. 89–280054/39.

Kantelinen, A. et al., an English translation of "Entsyymelläkö erron Kloorista?" *Kemia–Kemi 15*:228–231 (1988).

Nevalainen, H. et al., "*Trichoderma reesei* as a Production Organism for Enzymes for the Pulp and Paper Industry," Chapter 60 in: Biotechnology in Pulp and Paper Manufacture, Applications and Fundamental Investigations, T.K. Kirk et al., eds., Butterworth–Heinimann, Boston, pp. 593–599, (1990) Text of a lecture presented at 4th Int. Conf. on Biotechnol. in the Pulp and Paper Industry, Raleigh, N.C., USA, May 16–19, 1989.

Penttilä, M. et al., "The Molecular Biology of *Trichoderma reesei* and its Application to Biotechnology," *Appl. Molecular Genetics of Fungi: Symp. of Brit. Mycol. Soc.,* held Apr. 1990, J.F. Peberdy et al., eds., Ch. 5, pp. 85–102, Cambridge Univ. Press (1991).

xylanase II genomic sequence

```
aagcttgatgaggccaaattatccgtcaactgtcttatgaaggagcccatgccaa      -121 accccccctaaagactcaagaagccaaacctgaacaaccccagcacctgaacagtcatac  -61 aaccctccaagcccaaaagacacaacaactcctactagctgaagcaagaagacatcaac   -1

ATGGTCTCCTTCACCTCCCTCCTCGCCGGCGTCGCCGCCATCTCGGGCGTCTTGGCCGCT  60
MetValSerPheThrSerLeuLeuAlaGlyValAlaAlaIleSerGlyValLeuAlaAla

CCCGCCGCCGAGGTCGAATCCGTGGCTGTGGAGAAGCGCCAGACGATTCAGCCCGGCACG  120
ProAlaAlaGluValGluSerValAlaValGluLysArgGlnThrIleGlnProGlyThr

GGCTACAACAACGGCTACTTCTACTCGTACTGGAACGATGGCCACGGCGGCGTGACGTAC  180
GlyTyrAsnAsnGlyTyrPheTyrSerTyrTrpAsnAspGlyHisGlyGlyValThrTyr

ACCAATGGTCCCGGCGGGCAGTTCTCCGTCAACTGGTCCAACTCGGGCAACTTTGTCGGC  240
ThrAsnGlyProGlyGlyGlnPheSerValAsnTrpSerAsnSerGlyAsnPheValGly

GGCAAGGGATGGCAGCCCGGGACCAAGAACAAGtaagactacctactcttaccccctttg  300
GlyLysGlyTrpGlnProGlyThrLysAsnLys accaacacagcacaacacaatacaacacatgtgactaccaatcatggaatcggatctaac  360 agctgtgttttaaaaaaaaggGTCATCAACTTCTCGGGAAGCTACAACCCCAACGGCAAC  420
                     ValIleAsnPheSerGlySerTyrAsnProAsnGlyAsn
```

FIG.3A

```
AGCTACCTCTCCGTGTACGGCTGGTCCCGCAACCCCCTGATCGAGTACTACATCGTCGAG    480
SerTyrLeuSerValTyrGlyTrpSerArgAsnProLeuIle|Glu|TyrTyrIleValGlu

AACTTTGGCACCTACAACCCGTCCACGGGCGCCACCAAGCTGGGCGAGGTCACCTCCGAC    540
AsnPheGlyThrTyrAsnProSerThrGlyAlaThrLysLeuGlyGluValThrSerAsp

GGCAGCGTCTACGACATTTACCGCACGCAGCGCGTCAACCAGCCGTCCATCATCGGCACC    600
GlySerValTyrAspIleTyrArgThrGlnArgValAsnGlnProSerIleIleGlyThr

GCCACCTTTTACCAGTACTGGTCCGTCCGCCGCAACCACCGCTCGAGCGGCTCCGTCAAC    660
AlaThrPheTyrGlnTyrTrpSerValArgArgAsnHisArgSerSerGlySerValAsn

ACGGCGAACCACTTCAACGCGTGGGCTCAGCAAGGCCTGACGCTCGGGACGATGGATTAC    720
ThrAlaAsnHisPheAsnAlaTrpAlaGlnGlnGlyLeuThrLeuGlyThrMetAspTyr

CAGATTGTTGCCGTGGAGGGTTACTTTAGCTCTGGCTCTGCTTCCATCACCGTCAGCtaa    780
GlnIleValAlaVal|Glu|GlyTyrPheSerSerGlySerAlaSerIleThrValSer aggggctcttcttttgtgatgtgtgaaaaaaaaaaaaaggatggtggataaaagggggt    840
```

FIG.3B

Xylanase I genomic sequence

```
                        gaattctgcatatataaagccatggaagaagacgtaaaact    -61
gagacagcaagctcaactgcatagtatcgacttcaaggaaaacacgcacaaataatcatc    -1
ATGGTTGCCTTTTCCAGCCTCATCTGCGCTCTCACCAGCATCGCCAGTACTCTGGCGATG    60
MetValAlaPheSerSerLeuIleCysAlaLeuThrSerIleAlaSerThrLeuAlaMet CCCACAGGCCTCGAGCCTGAGAGCAGTGTCAACGTCACAGAGCGTGGCATGTACGACTTT    120
ProThrGlyLeuGluProGluSerSerValAsnValThrGluArgGlyMetTyrAspPhe GTTCTTGGAGCTCACAATGATCATCGCCGTCGTGCTAGCATCAACTACGACCAAAACTAC    180
ValLeuGlyAlaHisAsnAspHisArgArgArgAlaSerIleAsnTyrAspGlnAsnTyr CAAACTGGCGGACAAGTCAGCTATTCGCCTTCCAACACTGGCTTCTCAGTGAACTGGAAC    240
GlnThrGlyGlyGlnValSerTyrSerProSerAsnThrGlyPheSerValAsnTrpAsn ACTCAAGATGACTTTGTTGTGGGCGTTGGTTGGACGACTGGATCTTCTGCGtcggaggat    300
ThrGlnAspAspPheValValGlyValGlyTrpThrThrGlySerSerAla tctcatcattctgcactttgaaagcatcttctgaccaacaagcttctcttagtCCCATCA    360
                                                      ProIleA ACTTTGGCGGCTCTTTTAGTGTCAACAGCGGAACTGGCCTGCTTTCCGTCTATGGCTGGA    420
snPheGlyGlySerPheSerValAsnSerGlyThrGlyLeuLeuSerValTyrGlyTrpS GCACCAACCCACTGGTTGAGTACTACATCATGGAGGACAACCACAACTACCCAGCACAGG    480
erThrAsnProLeuValGluTyrTyrIleMetGluAspAsnHisAsnTyrProAlaGlnG
```

FIG.10A

```
GTACCGTCAAGGGAACCGTCACCAGCGACGGAGCCACTTACACCATCTGGGAGAATACCC       540
lyThrValLysGlyThrValThrSerAspGlyAlaThrTyrThrIleTrpGluAsnThrA

GTGTCAACGAGCCTTCCATCCAGGGCACAGCGACCTTCAACCAGTACATTTCCGTGCGGA       600
rgValAsnGluProSerIleGlnGlyThrAlaThrPheAsnGlnTyrIleSerValArgA

ACTCGCCCAGGACCAGCGGAACTGTTACTGTGCAGAACCACTTCAATGCTTGGGCCTCGC       660
snSerProArgThrSerGlyThrValThrValGlnAsnHisPheAsnAlaTrpAlaSerL

TTGGCCTGCACCTTGGGCAGATGAACTACCAGGTTGTCGCTGTCGAAGGCTGGGGTGGTA       720
euGlyLeuHisLeuGlyGlnMetAsnTyrGlnValValAlaVal|GluGlyTrpGlyGlyS

GTGGTTCTGCCTCACAGAGTGTCAGCAACtaggttctgttgatgttgacttggagtggat       780
erGlySerAlaSerGlnSerValSerAsn gaggggtttgagctggtatgtagtattgggggtggttagtgagttaacttgacagactgca    840
```

FIG.10B

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 1015 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: join(176..448, 557..952)

( x i ) SEQUENCE DESCRIPTION: SEQ ID NO:1:

```
AAGCTTGATG  AGGCCAAATT  ATCCGTCAAC  TGTCTTATAA  AGGAGCCCAT  GCCAAACCCC      60

CCCTAAAGAC  TCAAGAAGCC  AAACCTGAAC  AACCCCAGCA  CCTGAACAGT  CATACAACCC     120

CTCCAAGCCC  AAAAGACACA  ACAACTCCTA  CTAGCTGAAG  CAAGAAGACA  TCAAC ATG     178
                                                                  Met
                                                                    1

GTC  TCC  TTC  ACC  TCC  CTC  CTC  GCC  GGC  GTC  GCC  GCC  ATC  TCG  GGC  GTC     226
Val  Ser  Phe  Thr  Ser  Leu  Leu  Ala  Gly  Val  Ala  Ala  Ile  Ser  Gly  Val
               5                    10                        15

TTG  GCC  GCT  CCC  GCC  GCC  GAG  GTC  GAA  TCC  GTG  GCT  GTG  GAG  AAG  CGC     274
Leu  Ala  Ala  Pro  Ala  Ala  Glu  Val  Glu  Ser  Val  Ala  Val  Glu  Lys  Arg
          20                         25                        30

CAG  ACG  ATT  CAG  CCC  GGC  ACG  GGC  TAC  AAC  AAC  GGC  TAC  TTC  TAC  TCG     322
Gln  Thr  Ile  Gln  Pro  Gly  Thr  Gly  Tyr  Asn  Asn  Gly  Tyr  Phe  Tyr  Ser
      35                        40                        45

TAC  TGG  AAC  GAT  GGC  CAC  GGC  GGC  GTG  ACG  TAC  ACC  AAT  GGT  CCC  GGC     370
Tyr  Trp  Asn  Asp  Gly  His  Gly  Gly  Val  Thr  Tyr  Thr  Asn  Gly  Pro  Gly
 50                         55                        60                    65

GGG  CAG  TTC  TCC  GTC  AAC  TGG  TCC  AAC  TCG  GGC  AAC  TTT  GTC  GGC  GGC     418
Gly  Gln  Phe  Ser  Val  Asn  Trp  Ser  Asn  Ser  Gly  Asn  Phe  Val  Gly  Gly
                    70                         75                        80

AAG  GGA  TGG  CAG  CCC  GGG  ACC  AAG  AAC  AAG  TAAGACTACC  TACTCTTACC      468
Lys  Gly  Trp  Gln  Pro  Gly  Thr  Lys  Asn  Lys
               85                         90

CCCTTTGACC  AACACAGCAC  AACACAATAC  AACACATGTG  ACTACCAATC  ATGGAATCGG     528

ATCTAACAGC  TGTGTTTTAA  AAAAAAGG  GTC  ATC  AAC  TTC  TCG  GGA  AGC  TAC      580
                                 Val  Ile  Asn  Phe  Ser  Gly  Ser  Tyr
                                                 95

AAC  CCC  AAC  GGC  AAC  AGC  TAC  CTC  TCC  GTG  TAC  GGC  TGG  TCC  CGC  AAC     628
Asn  Pro  Asn  Gly  Asn  Ser  Tyr  Leu  Ser  Val  Tyr  Gly  Trp  Ser  Arg  Asn
100                       105                       110                      115

CCC  CTG  ATC  GAG  TAC  TAC  ATC  GTC  GAG  AAC  TTT  GGC  ACC  TAC  AAC  CCG     676
Pro  Leu  Ile  Glu  Tyr  Tyr  Ile  Val  Glu  Asn  Phe  Gly  Thr  Tyr  Asn  Pro
                    120                       125                      130

TCC  ACG  GGC  GCC  ACC  AAG  CTG  GGC  GAG  GTC  ACC  TCC  GAC  GGC  AGC  GTC     724
Ser  Thr  Gly  Ala  Thr  Lys  Leu  Gly  Glu  Val  Thr  Ser  Asp  Gly  Ser  Val
               135                       140                      145

TAC  GAC  ATT  TAC  CGC  ACG  CAG  CGC  GTC  AAC  CAG  CCG  TCC  ATC  ATC  GGC     772
Tyr  Asp  Ile  Tyr  Arg  Thr  Gln  Arg  Val  Asn  Gln  Pro  Ser  Ile  Ile  Gly
          150                       155                      160

ACC  GCC  ACC  TTT  TAC  CAG  TAC  TGG  TCC  GTC  CGC  CGC  AAC  CAC  CGC  TCG     820
Thr  Ala  Thr  Phe  Tyr  Gln  Tyr  Trp  Ser  Val  Arg  Arg  Asn  His  Arg  Ser
     165                       170                      175
```

| | | | | | | | | | | | | | | | |
|---|---|---|---|---|---|---|---|---|---|---|---|---|---|---|---|
| AGC | GGC | TCC | GTC | AAC | ACG | GCG | AAC | CAC | TTC | AAC | GCG | TGG | GCT | CAG | CAA | 868
| Ser | Gly | Ser | Val | Asn | Thr | Ala | Asn | His | Phe | Asn | Ala | Trp | Ala | Gln | Gln |
| 180 | | | | 185 | | | | | 190 | | | | | 195 | |

| | | | | | | | | | | | | | | | |
|---|---|---|---|---|---|---|---|---|---|---|---|---|---|---|---|
| GGC | CTG | ACG | CTC | GGG | ACG | ATG | GAT | TAC | CAG | ATT | GTT | GCC | GTG | GAG | GGT | 916
| Gly | Leu | Thr | Leu | Gly | Thr | Met | Asp | Tyr | Gln | Ile | Val | Ala | Val | Glu | Gly |
| | | | | 200 | | | | 205 | | | | | | 210 | |

| | | | | | | | | | | |
|---|---|---|---|---|---|---|---|---|---|---|
| TAC | TTT | AGC | TCT | GGC | TCT | GCT | TCC | ATC | ACC | GTC | AGC | TAAAGGGGC | 962
| Tyr | Phe | Ser | Ser | Gly | Ser | Ala | Ser | Ile | Thr | Val | Ser |
| | | | 215 | | | | | 220 | | | |

TCTTCTTTTG TGATGTGTGA AAAAAAAAAA AAGGATGGTG GATAAAAGGG GGT    1015

( 2 ) INFORMATION FOR SEQ ID NO:2:

( i ) SEQUENCE CHARACTERISTICS:
        ( A ) LENGTH: 223 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Val | Ser | Phe | Thr | Ser | Leu | Leu | Ala | Gly | Val | Ala | Ala | Ile | Ser | Gly |
| 1 | | | | 5 | | | | | 10 | | | | | 15 | |

| | | | | | | | | | | | | | | | |
|---|---|---|---|---|---|---|---|---|---|---|---|---|---|---|---|
| Val | Leu | Ala | Ala | Pro | Ala | Ala | Glu | Val | Glu | Ser | Val | Ala | Val | Glu | Lys |
| | | | 20 | | | | 25 | | | | | 30 | | | |

| | | | | | | | | | | | | | | | |
|---|---|---|---|---|---|---|---|---|---|---|---|---|---|---|---|
| Arg | Gln | Thr | Ile | Gln | Pro | Gly | Thr | Gly | Tyr | Asn | Asn | Gly | Tyr | Phe | Tyr |
| | | 35 | | | | | 40 | | | | | 45 | | | |

| | | | | | | | | | | | | | | | |
|---|---|---|---|---|---|---|---|---|---|---|---|---|---|---|---|
| Ser | Tyr | Trp | Asn | Asp | Gly | His | Gly | Gly | Val | Thr | Tyr | Thr | Asn | Gly | Pro |
| | 50 | | | | | 55 | | | | | | 60 | | | |

| | | | | | | | | | | | | | | | |
|---|---|---|---|---|---|---|---|---|---|---|---|---|---|---|---|
| Gly | Gly | Gln | Phe | Ser | Val | Asn | Trp | Ser | Asn | Ser | Gly | Asn | Phe | Val | Gly |
| 65 | | | | | 70 | | | | | 75 | | | | | 80 |

| | | | | | | | | | | | | | | | |
|---|---|---|---|---|---|---|---|---|---|---|---|---|---|---|---|
| Gly | Lys | Gly | Trp | Gln | Pro | Gly | Thr | Lys | Asn | Lys | Val | Ile | Asn | Phe | Ser |
| | | | | 85 | | | | | 90 | | | | | 95 | |

| | | | | | | | | | | | | | | | |
|---|---|---|---|---|---|---|---|---|---|---|---|---|---|---|---|
| Gly | Ser | Tyr | Asn | Pro | Asn | Gly | Asn | Ser | Tyr | Leu | Ser | Val | Tyr | Gly | Trp |
| | | | 100 | | | | | 105 | | | | | 110 | | |

| | | | | | | | | | | | | | | | |
|---|---|---|---|---|---|---|---|---|---|---|---|---|---|---|---|
| Ser | Arg | Asn | Pro | Leu | Ile | Glu | Tyr | Tyr | Ile | Val | Glu | Asn | Phe | Gly | Thr |
| | | 115 | | | | | 120 | | | | | 125 | | | |

| | | | | | | | | | | | | | | | |
|---|---|---|---|---|---|---|---|---|---|---|---|---|---|---|---|
| Tyr | Asn | Pro | Ser | Thr | Gly | Ala | Thr | Lys | Leu | Gly | Glu | Val | Thr | Ser | Asp |
| | 130 | | | | | 135 | | | | | 140 | | | | |

| | | | | | | | | | | | | | | | |
|---|---|---|---|---|---|---|---|---|---|---|---|---|---|---|---|
| Gly | Ser | Val | Tyr | Asp | Ile | Tyr | Arg | Thr | Gln | Arg | Val | Asn | Gln | Pro | Ser |
| 145 | | | | | 150 | | | | | 155 | | | | | 160 |

| | | | | | | | | | | | | | | | |
|---|---|---|---|---|---|---|---|---|---|---|---|---|---|---|---|
| Ile | Ile | Gly | Thr | Ala | Thr | Phe | Tyr | Gln | Tyr | Trp | Ser | Val | Arg | Arg | Asn |
| | | | | 165 | | | | | 170 | | | | | 175 | |

| | | | | | | | | | | | | | | | |
|---|---|---|---|---|---|---|---|---|---|---|---|---|---|---|---|
| His | Arg | Ser | Ser | Gly | Ser | Val | Asn | Thr | Ala | Asn | His | Phe | Asn | Ala | Trp |
| | | | 180 | | | | | 185 | | | | | 190 | | |

| | | | | | | | | | | | | | | | |
|---|---|---|---|---|---|---|---|---|---|---|---|---|---|---|---|
| Ala | Gln | Gln | Gly | Leu | Thr | Leu | Gly | Thr | Met | Asp | Tyr | Gln | Ile | Val | Ala |
| | | 195 | | | | | 200 | | | | | 205 | | | |

| | | | | | | | | | | | | |
|---|---|---|---|---|---|---|---|---|---|---|---|---|
| Val | Glu | Gly | Tyr | Phe | Ser | Ser | Gly | Ser | Ala | Ser | Ile | Thr | Val | Ser |
| | 210 | | | | | 215 | | | | | 220 | | | |

( 2 ) INFORMATION FOR SEQ ID NO:3:

( i ) SEQUENCE CHARACTERISTICS:
        ( A ) LENGTH: 941 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(102..392, 455..850)

( x i ) SEQUENCE DESCRIPTION: SEQ ID NO:3:

```
GAATTCTGCA TATATAAAGC CATGGAAGAA GACGTAAAAC TGAGACAGCA AGCTCAACTG        60

CATAGTATCG ACTTCAAGGA AAACACGCAC AAATAATCAT C ATG GTT GCC TTT          113
                                             Met Val Ala Phe
                                               1

TCC AGC CTC ATC TGC GCT CTC ACC AGC ATC GCC AGT ACT CTG GCG ATG        161
Ser Ser Leu Ile Cys Ala Leu Thr Ser Ile Ala Ser Thr Leu Ala Met
  5                  10                  15                  20

CCC ACA GGC CTC GAG CCT GAG AGC AGT GTC AAC GTC ACA GAG CGT GGC        209
Pro Thr Gly Leu Glu Pro Glu Ser Ser Val Asn Val Thr Glu Arg Gly
                     25                  30                  35

ATG TAC GAC TTT GTT CTT GGA GCT CAC AAT GAT CAT CGC CGT CGT GCT        257
Met Tyr Asp Phe Val Leu Gly Ala His Asn Asp His Arg Arg Arg Ala
             40                  45                  50

AGC ATC AAC TAC GAC CAA AAC TAC CAA ACT GGC GGA CAA GTC AGC TAT        305
Ser Ile Asn Tyr Asp Gln Asn Tyr Gln Thr Gly Gly Gln Val Ser Tyr
         55                  60                  65

TCG CCT TCC AAC ACT GGC TTC TCA GTG AAC TGG AAC ACT CAA GAT GAC        353
Ser Pro Ser Asn Thr Gly Phe Ser Val Asn Trp Asn Thr Gln Asp Asp
     70                  75                  80

TTT GTT GTG GGC GTT GGT TGG ACG ACT GGA TCT TCT GCG TCGGAGGATT        402
Phe Val Val Gly Val Gly Trp Thr Thr Gly Ser Ser Ala
 85                  90                  95

CTCATCATTC TGCACTTTGA AAGCATCTTC TGACCAACAA GCTTCTCTTA GT CCC         457
                                                          Pro

ATC AAC TTT GGC GGC TCT TTT AGT GTC AAC AGC GGA ACT GGC CTG CTT        505
Ile Asn Phe Gly Gly Ser Phe Ser Val Asn Ser Gly Thr Gly Leu Leu
        100                 105                 110

TCC GTC TAT GGC TGG AGC ACC AAC CCA CTG GTT GAG TAC TAC ATC ATG        553
Ser Val Tyr Gly Trp Ser Thr Asn Pro Leu Val Glu Tyr Tyr Ile Met
115                 120                 125                 130

GAG GAC AAC CAC AAC TAC CCA GCA CAG GGT ACC GTC AAG GGA ACC GTC        601
Glu Asp Asn His Asn Tyr Pro Ala Gln Gly Thr Val Lys Gly Thr Val
                135                 140                 145

ACC AGC GAC GGA GCC ACT TAC ACC ATC TGG GAG AAT ACC CGT GTC AAC        649
Thr Ser Asp Gly Ala Thr Tyr Thr Ile Trp Glu Asn Thr Arg Val Asn
            150                 155                 160

GAG CCT TCC ATC CAG GGC ACA GCG ACC TTC AAC CAG TAC ATT TCC GTG        697
Glu Pro Ser Ile Gln Gly Thr Ala Thr Phe Asn Gln Tyr Ile Ser Val
        165                 170                 175

CGG AAC TCG CCC AGG ACC AGC GGA ACT GTT ACT GTG CAG AAC CAC TTC        745
Arg Asn Ser Pro Arg Thr Ser Gly Thr Val Thr Val Gln Asn His Phe
    180                 185                 190

AAT GCT TGG GCC TCG CTT GGC CTG CAC CTT GGG CAG ATG AAC TAC CAG        793
Asn Ala Trp Ala Ser Leu Gly Leu His Leu Gly Gln Met Asn Tyr Gln
195                 200                 205                 210

GTT GTC GCT GTC GAA GGC TGG GGT GGT AGT GGT TCT GCC TCA CAG AGT        841
Val Val Ala Val Glu Gly Trp Gly Gly Ser Gly Ser Ala Ser Gln Ser
                215                 220                 225

GTC AGC AAC TAGGTTCTGT TGATGTTGAC TTGGAGTGGA TGAGGGGTTT                890
Val Ser Asn

GAGCTGGTAT GTAGTATTGG GGTGGTTAGT GAGTTAACTT GACAGACTGC A               941
```

( 2 ) INFORMATION FOR SEQ ID NO:4:

( i ) SEQUENCE CHARACTERISTICS:
        ( A ) LENGTH: 229 amino acids
        ( B ) TYPE: amino acid
        ( D ) TOPOLOGY: linear (ii) MOLECULE TYPE: protein (xi) SEQUENCE DESCRIPTION: SEQ ID NO:4:

```
Met Val Ala Phe Ser Ser Leu Ile Cys Ala Leu Thr Ser Ile Ala Ser
 1               5                  10                  15
Thr Leu Ala Met Pro Thr Gly Leu Glu Pro Glu Ser Ser Val Asn Val
                20                  25                  30
Thr Glu Arg Gly Met Tyr Asp Phe Val Leu Gly Ala His Asn Asp His
            35                  40                  45
Arg Arg Arg Ala Ser Ile Asn Tyr Asp Gln Asn Tyr Gln Thr Gly Gly
        50                  55                  60
Gln Val Ser Tyr Ser Pro Ser Asn Thr Gly Phe Ser Val Asn Trp Asn
 65                  70                  75                  80
Thr Gln Asp Asp Phe Val Val Gly Val Gly Trp Thr Thr Gly Ser Ser
                85                  90                  95
Ala Pro Ile Asn Phe Gly Gly Ser Phe Ser Val Asn Ser Gly Thr Gly
               100                 105                 110
Leu Leu Ser Val Tyr Gly Trp Ser Thr Asn Pro Leu Val Glu Tyr Tyr
           115                 120                 125
Ile Met Glu Asp Asn His Asn Tyr Pro Ala Gln Gly Thr Val Lys Gly
       130                 135                 140
Thr Val Thr Ser Asp Gly Ala Thr Tyr Thr Ile Trp Glu Asn Thr Arg
145                 150                 155                 160
Val Asn Glu Pro Ser Ile Gln Gly Thr Ala Thr Phe Asn Gln Tyr Ile
               165                 170                 175
Ser Val Arg Asn Ser Pro Arg Thr Ser Gly Thr Val Thr Val Gln Asn
           180                 185                 190
His Phe Asn Ala Trp Ala Ser Leu Gly Leu His Leu Gly Gln Met Asn
       195                 200                 205
Tyr Gln Val Val Ala Val Glu Gly Trp Gly Gly Ser Gly Ser Ala Ser
   210                 215                 220
Gln Ser Val Ser Asn
225
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

GACTCGAGAA TTCATCGA 18

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

GGVTGGCARC CNGGNACNAA 20

(2) INFORMATION FOR SEQ ID NO:7:

(i) SEQUENCE CHARACTERISTICS:

(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:7:

GACTCGAGAA TTCATCGA  18

(2) INFORMATION FOR SEQ ID NO:8:

(i) SEQUENCE CHARACTERISTICS:
(A) LENGTH: 10 amino acids
(B) TYPE: amino acid
(D) TOPOLOGY: linear (ix) FEATURE:
(A) NAME/KEY: Peptide
(B) LOCATION: 1
(D) OTHER INFORMATION: /label=Peptide
/ note= "The amino acid at position 2 labelled "Xaa" is unknown."

(xi) SEQUENCE DESCRIPTION: SEQ ID NO:8:

Gln Xaa Ile Gln Pro Gly Thr Gly Tyr Asn
1               5                   10

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:9:

AAYTAYGAYC ARAAYTAYGA  20

(2) INFORMATION FOR SEQ ID NO:10:

(i) SEQUENCE CHARACTERISTICS:
(A) LENGTH: 25 amino acids
(B) TYPE: amino acid
(D) TOPOLOGY: linear (xi) SEQUENCE DESCRIPTION: SEQ ID NO:10:

Ala Ser Ile Asn Tyr Asp Gln Asn Tyr Gln Thr Gly Gly Gln Val Ser
1               5                   10                  15
Tyr Ser Pro Ser Asn Thr Gly Phe Ser
            20                  25

(2) INFORMATION FOR SEQ ID NO:11:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:11:

CAACCGCGGA CTGCGCATCA TGGTCTCCTT CACCTCCCT  39

(2) INFORMATION FOR SEQ ID NO:12:

(i) SEQUENCE CHARACTERISTICS:
(A) LENGTH: 26 base pairs
(B) TYPE: nucleic acid
(C) STRANDEDNESS: single
(D) TOPOLOGY: linear -continued (xi) SEQUENCE DESCRIPTION: SEQ ID NO:12:

GGGAGCCGCT CGAGCGGTGG TTGCGG 26

(2) INFORMATION FOR SEQ ID NO:13:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:13:

CAACCGCGGA CTGCGCATCA TGGTTGCCTT TTCCAGCCT 39

(2) INFORMATION FOR SEQ ID NO:14:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:14:

CAGGCTCGAG GCCTGTGGGC ATCGCCAGAG 30

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: circular (xi) SEQUENCE DESCRIPTION: SEQ ID NO:15:

GACTGGCATC ATGGCGCCCT 20

ENZYME PREPARATIONS AND METHODS FOR THEIR PRODUCTION

CROSS REFERENCE TO RELATED APPLICATIONS

This application is a continuation-in-part of U.S. application Ser. No. 08/078,478, filed Jun. 18, 1993, now abandoned, which is a continuation-in-part of PCT/FI93/00221 filed May 24, 1993 and a continuation-in-part of U.S. application Ser. No. 07/889,893, filed May 29, 1992, now abandoned which is a continuation-in-part of U.S. application Ser. No. 07/524,308, filed May 16, 1990 now U.S. Pat. No. 5,298,405.

FIELD OF THE INVENTION

The present invention is related to enzyme preparations with unique enzyme profiles. Methods for the production of such enzyme preparations by genetically engineering members of the species Trichoderma are disclosed. These preparations contain high levels of xylanase enzymes and are especially useful in the pulp and paper industries.

BACKGROUND OF THE INVENTION

Cellulose is a linear polysaccharide of glucose residues connected by β-1,4 linkages. In nature, cellulose is usually associated with lignin together with hemicelluloses such as xylans and glucomannans. In the pulp and paper industry, in chemical pulping (cooking) of the wood, the major part of the lignin is extracted to get acceptable cellulose pulp product. However, the resulting pulp is brown, mainly because of the small portion of the lignin still remaining in the pulp after cooking. This residual lignin is traditionally removed in a multi-stage bleaching procedure using typically a combination of chlorine chemicals and extraction stages. Peroxide, oxygen and ozone are also used when the use of the chlorine chemicals is wanted to be reduced or avoided totally.

Hemicellulases can be used in enzyme-aided bleaching of pulps to decrease chemical dosage in subsequent bleaching or to increase brightness of the pulp (Kantelinen et al., International Pulp Bleaching Conference, Tappi Proceedings, 1–5 (1988); Viikari et al., *Paper and Timber* 7:384–389 (1991); and Kantelinen et al., "Enzymes in bleaching of kraft pulp," Dissertation for the degree of Doctor of Technology, Technical Research Centre of Finland, VTT Publications 114, Espoo, 1992). Naturally, in this use, the hemicellulase should be free of cellulases, which would harm the cellulose fibers.

The use of hemicellulose hydrolyzing enzymes in different bleaching sequences is known from WO 89/08738, EP 383,999, WO 91/02791, EP 395,792, EP 386,888 and WO 91/05908.

Other industrial applications for hemicellulolytic enzymes are in the production of thermomechanical pulps, where the aim of the use of hemicellulolytic enzymes is decreased energy consumption. Hemicellulolytic enzymes can be used to improve drainage of recycled pulp or in the production of dissolving pulps (Viikari et al., "Hemicellulases for Industrial Applications," In: *Bioconversion of Forest and Agricultural Wastes*, Saddler, J., ed., CAB International, USA (1993)).

The use of hemicellulolytic enzymes for improved water removal from mechanical pulp is known from EP 262,040, EP 334,739 and EP 351,655 and DE 4,000,558).

When the hydrolysis of biomass to liquid fuels or chemicals is considered, the conversion of both cellulose and hemicellulose is essential to obtain a high yield (Viikari et al., "Hemicellulases for Industrial Applications," In: *Bioconversion of Forest and Agricultural Wastes*, Saddler, J., ed., CAB International, USA (1993)).

Also, in the feed industry, there is a need to use a suitable combination of enzyme activities to degrade the high β-glucan and hemicellulose containing substrate.

To make the use of hemicellulolytic enzymes an economically realistic possibility in different applications, the production costs of the enzyme must be lowered. This means that the production levels must be high and no expensive purification steps can be included. The most economical way would be to choose the production strains and conditions in such a way that the culture supernatant would be rich in required activities and the side activities would be only minor components.

Consequently, there is a clear demand for enzyme preparations, which contain unique enzyme profiles, tailor-made, that is, designed specifically for the purposes of the industry in which they are to be used, and which can be obtained in a cost-effective manner, such as, for example, directly from the culture medium of the microorganism which has been modified so that it produces the desired enzymes, but not appreciable quantities of undesired enzymes.

Xylans are complex heteropolymers mainly consisting of xylose and arabinose. Xylans have a backbone consisting of β-1,4-linked xylopyranose units, which may be substituted with acetyl residues and residues of arabinose and methyl glucuronic acid (Timell, T. E., et al., *Wood Sci. Technol.* 1:45–70 (1967)). Xylans are, after cellulose, the second most abundant carbohydrate fraction of plant biomass. A number of enzymes are needed for complete hydrolysis of xylan, the most important ones belonging to the group of endo-β-xylanases (Biely, P., *Trends Biotechnol* 3:286–290 (1985); Dekker, R. F. H., in Hignehi, T., ed., *Biosynthesis and biodegradation of wood components* (Academic Press Inc., Orlando), pp. 505–533 (1985); Woodward, J., *Top Enzyme Ferment. Biotechnol.* 8:9–30 (1984)).

Various microorganisms are capable of degrading xylans, and xylanases have been found in both prokaryotes and eukaryotes (Dekker, R. F. H., Richards, G. N., *Adv. Carbohydrate Chem. Biochem.* 32:277–352 (1976)). Xylanolytic micro-organisms often produce multiple xylanases to attack the different bonds in these molecules. In a recent review, Bastawde (Bastawde, K. B., *World J. Microbiol. Biotechnol.* 8:353–368 (1992)) presented a compilation of the current knowledge about the properties and modes of action of microbial endoxylanases. There are several reports on the molecular cloning of these enzymes from bacteria (e.g. Ghangas, G. S. et al., *J. Bacteriol.* 171:2963–2969 (1989); Lin, L.-L., Thomson, J. A., *Mol. Gen. Genet.* 228:55–61 (1991); Shareck, F. et al., *Gene* 107:75–82 (1991); Scheirlinck, T. et al., *Appl Microbiol Biotechnol.* 33:534–541 (1990); Whitehead, T. R., Lee, D. A., *Curr. Microbiol.* 23:15–19 (1991)) but few from fungi (Boucher, F. et al., *Nucleic Acids Res.* 16:9874 (1988); Ito, K. et al., *Biosci. Biotec. Biochem.* 56:906–912 (1992); Maat, J. et al., in Visser, J. et al., eds., *Xylans and Xylanases* (Elsevier Science, Amsterdam), pp. 349–360 (1992); van den Broeck, H. et al., "Cloning and expression of xylanase genes from fungal origin," EP 463,706 A1 (1992)).

*Trichoderma reesei* is an efficient producer of cellulolytic and xylanolytic enzymes (Suominen, P. et al., in Kuwahara, M., Shimada, M., eds., *Biotechnology in Pulp and Paper Industry* (Uni Publishers Co., Ltd., Tokyo), pp. 439–445

(1992); Tenkanen, M. et al., *Enzyme Microb. Technol.* 14:566–574 (1992)).

*Trichoderma reesei* also produces all the enzymes needed for complete hydrolysis of native substituted xylans (Poutanen, K., et al., *J. Biotechnol.* 6:49–60 (1987)). Multiple endo-β-1,4-xylanases have been purified from culture filtrates of Trichoderma (Baker, C. J., et al., *Phytopathology* 67:1250–1258 (1977); Hromova, M., et al., *Arch. Microbiol.* 144:307–311 (1986); John and Schmidt, *Methods Enzymol.* 160A:662–671 (1988); Lappalainen, A., *Biotechnol. Appl. Biochem.* 8:437–448 (1986); Sinner and Dietrichs, *Holzforschung* 29:207–214 (1975); Tan, L. U. L, et al., *Enzyme Microb. Technol.* 7:425–430 (1985); Wood and McCrae, *Carbohydr. Res.* 148:321–330 (1986)). Two specific endoxylanases of *T. reesei* with isoelectric points at pH 5.5 (endoxylanase I) and pH 9.0 (endoxylanase II) have been characterized (Tenkanen, M., et al., *Enzyme Microb. Technol.* 14:566–574 (1992)).

There is a need for efficient microbial and especially fungal xylanase producers, for example, for producing enzyme mixtures for enzyme-aided pulp bleaching (Kantelinen, A., et al., "Hemicellulases and Their Potential Role in Bleaching," *Int. Pulp Bleaching Conference, Tappi Proceedings* 1–9 (1988); Lahtinen, T., et al., "Using Selective Trichoderma Enzyme Preparations in Kraft Pulp Bleaching," in *Biotechnology in the Pulp and Paper Industry*, Kuwahara and Shimada, eds., Uni Publishers Co., Ltd., Tokyo, Japan, pp. 129–137 (1992); Viikari, L., et al., "Bleaching with Enzymes," *Biotechnology in the Pulp and Paper Industry*, Proc. 3rd Int. Conf., Stockholm, pp. 67–69 (1986); Viikari, L., et al., *Proc. 4th Int. Symp. Wood and Pulping Chemistry, Paris* 1:151–154 (1987)).

SUMMARY OF THE INVENTION

Recognizing the importance of producing, in an economical way, higher amounts of hemicellulolytic enzymes, and producing these enzymes as an ideal combination with other wood or plant material degrading enzymes, the inventors have investigated the use of recombinant DNA techniques in the design of hosts which would be useful as a large-scale source of recombinantly produced enzymes of interest to the applications of hemicellulolytic enzymes.

These studies have resulted in the development of fungal hosts which express large amounts of desirable enzymes and preferably large amounts of hemicellulolytic enzymes.

These studies have also resulted in the development of fungal hosts which not only express large amounts of desirable enzymes, preferably hemicellulolytic enzymes, but also are deficient in at least one enzymatic component of the cellulase degradation system.

It is an object of the invention to provide fungal hosts belonging to the genera Trichoderma which are capable of expressing high levels of xylanase activity, or, fungal hosts which, in addition, are partially or completely deficient in cellulase activity.

It is a further object of this invention to provide fungal hosts which produce high levels of xylanolytic enzymes and certain cellulolytic enzymes, preferably endoglucanases, but which, in addition, are partially or completely deficient in other cellulase activity, and preferably deficient in cellobiohydrolases.

It is further an object of this invention to provide enzyme compositions which are enriched in such hemicellulase activity or which in addition are partially or completely deficient in certain cellulolytic activities.

It is a further object of this invention to isolate and clone xylanase genes from Trichoderma.

Lastly, it is further an object of this invention to provide new hosts (plant, yeast, fungal or bacterial) which contain and express such Trichoderma xylanases.

BRIEF DESCRIPTION OF THE DRAWINGS

FIG. 3A–3B shows the nucleotide (SEQ ID No: 1) and amino acid (SEQ ID No:2) sequences of the *T. reesei* xln2 gene. The coding regions are expressed in upper case letters. Peptide sequences obtained from purified protein are indicated by an underline; sequence indicated by a double underline was used for preparing the PCR primer. The TATA box is indicated by dotting. Putative signal cleavage site is marked with an arrow (↑) and putative sites for N-glycosylation with a triangle (▼). The N-terminal of the mature protein is shown with an arrow (→). The two glutamic acids proposed to be involved with an active site are boxed.

FIG. 10A and 10B shows the nucleotide (SEQ ID No:3) and amino acid (SEQ ID No:4) sequences of the *T. ressei* xln1 gene. The coding regions are indicated by upper case letters. Peptide sequences obtained from purified protein are shown underlined; the sequence with a double underline was used for preparing the PCR primer. The TATA box is indicated by dotting. Putative signal cleavage site is marked with an arrow (↑). The N-terminal of the mature protein is shown with an arrow (→). The two glutamic acids proposed to be involved with an active site are boxed.

DETAILED DESCRIPTION OF THE INVENTION

I. Definitions

Figure 1:
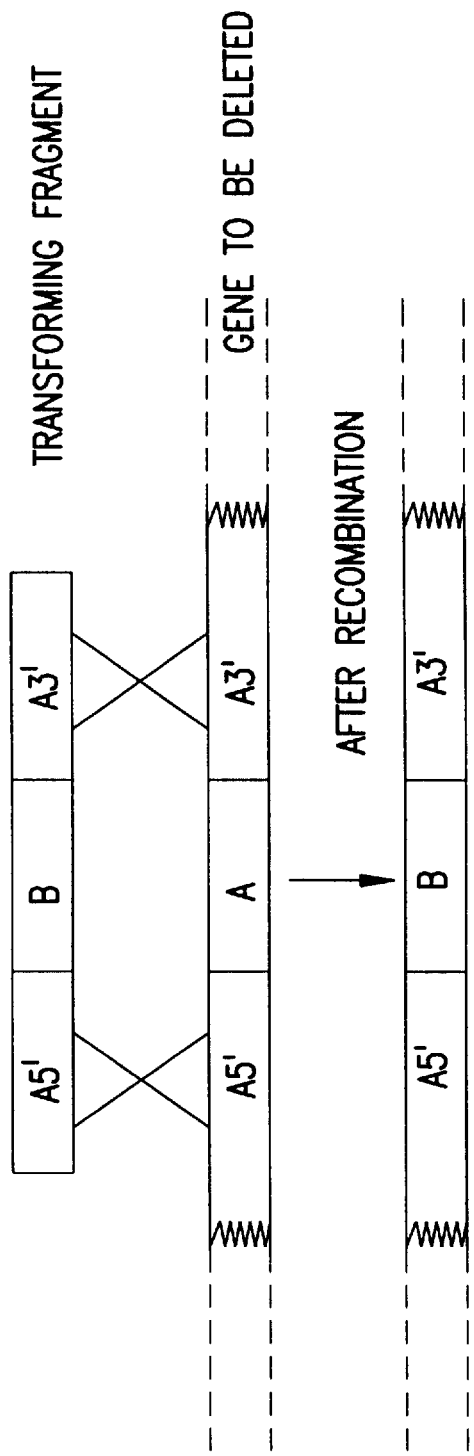
FIG. 1 shows the general strategy for deleting a gene.

In the description that follows, a number of terms used in recombinant DNA (rDNA) technology are extensively utilized. In order to provide a clear and consistent understanding of the specification and claims, including the scope to be given such terms, the following definitions are provided.

Cellulase. Cellulase is a collective term which encompasses enzymes which catalyze reactions which participate in the degradation of insoluble cellulose to soluble carbohydrate. The term "cellulase" is known in the art to refer to such a group of enzymes. For efficient hydrolysis of cellulose to glucose, at least three cellulase enzymes (three types of cellulase enzyme activity) are needed: randomly cleaving endoglucanases (1,4,-β-D-glucan glucanohydrolase, EC 3.2.1.4) which usually attack substituted soluble substrates and show no activity to crystalline cellulose; cellobiohydrolase (1,4-β-D-glucan cellobiohydrolase, EC 3.2.1.91) which is capable of degrading crystalline cellulose but has no activity towards derivatized cellulose and β-glucosidase (β-D-glucoside glycohydrolase, EC 3.2.1.21) which degrades cellobiose and cello-oligosaccharides to yield glucose. Each of the three main types of enzymes listed above occurs in multiple forms. For example, two immunologically distinctive cellobiohydrolases, CBH I and CBH II are known. In addition, 5–8 electrophoretically distinct endoglucanases are known. Synergistic action between some of these enzymes has been demonstrated. Cellulase activity is synonymous with cellulolytic activity.

The biosynthesis of cellulases is provoked or induced by cellulose, cellobiose, sophorose and lactose, and repressed by glucose or other readily utilizable carbon sources.

By a Trichoderma host which is "substantially incapable" of synthesizing one or more cellulase enzymes is meant a Trichoderma host in which the activity of one or more of the cellulase enzymes is depressed, deficient, or absent when compared to the wild-type (untransformed) Trichoderma.

Hemicellulolytic enzymes (hemicellulases). For the enzymatic degradation and modification of hemicelluloses, several different enzymes are needed, each of which are termed "hemicellulase." The two main glycanases depolymerizing the hemicellulose backbone are endo-1,4-β-D-xylanase and endo-1,4,β-D-mannanase. Small oligosaccharides are further hydrolyzed by 1,4-β-D-xylosidase, 1,4-β-D-mannosidase and 1,4-β-D-glucosidase. The side groups are split off by α-L-arabinosidase, α-D-glucuronidase and α-D-galactosidase. Esterified side groups are liberated by various esterases.

The definition of hemicellulolytic enzymes is taken from Viikari et al., "Hemicellulases for Industrial Applications," in *Bioconversion of Forest and Agricultural Wastes* (1992).

Enzyme preparation. By "enzyme preparation" is meant a composition containing enzymes which have been extracted (either partially or completely purified) from fungi or the medium used to grow such fungi. Therefore, the term "enzyme preparation" is meant to include a composition comprising medium previously used to culture such fungi and any enzymes which the fungi have secreted into such medium during the culture.

Culture medium. By culture medium is meant a medium previously used to culture a fungi ("spent" culture medium), such culture medium containing enzymes which the fungi have secreted into the medium during the culture. The culture medium is usable as such or as partially or completely purified, concentrated, dryed or immobilized. If desired, the expressed endoglucanase protein may be further purified in accordance with conventional conditions, such as extraction, precipitation, chromatography, affinity chromatography, electrophoresis, or the like.

Bio-bleaching. By "bio-bleaching" is meant the extraction of lignin from cellulose pulp after the action of hemicellulose degrading enzymes with or without lignin degrading enzymes. Removal of the lignin may be restricted by hemicelluloses either physically (through reprecipitation onto the fiber surface during cooking) or chemically (through lignin-carbohydrate complexes). The hemicellulase activity partially degrades the hemicellulose, which enhances the extractability of lignins by conventional bleaching chemicals (like chlorine, chlorine dioxide, peroxide, etc.) (Viikari et al., "Bleaching with Enzymes" in *Biotechnology in the Pulp and Paper Industry*, Proc. 3rd Int. Conf., Stockholm, pp. 67–69 (1986); Viikari et al., "Applications of Enzymes in Bleaching" in *Proc. 4th Int. Symp. Wood and Pulping Chemistry*, Paris, Vol. 1, pp. 151–154 (1987); Kantelinen et al., "Hemicellulases and their Potential Role in Bleaching" in *International Pulp Bleaching Conference, Tappi Proceedings*, pp. 1–9 (1988)). The advantage of this improved bleachability is a lower consumption of bleaching chemicals and lower environmental loads or higher final brightness values. Hemicellulolytic enzymes improve bleachability by making the lignin removal with conventional bleaching chemicals easier.

Gene. A DNA sequence containing a template for a RNA polymerase. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "anti-sense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA and from which intervening sequences (introns) have been removed.

By an enzyme homologous to a Trichoderma host of the invention is meant that an untransformed Trichoderma of the same species as the host species naturally produces some amount of the native protein; by a gene homologous to a Trichoderma host of the invention is meant a gene found in the genome of an untransformed Trichoderma of the same species as the host species.

By an enzyme heterologous to a Trichoderma host of the invention is meant that an untransformed Trichoderma of the same species as the host species does not naturally produce some amount of the native protein; by a gene heterologous to a Trichoderna host of the invention is meant a gene not found in the genome of an untransformed Trichoderma of the same species as the host species.

Hybridization. By hybridization are meant conditions, under which all Trichoderma xylanase genes hybridize to the nucleic acid sequence encoding the amino acid sequence of *T. reesei* pI 5.5 xylanase or to the nucleic acid sequence encoding the amino acid sequence of *T. reesei* pI 9 xylanase. These conditions are characterized by hybridization preferably in 60° to 68° C. in the presence of 6×SSC+0.1% SDS and washing in in 60° to 68° C. in the presence of 6×SSC+0.1% SDS.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are tetracycline resistance or ampicillin resistance. The word "vector" is sometimes used for "cloning vehicle." Alternatively, such markers may be provided on a cloning vehicle which is separate from that supplying the gene of interest.

Expression vehicle. A vehicle or vector similar to a cloning vehicle but which is capable of expressing a gene of interest which has been cloned into it, after transformation into a desired host. In a preferred embodiment, such expression vehicle provides for an enhanced expression of a gene of interest which has been cloned into it, after transformation into a desired host.

In a preferred embodiment, the gene of interest which is provided to a fungal host as part of a cloning or expression vehicle integrates into the fungal chromosome. Sequences which derive from the cloning vehicle or expression vehicle may also be integrated with the gene of interest during the integration process.

The gene of interest may preferably be placed under the control of (i.e., operably linked to) certain control sequences such as promoter sequences provided by the vector (which integrate with the gene of interest). If desired, such control sequences may be provided by the fungal host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

II. Genetic Engineering of the Trichoderma Hosts

The process for genetically engineering the hosts of the invention is facilitated through the cloning of genetic sequences which are capable of encoding a desired enzymic activity and through the expression of such genetic sequences. As used herein, the term "genetic sequences" is intended to refer to a nucleic acid molecule (preferably DNA). Genetic sequences which are capable of encoding a desired enzyme are derived from a variety of sources. These sources include genomic DNA, cDNA, synthetic DNA, and combinations thereof.

The mesophilic imperfect fungus *Trichoderma reesei* (formerly *T. viride*) is classified as a member of Fungi imperfecti. Fungi imperfecti is a catch-all category of fungi which have no sexual reproduction or obvious affinities with sexually reproducing genera, such as the highly characteristic Aspergillus. Although Trichoderma has been reported to possess a poorly defined sexual stage being an imperfect state of the perfect ascomycete species Hypocrea, the genera Aspergillus and Trichoderma are clearly to be considered taxonomically very different.

The improved enzyme preparations according to this invention are produced by the fungus Trichoderma which has been modified by recombinant DNA techniques. The Trichoderma hosts of the invention are modified so as to be able to produce high levels of enzymes, preferably hemicellulases. In addition, these hosts may be modified so as to be totally deficient in at least one cellulase enzyme (whose activity is undesirable during pulp and paper processing). Thus, although the remaining cellulase activities may be unaffected, the Trichoderma hosts of the invention are partially or completely deficient in the necessary complement of enzymes which will fully degrade cellulose to glucose, and, as a result, such degradation is greatly lowered or completely blocked.

IIa. Transformation of Trichoderma with a New Genetic Construct

In one embodiment, the Trichoderma hosts of the invention which may be partially or completely deficient in at least one cellulase activity are transformed with a genetic construct capable of expressing at least one desired pulp and paper processing enzyme which is homologous to Trichoderma, so as to provide for increased amounts of this enzyme in the Trichoderma host. Examples of desired pulp and paper processing homologous enzymes include, for example, hemicellulases and pectin-degrading enzymes. Trichoderma is inherently capable of producing a variety of hemicellulases including endoxylanases, mannanases, β-xylosidase, α-arabinosidase, α-glucuronidase, and acetyl esterase, the activity of any of which may be a desired enzyme in the enzyme preparations of the invention. Also, native Trichoderma produces minor amounts of pectin degrading enzymes like polygalacturonase which may be classified as a desired enzyme in the enzyme preparations of the invention. Further, any other Trichoderma enzyme which oxidizes cellulose may be utilized in the enzyme preparations of the invention and may be a desired enzyme.

Comparison with xylanolytic enzymes produced by *Trichoderma reesei* QM 9414, *Aspergillus awamori* VTT-D-75028, *Fusarium oxysporum* VTT-D-80134, *Bacillus subtilis* ATCC 12711 and *Streptomyces olivochromogenes* ATCC 21713 has shown that the highest xylanase activity was produced by *T. reesei*. Therefore, under conditions where it is desired to retain xylanase activity, *T. reesei* is an advantageous host. (Poutanen, K., "Characterization of Xylanolytic Enzymes for Potential Applications" in Disssertation for the degree of Doctor of Technology, Technical Research Centre of Finland, Publications 47).

Further, although the above preparations from the different microbial origins differed with respect to β-xylosidase activity and side-group cleaving activities, the *T. reesei* culture filtrate contained all the side-group cleaving activities assayed (acetyl esterase, α-glucuronidase and α-arabinosidase) whereas those from *F. oxysporum* and *S. olivochromogenes* only contained esterase. Thus Trichoderma is also advantageous as a host because it naturally produces a wide spectrum of xylanolytic enzymes the proportions of which can be manipulated by genetic engineering for different applications to provide enzyme preparations tailored for those purposes.

According to this invention, the genetic constructs which encode homologous enzymes which are desirable for pulp and paper processing purposes may be introduced into the genome of Trichoderma and enhanced expression can also be achieved by using strong promoters such as cbh1 and, if desired, additional or modified regulatory regions, such as, for example, enhancer sequences. Preferably, such regulatory sequences are homologous to Trichoderma. A regulatory region, and especially a promoter, may be modified to contain only those sequence elements needed for expression and/or to retain a region which is responsible for high expression levels. Enhancer sequences may be introduced concurrently with the gene of interest as a separate DNA element but operably-linked to such gene of interest, for example, as a DNA sequence which is colinear with that providing the gene of interest (for example, in a 5' or 3' non-translating sequence, or in an intron).

In a highly preferred embodiment, the homologous gene introduced to the genome of Trichoderma is a gene encoding a homologous hemicellulase, preferably xylanase. The two main xylanases produced by *T. reesei* have been purified (Tenkanen, M., *Enzyme Microb. Technol.* 14:566–574 (1992)). The enzymes have isoelectric points of 5.5 (XYLI) and 9.0 (XYLII) and their molecular masses are 19 and 20 kDa, respectively.

The xylanase I enzyme from *Trichoderma reesei* has optimal activity in the more acid pH region, whereas xylanase II has its pH optimum in the near-neutral pH range. Because of the different properties of the two xylanases, either one or a mixture of these enzymes can be used in different applications (WO 92/03541 and Viikari et al., "Important Properties of Xylanases for Use in Pulp and Paper industry" In: *Biotechnology in Pulp and Paper Industry*, Kuwahara, M. and Shimada, M., eds., Proc. 5th Int. Conf. Biotechnology in Pulp and Industry, Uni Publishers Co., Ltd., Tokyo, 1992, pp. 101–106).

According to the invention, it is possible by using genetic engineering methods to enrich the desired xylanolytic activity to the culture medium and use this culture medium in a desired application. For example, in some bleaching sequences and bleaching conditions it may be advantageous to use xylanase I (more acid pH region), in some other bleaching sequences and bleaching conditions xylanase II may be preferably (alkaline or near neutral pH range).

In some applications, although one cellulolytic activity may be eliminated, reduced, inactivated, or repressed, it may be desirable to introduce a gene encoding a different cellulolytic enzyme into the host cells so as to enhance one specific cellulolytic activity. In addition to hemicellulolytic activity, for example, in feed industry, an enzyme preparation comprising an elevated amount of endoglucanase may be used. Thus, in those preparations in which such hydrolysis is desired, a host which expresses elevated levels of endoglucanases, in addition to xylanases or other hemicellulases may be used.

In another embodiment, the Trichoderma host which already expresses a homologous form of an enzyme is transformed with a genetic construct encoding a heterologous form of the same enzyme. In a further embodiment, a Trichoderma host which does not express a certain enzyme is transformed with one or more genetic constructs encoding enzyme(s) heterologous to Trichoderma.

According to this invention increased amounts of a heterologous enzyme whose activity is desired for pulp and paper processing purposes are achieved by introducing the gene producing such heterologous desired enzyme into a specific locus and/or introducing the gene in multicopies into the genome of Trichoderma as described above.

In a preferred embodiment, the gene encoding a desired enzyme is inserted into the cbh1 locus such that it is operably linked to the strong cbh1 promoter. As described below, enhanced production is achieved by using strong promoters such as cbh1. Increased amounts of the desired heterologous enzyme are also achieved when Trichoderma's cellulase producing capacity is lowered in general, even if the heterologous gene is not inserted into the cbh1 locus.

A gene encoding a desired enzyme, either homologous or heterologous, such as a hemicellulose hydrolyzing enzyme, can be integrated into the genome of Trichoderma by inserting the gene into a general expression vector, for example, pAMH110, which is described in the patent application EP 244,234. pAMH110 is derived from pUC19 (Yanish-Perron et al., Gene 33:103–119 (1985)) and includes the promoter and terminator of the cbh1 gene and a stuffer fragment between the promoter and terminator sequences which can be removed by digestion with SacIh and NdeI. After the ends are made blunt, any DNA, cDNA or chromosomal DNA can be inserted between the promoter and terminator. The desired gene can be inserted to the cbh1 expression cassette in the plasmid pAMH110 between the cbh1 promoter and terminator.

Transcriptional regulatory elements of other genes may be used where it is desired not to use the cbh1 elements. For example a vector construction comprising the 3-phosphoglycerate kinase gene (pgk) transcriptional regulatory regions may be used as 3-phosphoglycerate kinase, a key enzyme for ATP generation by glycolysis, is expressed in the presence of glucose under which conditions the synthesis of cellulases is repressed.

While the inventors do not intend to be bound by any particular theory, the effectiveness of the expression of the desired gene seems to be dependent both on the number of copies of the desired gene integrated to the genome of Trichoderma and on the location of integration of the gene in the genome. In a preferred embodiment, the integration of a desired gene is directed into a specific locus. The use of a linear DNA helps in directing the integration into a homologous locus. In a highly preferred embodiment, the integration of a desired gene is directed into the Trichoderma cbh1 locus.

The DNA constructions prepared according to this invention can be used to transform any Trichoderma strain. Such strains include, for example, *T. reesei* strains QM9414 (ATCC 26921), RUT-C-30 (ATCC 56765), and highly productive mutants like VTT-D-79125, which is a descendant of QM9414 (Nevalainen 1985, Technical Research Centre of Finland Publications 26, (1985), Espoo, Finland). The transformation of Trichoderma may be performed by any technique known in the art and especially by the technique taught in EP 244,234.

The Trichoderma host cells may be cultivated and the desired enzymes produced by cultivating the host strain having the desired properties under any conditions which allow expressing of the desired enzymes. For example, a Trichoderma host strain having the desired properties may be cultivated in a liquid cultivation medium, which may comprise, for example, 6% Solka Floc cellulose, 3% distiller's spent grain, 0.5% $KH_2PO_4$, 0.5% $(NH_4)_2SO_4$, 0.1% struktol. The cellulase production by Trichoderma strains is sensitive to glucose repression and require an inducer such as, for example, cellulose, lactose or sophorose (Allen et al., *Biotechnology and Bioengineering* 33:650–656 (1989)). The pH in Trichoderma cultivation should be kept at approximately pH 5 by the addition of phosphoric acid or ammonia and the temperature may be kept at 30° C. during the cultivation. However, the temperature should be adjusted according to the strain and according to the enzyme preparation to be produced (Merivuori et al., *Biotechnology Lett.* 12:117–120 (1990)).

IIb. DNA Cloning

Vector systems may be used in the method of producing Trichoderma hosts for the production of the enzyme preparations of the invention. One element provided by such vector construction may encode the sequence of at least one homologous gene the activity of which it is desired to eliminate, reduce, inactivate, delete or repress. Such vector construction (a) may further provide a separate vector construction (b) which encodes at least one desired gene to be integrated to the genome of Trichoderma and (c) a selectable marker coupled to (a) or (b). Alternatively, a separate vector may be used.

The cloned DNA which is used in the hosts of the invention may or may not include naturally occurring introns. Moreover, such genomic DNA may be obtained in association with the native 5' promoter region of the DNA genetic sequences and/or with the 3' transcriptional termination region if such sequences are capable of functioning in Trichoderma. Further, such genomic DNA may be obtained in association with the genetic sequences which encode the 5' non-translated region of the mRNA and/or with the genetic sequences which encode the 3' non-translated region. To the extent that the Trichoderma host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation. Genomic DNA can be extracted by means well known in the art (for example, see *Guide to Molecular Cloning Techniques*, S. L. Berger et al., eds., Academic Press (1987)). Alternatively, mRNA can be isolated from any cell which produces or expresses the desired protein, and used to produce cDNA by means well known in the art (for example, see *Guide to Molecular Cloning Techniques*, S. L. Berger et al., eds., Academic Press (1987)). Preferably, the mRNA preparation used will be enriched in mRNA coding for a desired protein, either naturally, by isolation from a cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

Libraries containing clones encoding a desired protein may be screened and a clone to the desired protein identified by any means which specifically selects for that protein's DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for the proteins desired in this invention which can be used to identify clones to such protein can be designed from knowledge of the amino acid sequence of the protein.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: *Molecular Biology of the Gene*, 3rd Ed., W. A. Benjamin, Inc., Menlo Park, Calif. (1977)), one or more different oligonucleotides can be identified from the amino acid sequence, each of which would be capable of encoding the protein. The probability that a particular oligonucleotide will, in fact, constitute the actual protein's sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the protein's sequence is identified.

The suitable oligonucleotide, or set of oligonucleotides, which is capable of encoding a fragment of the protein's gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate the desired cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, D.C. (1985)).

Cloning techniques using oligonucleotides and PCR are also well known in the art ("PCR Protocols" in *A Guide to Methods and Application*, Innis et al., eds., Academic Press, San Diego (1990)). Those members of the above-described gene library which are found to be capable of such hybridization are then analyzed to determine the extent and nature of the desired genomic coding sequences which they contain.

To facilitate the detection of the desired DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are nonradioactive labels such as digoxigenin-nucleotides (dUTP) or radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively or nonradioactively labeled by several methods known in the art and commercial kits for these purposes are available.

Alternatively, polynucleotides are also useful as nucleic acid hybridization probes when labeled with a non-radioactive marker such as biotin, digoxigenin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

Thus, in summary, the actual identification of protein's sequence (or a partial sequence of the protein) permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the protein's gene.

In an alternative way of cloning a gene, a library is prepared using an expression vector, by cloning DNA or, more preferably cDNA prepared from a cell capable of expressing a desired protein, into an expression vector. The library is then screened for members which express the protein, for example, by screening the library with antibodies to the protein.

The above discussed methods are, therefore, capable of identifying genetic sequences which are capable of encoding a desired protein or fragments of this protein. In order to further characterize such genetic sequences, and, in order to produce the recombinant protein, it is desirable to express the proteins which these sequences encode. Such expression identifies those clones which express proteins possessing characteristics of the desired protein. Such characteristics may include the ability to specifically bind antibodies directed against the protein, the ability to elicit the production of antibody which are capable of binding the protein, and the ability to provide a protein specific function to a recipient cell, among others.

The cloned protein encoding sequences, obtained through the methods described above, and preferably in a double-stranded form, may be operably linked to sequences controlling transcriptional expression in an expression vector, and introduced into a Trichoderma host cell to produce recombinant protein or a functional derivative thereof. Depending upon which strand of the protein encoding sequence is operably linked to the sequences controlling transcriptional expression, it is also possible to express an antisense RNA or a functional derivative thereof.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the Trichoderma hosts requires the use of regulatory regions functional in such hosts. A wide variety of transcriptional and translational regulatory sequences can be employed, since Trichoderma generally recognize eukaryotic host transcriptional controls, such as, for example, those of other filamentous fungi. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

IIc. Regulatory Regions

In a preferred embodiment, a desired protein is secreted into the surrounding medium due to the presence of a homologous Trichoderma secretion signal sequence. If a desired protein does not possess its own signal sequence, or if such signal sequence does not function well in Trichoderma, then the protein's coding sequence may be operably linked to a signal sequence homologous or heterologous to Trichoderma. The desired coding sequence may be linked to any signal sequence which will allow secretion of the protein from a Trichoderma host, for example, the signal sequence of the Trichoderma cellobiohydrolase I protein. Such signal sequences may be designed with or without specific protease sites such that the signal peptide sequence is amenable to subsequent removal.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., substrate or metabolite regulation. Also of interest are constructs wherein both (a) a desired protein's mRNA and (b) antisense RNA directed to a cellulase enzyme are provided in a transcribable forms such that expression of the desired protein's mRNA is accompanied by antisense RNA repression of the expression of one of the host's cellulase enzymes.

Translational signals are not necessary when it is desired to express antisense RNA sequences.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

The vectors of the invention may further comprise other operably linked regulatory elements such as enhancer sequences.

IId. Detecting Stable Transformants of Trichoderma

In a preferred embodiment, genetically stable transformants of Trichoderma are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct (s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

The DNA encoding sequences, obtained through the methods above, will provide sequences which by definition, encode a desired protein and which may then be used to obtain a desired protein's antisense RNA genetic sequences as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of an antisense RNA in the transformed cell. Antisense RNA and its expression may be used to interact with an endogenous DNA or RNA in a manner which inhibits or represses transcription or translation of the gene in a highly specific manner. Use of antisense RNA probes to block gene expression is discussed in Lichtenstein, C., *Nature* 333:801–802 (1988).

Trichoderma is an especially useful and practical host for the synthesis of the enzyme preparations of the invention because Trichoderma is capable of secreting protein at large amounts, for example, concentrations as much as 40 g/L culture fluid have been reported; the homologous Trichoderma cbh1 promoter provides a very convenient promoter for expression of genes-of-interest because it is a strong, single copy promoter which normally directs the synthesis of up to 60% of the secreted protein from the Trichoderma host; the transformation system is highly versatile and can be adapted for any gene of interest; the Trichoderma host provides an "animal cell type" high mannose glycosylation pattern; and culture of Trichoderma is supported by previous extensive experience in industrial scale fermentation techniques.

III. Trichoderma Hosts Deficient in At Least One Cellulase Enzyme

According to this invention, it is also possible to enrich Trichoderma hosts for an enzyme whose activity is desirable for pulp and paper processing purposes by inactivating or eliminating at least one cellulase enzyme. In one embodiment, the cbh1 gene is merely mutated. Since the majority of the secreted proteins of Trichoderma may be the cellulase activity encoded by the gene cbh1, (the cellobiohydrolase, CBHI, protein), by constructing Trichoderma hosts in which the cbh1 gene is mutated to an inactive form, the relative percent of the remaining proteins secreted by Trichoderma in the culture medium may be increased. In another embodiment, a desired gene is inserted preferably into the cbh1 locus such that expression of the desired gene is operably linked to the strong cbh1 promoter. In a highly preferred embodiment, a casette comprising a desired gene already operably linked to the homologous cbh1 promoter is inserted into the cbh1 locus.

In the hosts of the invention, any one, some, or all of the cellulolytic enzymes may be eliminated, reduced, inactivated, or repressed by methods known in the art so as to result in the host's partial or complete inability to degrade cellulose to glucose. Undesired cellulolytic enzyme activities can be eliminated, reduced, inactivated, or repressed by several methods, e.g., by inactivating the gene(s) encoding such enzyme (for example, by introducing a frame-shift mutation to the gene), by deleting the entire whole gene or large segments of the gene, by replacing the gene with another DNA via homologous recombination, by compensation of the gene region, by additional integration, by double crossing-over, and by transforming the host cell with a genetic construct capable of expressing an antisense RNA directed against the coding sequence for that gene, etc.

For example, inactivation of genes coding for cellulolytic activities may be performed as described in European Patent Applications EP 137,280 and EP 244,234.

Trichoderma fungi produce large amounts of identical, predominantly haploid uninucleate conidia which constitute excellent material for various mutagenic treatments. However, even a haploid mutated nucleus can produce a heterokaryotic colony (mycelium) if a mutation becomes initially fixed only in one of the two strands of the DNA double helix (mosaicism). The amount of mosaic mutants depends on both the mutagen and dose used. In fungi forming haploid uninucleate conidia, the problem of heterokaryotic mycelium can be handled by allowing conidiation and by reisolation of colonies originating from single separate conidia. This cycle can be repeated several times.

Examples of chemical mutagens useful for mutagenizing the Trichoderma hosts of the invention include alkylating agents, such as, for example, N-methyl-N'-nitro-N-nitrosoguanidine (NTG), ethylmethanesulphonate (EMS) and diethylsulphate (DES). Hydroxylamine and chemicals deaminating DNA bases such as nitrous acid are also useful. Ionizing radiation (γ- and X-rays) as well as ultraviolet irradiation (UV) are examples of physical mutagens useful in Trichoderma strain mutagenesis.

The use of solid media permits rapid screening of thousands of colonies arising from mutagenized conidia for the presence or absence of specific enzymes and allows quantitative estimation of the amount of enzyme produced.

Several types of solid media for detection of enzymes, for example, extracellular amylolytic enzymes, pectinase, protease, chitinase, β-galactosidase and cellulase, lipase, urease, RNAase and DNAase are known in the art.

Many fungi form large diffuse colonies when grown on solid media. Addition of chemical agents restrictive to colony growth may therefore be desired to allow development of more than one (up to 100) colony per one plate. Among agents used for the purpose are rose bengal, oxgall and phosphon D, Triton X-100 and saponin. With some fungi, replica plating technique analogous to that developed for bacteria can, in certain cases, be used to test the properties of fungal colonies on different growth media.

Screening on plates is usually followed by cultivation of the selected colonies in shake flasks in a liquid production medium for measurement of enzyme activity. The best isolates showing enhanced enzyme production in shake flask scale may be in a second round of mutagen treatment if desired.

Homologous genes which it is desirable to inactivate or delete according to this invention include, for example, the cellulase genes cbh1, cbh2, egl1, egl2 (formerly egl3; Saloheimo et al., *Gene* 63:11–21 (1988)) (which encode the proteins cellobiohydrolase I, cellobiohydrolase II, endoglucanase I and endoglucanase II) or combinations of these genes. Eliminating the activity of any of these genes will result in a host which is partially or completely deficient in its ability to degrade cellulose to glucose. Such elimination of cellulolytic activity may be achieved at the genomic level, by eliminating the gene or modifying it into a form which is incapable of expression. Such elimination may also be achieved at the translational level, by hybridizing the mRNA which encodes the protein to an antisense RNA to a degree which prevents the translation of the hybridized RNA.

In a preferred embodiment, a cellulase activity is selectively inactivated so that some, but not all of the cellulase components are inactivated. For example, if it is desired to maintain the host's ability to hydrolyze β-glucan, then the endoglucanase genes would not be inactivated.

The inactivation of, e.g., one of the cellulase genes can be based on transformation of *Trichoderma reesei* with a plasmid carrying a defected gene as described in patent application EP 244,234. Homologous recombination of the plasmid at the chromosomal cellulase gene locus causes insertional inactivation of the endogenous *T. reesei* cellulase gene. The plasmid used for transformation contains only part of the cellulase coding region and produces inactive protein. No 5' flanking sequences are included. A frameshift mutation can also be introduced to the truncated coding region. A selection marker, (for example amdS (acetamidase) or argB (ornithine carbamoyl transferase)) or a marker for screening (for example, lacZ) can be coupled to the plasmid used for the transformation or the transformation can be done as a cotransformation, which means that the selectable marker and the defected gene are on different plasmids (EP 244,234). Inactivation of a gene with homologous recombination may be done with a circular DNA, which integrates in a colinear manner into the Trichoderma chromosomal DNA.

The deletion of an undesired gene can be done by using a strategy the principle of which is described in FIG. 1. The recipient strain is transformed with a linear DNA fragment containing a selectable marker gene (like trpC, argB or amdS) and/or a foreign desired gene of interest which is to be expressed, flanked by the 5' and 3' flanking regions of the gene to be deleted. Homologous recombination at the A locus will thus lead to replacement of the A gene with the selection marker and/or desired gene B. If the 5' region in the transforming fragment is taken upstream from the promoter area, the promoter will also be removed in the resulting replacement strain. Gene A can be any Trichoderma gene, preferably a cellulase gene, the flanking regions of which can be cloned/isolated. Moreover the linear DNA fragment can be ligated to form a circular plasmid or in addition the circular form may contain DNA needed for replication in bacteria (e.g., in *E. coli*). The linear DNA fragments used in deletion of undesired genes can be constructed for example from pUC19 plasmids (Yanish-Perron et al., *Gene* 33:103–119 (1985)).

This method is described in more detail in the Example 1B which describes the deletion of cbh2 gene from the genome of Trichoderma by said method.

Clones of the cellulase enzymes have been described which may be used to design mutant sequences for inactivation of homologous sequences in the hosts of the invention. Any mutant sequence which results in the inactivation of the enzyme's activity may be used. For example, the gene for the native cellobiohydrolase CBH I sequence has been cloned by Shoemaker et al. (Shoemaker, S., et al., *Bio/Technology* 1:691–696 (1983)) and Teeri et al. (Teeri, T., et al., *Bio/Technology* 1:696–699 (1983)) and the entire nucleotide sequence of the gene is known (Shoemaker, S., et al., *Bio/Technology* 1:691–696 (1983)). From *T. reesei*, the gene for the major endoglucanase (EG I) has also been cloned and characterized (Penttilä, M., et al., *Gene* 45:253–263 (1986); EP 137,280; Van Arstel, J. N. V., et al., *Bio/Technology* 5:60–64). Other isolated cellulase genes are cbh2 (Patent Application WO 85/04672; Chen, C. M., et al., Bio/Technology 5:274–278 (1987)) and egl2 (originally egl3 (Saloheimo, M., et al., Gene 63:11–21 (1988)).

IV. The Enzyme Preparation

According to the invention, there is provided a method for producing high levels of enzymes, preferabaly hemicellulases, desirable for pulp and paper processing. There is also provided a method for producing an enzyme preparation partially or completely deficient in cellulolytic activity (that is, in the ability to completely degrade cellulose to glucose) and enriched in enzymes desirable for pulp and paper processing, preferably hemicellulases. By "deficient in cellulolytic activity" is meant a reduced, lowered, depressed, or repressed capacity to degrade cellulose to glucose. Such preparations may be obtained directly from the hosts of the invention. Further, if desired activities are present in more than one recombinant host, such preparations may be isolated from the appropriate hosts and combined prior to use in the method of the invention.

It is envisioned that enzyme preparation which are enriched or partially or completely deficient in specific enzymatic activities will be provided so as to satisfy the requirements of a specific utility in various applications in the pulp and paper industry and in fodder production. Enzyme activities may be added or deleted as described above to provide, remove or retain or lower a desired activity. For example, if the intended application is improvement of the strength of the mechanical mass of the pulp, then the enzyme preparation of the invention may provide enzymes which enhance or facilitate the ability of cellulose fibers to bind together. In a similar manner, in the application of pulp milling, the enzyme preparation of the invention may provide enzymes which enhance or facilitate such swelling.

To obtain the enzyme preparations of the invention, the recombinant hosts described above having the desired properties (that is, hosts substantially incapable of expressing one or more cellulase enzymes and capable of expressing the desired enzymes) are cultivated under suitable conditions, the desired enzymes are secreted from the Trichoderma hosts into the culture medium, and the enzyme preparation is recovered from said culture medium by methods known in the art.

The enzyme preparation can be produced by cultivating the Trichoderma strain in a fermentor having the desired properties for example in a liquid cultivation medium, which may comprise for example 6% Solka Floc cellulose (BW40, James River Corporation, Hackensack, N.J.), 3% distiller's spent grain, 0.5% $KH_2PO_4$, 0.5% $(NH_4)_2SO_4$, and 0.1% struktol as an antifoaming agent (struktol SB 2023, Schill & Seilacher, Hamburg, FRG). The cellulase production of Trichoderma strains is sensitive to glucose repression and require an inducer (cellulose, lactose or sophorose) (Allen et al., *Biotechnology and Bioengineering* 33:650–656 (1989)). The pH should preferably be kept at approximately pH 5 by the addition of phosphoric acid or ammonia and the temperature at 30° C. during the cultivation. However, the temperature may be adjusted according to the strain and according to the enzyme preparation to be produced (Merivuori et al., *Biotechnology Letters* 12(2):117–120 (1990)).

The enzyme preparation is recovered from the culture medium by using methods well known in the art. However, because the hosts of the invention may be partially or completely deficient in cellulase activity, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the Trichoderma hosts.

If desired, an expressed protein may be further purified in accordance with conventional conditions, such as extraction, precipitation, chromatography, affinity chromatography, electrophoresis, or the like.

The Trichoderma and enzyme preparations of the invention have further application in fodder production. For example, fodder treated with the enzyme preparations of the invention would be of great food benefit to farm animals because it would be easier for them to digest.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Materials and Methods

Transformation of *T. reesei*

Transformation of *T. reesei* and selection of $AmdS^+$ and $ArgB^+$ transformants were carried out as described by Penttila et al., Gene 61:155–164 (1987).

Phleomycin resistant transformants were screened as described by Durand et al. in: Biochemistry and Genetics of Cellulose Degradation, p. 135–151, 1987, J.-P. Aubert, P. Beguin and J. Millet (eds.), Academic Press, New York.

In cotransformation with p3SR2 and pAMH 111, equal molar amounts of plasmid DNA (5–10 µg) were used. In transformations conferring phleomycin resistance, the relative amounts of plasmid DNA used were 1:1 or 2:1 for pAMH111 and pAN8-1 respectively. When cotransformation was carried out using p3SR2 and pMS4, the plasmid pMS4 was added in 3–4 times molar excess. Transformants were purified through conidia; that is, the conidial suspension was plated again on the selective medium so that every colony started from a single conidia.

In transformations with a linear DNA fragment, the amount of DNA used varied from 2 to 5 µg. The selection marker (amdS (acetamidase) or argB (ornithine carbamoyl transferase, OTCase, E.C.2.1.3.3)or trpC(tryptophane)) was within the transforming fragment.

Isolation and Analysis of DNA

Plasmid DNA from *E. coli* was isolated using standard methods (Maniatis et al. 1982, *Molecular Cloning: A Laboratory Manual*, Cold Spring Harbor Laboratory, Cold Spring Harbor, N.Y.). Chromosomal DNA was isolated from *T. reesei* using the method of Raeder and Broda, *Lett. Appl. Microbiol.* 1:17–20 (1985)). Southern and Northern hybridizations were performed by standard techniques (Maniatis et al. supra, 1982). Western blotting was carried out according to Maniatis et al., supra, 1982).

Liquid Cultivation Media and Conditions for Trichoderma

All Trichoderma liquid cultures were started from conidiospores grown on potato dextrose agar as described by Bailey and Nevalainen, *Enzyme Microb. Technol.* 3:153–157 (1981)). Liquid cultivations in shake flasks were performed according to Bailey and Nevalainen, *Enzyme Microb. Technol.* 3:153–157 (1981), except that Finnfloc was replaced with Solka Floc cellulose. Medium used in fermenter cultivations contained 6% Solka Floc cellulose, 3% distiller's spent grain, 0.5% $KH_2PO_4$, 0.5% $(NH_4)_2SO_4$ and 0.1% struktol. The pH was kept between 4.0 and 4.8 by addition of phosphoric acid or ammonia. Fermentations were carried out at 30° C. Maximum yield of enzymes was obtained in 5 days in laboratory fermentations and in 4 days in 100 liter fermenter scale.

Enzyme Assays

All assays for enzyme activity were carried out from culture supernatant fractions after removing the mycelia by centrifugation for 20 min at 3000 rpm. Endoglucanase activity using hydroxyethylcellulose as substrate (HEC, mittelviskös, Fluka AG 54290, pract. grade) was measured as described in Bailey and Nevalainen, *Enzyme Microb. Technol.* 3:153–157 (1981) and Commission on Biotechnology, International Union of Pure and Applied Chemistry; Measurement of Cellulase Activities, Biochemical Engineering Research Centre, Indian Institute of Technology, Delhi, New Delhi-10016 (1984)) and xylanase activity using birch xylan (Roth No. 7500) as substrate, were measured as described by Bailey et al., *J. Bact.* 23:257–270 (1992). The TCA precipitated proteins were assayed with the method of Lowry et al., *J. Biol. Chem.* 193: 2–65–275 (1951) using bovine serum albumin as standard. Cellobiohydrolase activity against filter paper (filter paper unit, FPU) was measured as described in Commission on Biotechnology, International Union of Pure and Applied Chemistry, Measurement of Cellulase Activities, Biochemical Engineering Research Centre, Indian Institute of Technology, Delhi, New Delhi-10016 (1984)).

ELISA Assay for Endoglucanase I

Endoglucanase I protein concentration in the culture supernatant fractions was determined by a double antibody sandwich ELISA. The assays were performed in 96-well flat bottomed microtiter plates at 370° C. (except were noted). Each step was terminated by washing 3 times with phosphate buffered saline pH 7.2 containing 0.05% Tween 20 and 0.02% sodium azide (PBS/Tween).

The plates were coated with mouse monoclonal antibodies directed against endoglucanase I (anti-EGI antibody EI-2) overnight at 4° C. Unoccupied sites on the plastic surface were blocked with 1% BSA in PBS/Tween for 1 hr. Appropriate dilutions of culture supernatant fractions and purified endoglucanase I were then added and incubated for 2 hrs followed by an incubation with rabbit polyclonal antibodies against endoglucanase I for 2 hrs. Bound rabbit antibodies were detected by incubation with swine polyclonal antibodies against rabbit IgG conjugated to alkaline phosphatase (Orion Diagnostica, Espoo, Finland) for 2 hrs. In an end step p-nitrophenylphosphate (1 mg/ml) was added and the reaction stopped after 30 min at room temperature with 2N NaOH. The developed yellow color was measured photometrically at 405 nm. The concentration of endoglucanase I in culture supernatant fractions was then calculated by comparing their $OD_{405}$ values with a standard dilution curve prepared using purified endolgucanase I and performed at the same time on the same plate.

Fractionation of the Culture Supernatant Fraction by Chromatofocusing

The chromatographic system consisted of a Pharmacia FPLC apparatus equipped with a Mono P HR 5/20 column for chromatofocusing. The resin was stabilized in 25 mM Bistris-HCl buffer, pH 6.5. The crude enzyme mixture produced by *T. reesei* in shake flask culture was diluted with the same buffer to 1 mg/ml protein content. 500 µl enzyme samples were injected into the column and eluted with Pharmalyte/Polybuffer (Pharmacia, 1 ml Pharmalyte® 2.5–5 and 5 ml Polybuffer™ PB 74 in a total 100 ml, adjusted pH to 3.0 with HCl) forming a pH gradient from 6.5 to 3.0. The flow rate was 30 ml/h. Column effluents were collected in 600 µl fractions and the pH and EGI activity were assayed.

EXAMPLE

Cloning, Sequencing and Enhanced Expression of the Trichoderma reesei Endoxylanase II (pI 9) Gene, xln2

In the results presented in this example, the *Trichoderma reesei* xln2 gene coding for the pI 9.0 endoxylanase was isolated from the wild-type strain QM6a. The gene contains one intron of 108 nucleotides and codes for a protein of 223 amino acids in which two putative N-glycosylation target sites were found. Three different *T. reesei* strains were transformed by targeting a construct composed of the xln2 gene with its own promoter to the endogenous cbh1 locus. Highest overall production levels for xylanase were obtained using the *T. reesei* ALK02721, a genetically engineered strain, as a host. Integration into the cbh1 locus was not required for enhanced expression under xln2 promoter.

Materials and Methods

Organisms, plasmids and growth conditions. Plasmids were propagated in *Escherichia coli* strain XL1-Blue (Bullock, W. O., et al., *Bio/Techniques* 5:376–378 (1987)) or in *E. coli* INV1αF' (Invitrogen, San Diego, Calif., USA). The recipient organisms for the xln2 gene were the high cellulase-producing mutants *T. reesei* VTT-D-79125 (Bailey and Nevalainen, *Enzyme Microb. Technol.* 3:153–157 (1981)), ALK02721 and ALK02221. *T. reesei* ALK02221 is a low protease mutant of the strain VTT-D-79125. *T. reesei* ALK02721 is a trpC minus (trpC⁻) UV mutant of VTT-D-79125, in which the cbh2 locus has been replaced with the trpc gene of *Aspergillus nidulans* (Yelton, M. M., et al., *Proc. Natl. Acad. Sci. USA* 81:1470–1474 (1984)). The strain also carries several other integrated copies of the trpC gene.

The plasmids used in this study included pBluescript (Stratagene, San Diego, Calif., USA), pCR1000 (Invitrogen) and pUC19 (Yanish-Perron, C., et al., *Gene* 33:103–119 (1985)). The selectable marker, amdS, came from the plasmid p3SR2 (Kelly and Hynes, *EMBO J.* 4:475–479 (1985)) kindly donated by Dr. M. Hynes. The cbh1 flanking regions were isolated from the *T. reesei* strain ALK02466 (Harkki, A., et al., *Enzyme Microb. Technol.* 13:227–233 (1991)), using plasmid rescue.

*E. coli* cultures were grown at 37° C. overnight in L-broth (Maniatis, T., et al., *Molecular Cloning: A Laboratory Manual*, Cold Spring Harbor Laboratory, Cold Spring Harbor, N.Y. (1982)) supplemented with ampicillin (50 µg/ml) as needed. PD (Potato Dextrose Broth, Difco, Detroit, USA) agar slants were used for growing the Trichoderma strains. For xylanase production, the *T. reesei* strains were grown for seven days in shaker flasks (30° C., 250 rpm) in a cellulase- and xylanase-inducing medium (pH 5.5) containing of 4% whey, 1.5% complex nitrogen source, 1.5% $KH_2PO_4$ and 0.5% $(NH_4)_2SO_3$.

Peptide digestion and amino acid sequencing. Purified xylanase II (Tenkanen, M., et al., *Enzyme Microb. Technol.*

14:566–574 (1992)) from *T. reesei* (VTT-D-79125) was digested with 2% (w/w) trypsin (TPCK-treated, Sigma Chemical Company, St. Louis, Mo., USA) in 1% (w/v) ammonium bicarbonate at 37° C. for 2.5 h. After addition of 3% (w/w) trypsin, incubation was continued overnight (13 h). The peptides were separated using high-performance liquid chromatography (HPLC) with a Rexchrom Prep-5/300 ODS reverse-phase column. Elution was performed at the rate of 1 ml/min in a linear solvent gradient running from 5% (v/v) acetonitrile (ACN) containing 0.1% trifluoroacetic acid (TFA) to 60% (v/v) ACN containing 0.06% TFA in 60 min at 24 ° C. Absorbance at 218 nm was measured. Prior to amino-terminal sequencing, 10 $\mu$g of xylanase II was treated with 1 U of pyroglutamate aminopeptidase (Boehringer Mannheim, Mannheim, Germany) at 37° C. overnight in 100 mM potassium phosphate buffer, pH 8.0, containing 10 mM EDTA and 5 mM DTT. Amino-terminals of the protein and the peptides were sequenced by degrading them in a gas-pulsed-liquid-phase sequencer (Kalkkinen and Tilgmann, *J. Protein Chem.* 7:242–243 (1988)). The released PTH-amino acids were analyzed on-line using narrow-bore reverse-phase HPLC.

DNA manipulation and transformations. Standard DNA methods described by Maniatis, T., et al., *Molecular Cloning: A Laboratory Manual*, Cold Spring Harbor Laboratory, Cold Spring Harbor, N.Y. (1982) were used for the DNA constructions. Plasmid and cosmid DNAs were isolated using Qiagen columns (Diagen GmbH, Düsseldorf, Germany) according to the manufacturer's instructions.

*E. coli* was transformed according to Hanahan, D., *J. Mol. Biol.* 166:557–580 (1983), and *T. reesei* strains by the method of Penttilä, M., et al., *Gene* 61:155–164 (1987) with the following modifications: the protoplasts were treated by heat shock (Berges and Barreau, *J. Gen. Microbiol.* 135:601–604 (1989)) before transformation, 25% PEG$_{6000}$ was replaced with 60% PEG$_{4000}$ and the transformation was performed at room temperature instead of that on ice. The transformants were purified through conidia on selective acetamide-CsCl plates (Penttilä, M., et al., *Gene* 61:155–164 (1987) before transferring them to PD slants.

RNA isolation, *T. reesei*. VTT-D-79125 was cultured in a fermentor in xylanase-inducing medium for three days. The mycelia were harvested, frozen and ground into a fine powder under liquid nitrogen. Total RNA and, subsequently, mRNA were isolated using Proteinase K digestion, phenol extractions and oligo dT-cellulose purification, as described by Bartels and Thompson, *Nucleic Acid Res.* 11:2961–2978 (1983). The mRNA obtained was size-fractionated using DMSO-sucrose gradient centrifugation (Boedtker, H., et al., *Biochemistry* 15:4765–4770 (1976)).

Cloning of xylanase II cDNA. The first strand of cDNA was prepared from 1 $\mu$g of mRNA by using the cDNA synthesis kit (Boehringer Mannheim), replacing the oligo dT-primer with a hybrid dT$_{17}$-adapter primer (5' GAC-TCG-AGA-ATT-CAT-CGA-dTI$_{17}$ ') [SEQ ID No.:5:]. This cDNA was used as a template for polymerase chain reaction (PCR) amplification (Frohman, M. A., "Race: Rapid Amplification of cDNA Ends," in *PCR Protocols*, Innis, M. A., et al., eds., Academic Press Inc., San Diego, Calif., pp. 28–38 (1990)) directed by a gene specific primer (sense 5' GG(A/C/G)-TGG-CA(A/G)-CCN-GGN-ACN-AA 3') [SEQ ID No. :6:] deduced from a peptide sequence and by the adapter primer (5' GAC-TCG-AGA-ATT-CAT-CGA 3') [SEQ ID No.:7:]. The 100 $\mu$l PCR reaction mixture contained 5 $\mu$l of 1:25 diluted cDNA, 100 pmol of each primer, 5 $\mu$M dNTP, 1 x PCR buffer and 1.5 units of Taq DNA polymerase (Boehringer Mannheim). Amplification in a programmable thermal controller (M.J. Research Inc.) comprised 30 cycles at 95° C. for 1 min, at 55° C. for 1 min and at 72° C. for 2 min. After the last cycle, the elongation period was extended to 10 min. The PCR fragments obtained were cloned using a TA Cloning kit (Invitrogen) according to the manufacturer's instructions and verified by sequencing.

Isolation of the xln2 gene. A genomic cosmid library (Suominen et al., MGG, In press) of *T. reesei* QM6a (Mandels and Reese, *J. Bacteriol.* 73:269–278 (1957)) was screened by hybridization with a xylanase II PCR probe according to the supplier's instructions (Boehringer Mannheim, Germany).

Nucleotide sequencing. The templates for nucleotide sequencing were generated by unidirectional deletions according to the manufacturer's instructions for the pBluescript Exo/Mung DNA sequencing system (Stratagene). DNA was sequenced in both directions by using ABI (Applied Biosystems, Foster City, USA) kits based on fluorescence-labelled T7 and T3 primers and a Taq cycle sequencing method according to the supplier's instructions. Sequencing reactions were analysed on an ABI 373A Sequencer.

Enzyme and protein assays. Enzymes were assayed from the culture supernatants after removing the mycelia. Xylanase activity was measured, using birch xylan (Roth 7500) as substrate, by the method described by Bailey, M. J., et al., *J. Biotechnol.* 23:257–270 (1992). Production of cellobiohydrolase I (CBHI) protein was detected by Western blot or dot blot methods using the CBHI specific monoclonal antibodies CI-89 or CI-261 (Aho, S., et al., *Eur. J. Biochem.* 200:643–649 (1991)).

Results

Peptide sequences

Several tryptic peptides from the purified endoxylanase II were obtained and directly sequenced (see FIG. 3A and 3B for peptide sequences). However, no amino-terminal sequence for the native protein was detected, suggesting that it was blocked. After treatment with pyroglutamate aminopeptidase, an amino-terminal sequence of (Q)-X-Ile-Gln-Pro-Gly-Thr-Gly-Tyr-Asn [SEQ ID No.:8:] was obtained. The first amino acid (X) of the pyroglutamate aminopeptidase treated sample could not be determined without ambiguity because of confounding peaks in the HPLC chromatogram.

Cloning of *T. reesei* xln2 cDNA

The accumulation of xylanase II specific mRNA in *T. reesei* cultures was determined by Northern hybridization using a nucleotide oligomer deduced from the peptide (marked with a double underline in FIG. 3) sequence as a probe. The results indicated that the xylanase II mRNA was most abundant in mycelia grown for three days and that the size of the xylanase II specific mRNA was about 0.7 kb (data not shown).

The xylanase II specific oligomer (see above) primer and an unspecific dT-adapter primer were used to amplify the xylanase sequence from the first strand of cDNA. The amino acid sequence deduced from the nucleotide sequence of the subclone pALK564, containing the longest of the fragments synthesized in a PCR reaction, contained several of the xylanase II peptide sequences obtained by direct sequencing. This confirmed that the PCR clone coded for xylanase II.

Isolation and nucleotide sequence of the xln2 gene of *T. reesei*

Figure 2:
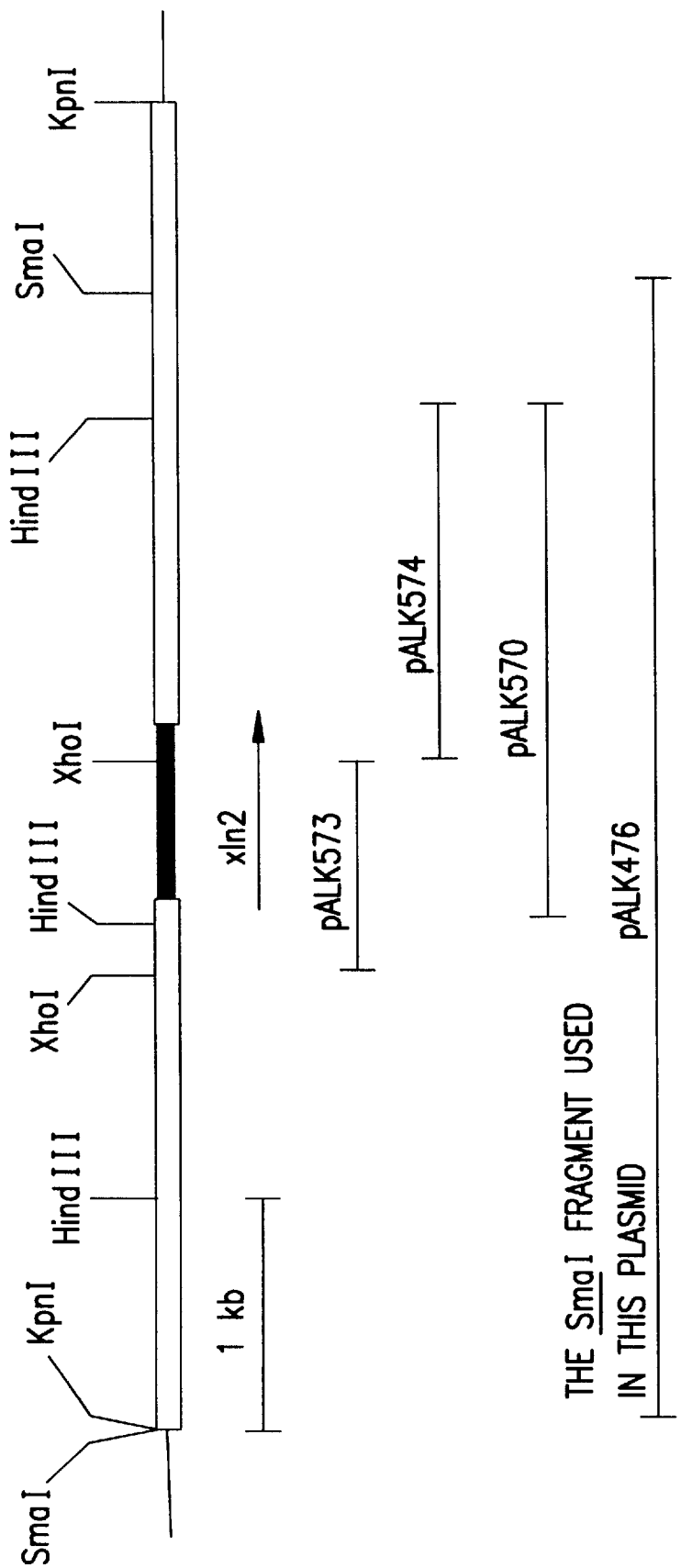
FIG. 2 shows the restriction map of the 5.7 kb (KpnI) insert of pALK475 (DSM 11020, DSMZ-Deutsche Sammlung von Mikroorganismen und Zellkulturen GmbH Braunschweig, Germany; deposited Jun. 21, 1996). The location of xln2 gene is marked with an arrow. The inserts in the subdlones pALK573, pALK574, pALK570 and pALK476 are shown by separate lines. The SmaI site at the 5' end of the fragment is derived from the polylinker of pUC19.

Four clones were isolated from a genomic cosmid library of *T. reesei* through hybridization with the insert of pALK564 (insert=PCR-synthesized xln2 cDNA). A subclone, pALK475, containing a hybridizing 5.7 kb KpnI fragment from the cosmid clone in the pUC19 vector was analysed by restriction mapping (FIG. 2). The hybridizing 2.3 kb HindIII, 1.5 kb HindIII/XhoI and 1 kb XhoI fragments from pALK475 were subcloned and partially sequenced to reveal the xln2 gene.

The nucleotide and deduced amino acid sequences of the xln2 gene are shown in FIGS. 3A and 3B. Sequence resembling the TATA box was found in the DNA at a distance of −140 nucleotides from the ATG, (FIGS. 3A and 3B). The primary translation start site (ATG), flanked by the highly conserved consensus sequence 5' CA C/A A/C ATG 3' found in filamentous fungi and other eukaryotes (Ballance, J. D., "Transformation systems for filamentous fungi and an overview of fungal gene structure," in *Molecular Industrial Mycology: Systems and Applications for Filamentous Fungi*, Leon and Berka, eds., Marcel Dekker Inc., New York, pp. 1–29 (1991)), is 99 nucleotides upstream of the codon for the determined N-terminal amino acid of xylanase II. The xln2 gene codes for a protein of 223 amino acids. In this protein, the N-terminal, obtained by direct peptide sequencing, is preceded by 33 amino acids. This preprosequence contains a putative signal peptidase cleavage site (von Heijne, G., *Nucl. Acid Res.* 14:4683–4690 (1986)) between Ala19 and Ala20. Comparison of the genomic sequence with the cDNA sequences revealed one intron of 108 nucleotides. This indicates that the mature xylanase II protein consists of 190 amino acids and has a calculated molecular weight of 20.8 kDa. This is in good agreement with the 20 kDa obtained for purified xylanase II (Tenkanen, M., et al., *Enzyme Microb. Technol.* 14:566–574 (1992)). Sequence analysis also revealed two putative targets (Asn-X-Ser/Thr where X is not Pro; Gavel and von Heijne, *Protein Engineering* 3:433–442 (1990)) for N-glycosylation (Asn38 and Asn61 of the mature protein).

Construction of pALK476

Figure 4:
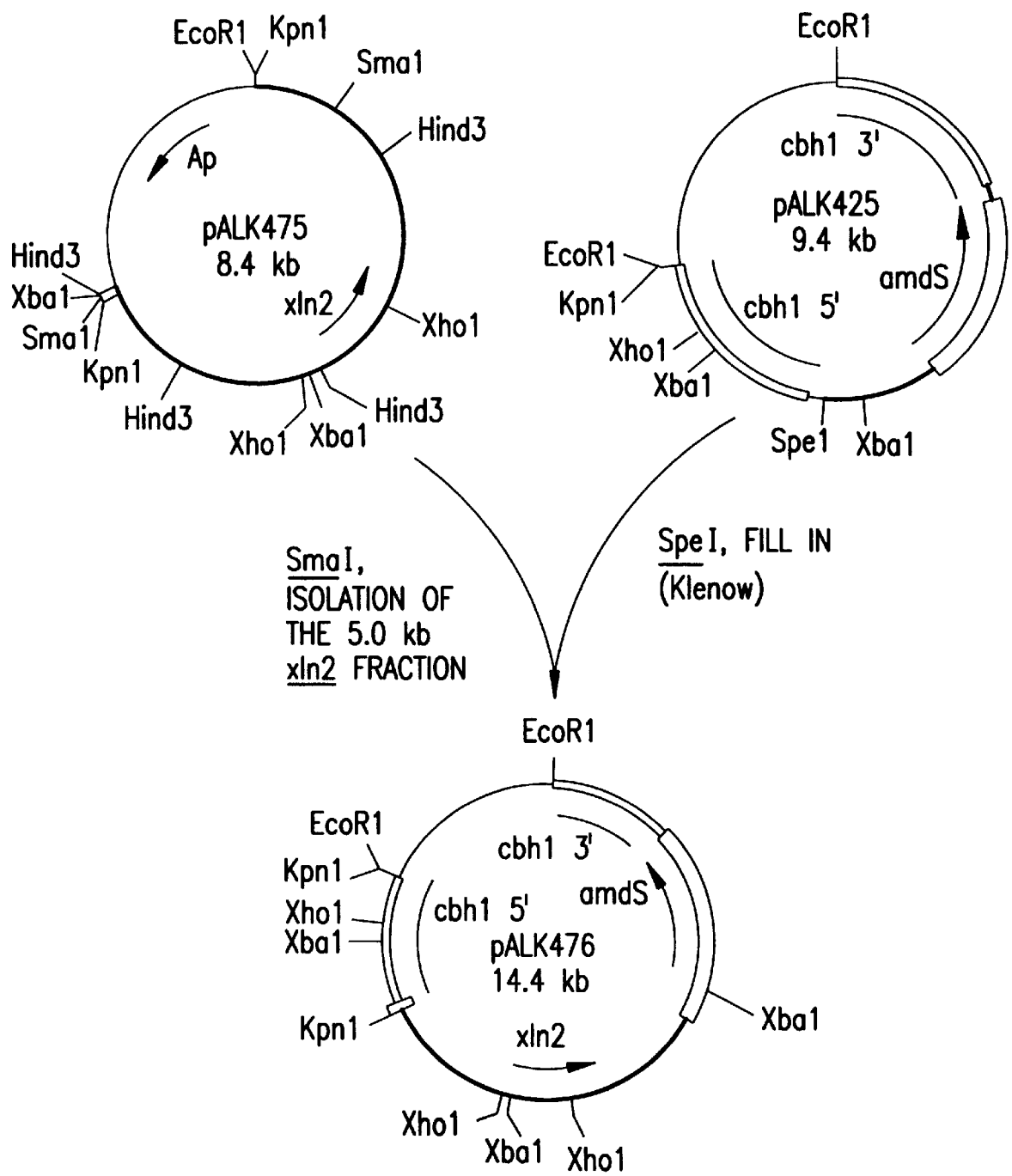
FIG. 4 shows plasmid pALK476, a plasmid for targeting the xln2 gene to the cbh1 locus. The xln2 gene is under the control of its own promoter.

Construction of the plasmid pALK476 is shown in FIG. 4. This plasmid is useful for targetting the xln2 gene to the cbh1 locus. Expression of the xln2 gene is under the control of its native promoter. The 5.0 kb SmaI fragment from the plasmid pALK475 (FIG. 2), containing the xln2 gene and promoter (2.3 kb of the gene's upstream area), was ligated to SpeI site (filled in with Klenow) of the plasmid pALK425.

Enhanced expression of xln2 in *T. reesei*

Figure 5:
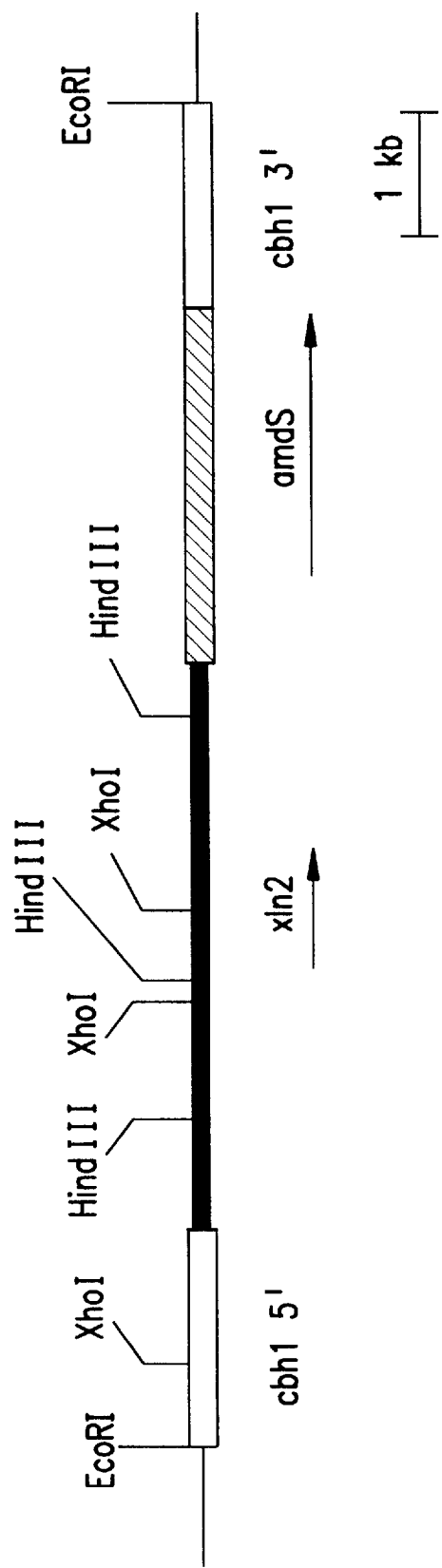
FIG. 5 shows the pALK476 fragment used in the transformations. The 1.9 kb cbh1 5'-flanking region (ScaI-EcoRI) is from 2.2 kb upstream of the cbh1-coding region, the 1.8 kb 3'-region (BamHI-EcoRI) is from 1.4 kb downstream of the end of the cbh1-coding region. The amdS gene was from p3SR2 (3.1 kb SpeI-XbaI fragment) and the xln2 gene was from pALK475 (5.0 kb SmaI fragment, see FIG. 2). The promoter area of the xln2 gene in the fragment is 2.3 kb in size.

To enhance xylanase expression in *T. reesei*, three strains, VTT-D-79125, ALK02221 and ALK02721, differing in their enzyme production profiles, were transformed with the EcoRI fragment from the plasmid pALK476 (FIG. 4). The expression cassette containing the xln2 gene with its own promoter (FIG. 5) was targeted to the cbh1 locus, using the cbh1 flanking regions.

Transformants, 57 from *T. reesei* VTT-D-79125, 42 from ALK02221 and 53 from ALK02721 transformations, were purified and grown in shake flask cultures in xylanase-inducing conditions. Xylanase production was measured as birch xylan degrading activity in the culture supernatants. The transformants were tested for CBHI protein production to determine the targeting frequencies to the cbh1 locus and to distinguish between transformants in which the xln2 expression cassette was located at the cbh1 locus and those in which it was integrated elsewhere. Replacement of the cbh1 locus by the xln2 expression cassette results in a CBHI negative (CBHI⁻) phenotype which was detected in Western blots and dot blots by using a CBHI specific monoclonal antibody. Targeting efficiency to the cbh1 locus, determined as the CBHI⁻ phenotype was high in each case: 67%, 62% and 58% in transformants of VTT-D-79125, ALK02221 and ALK02721, respectively.

Figure 6:
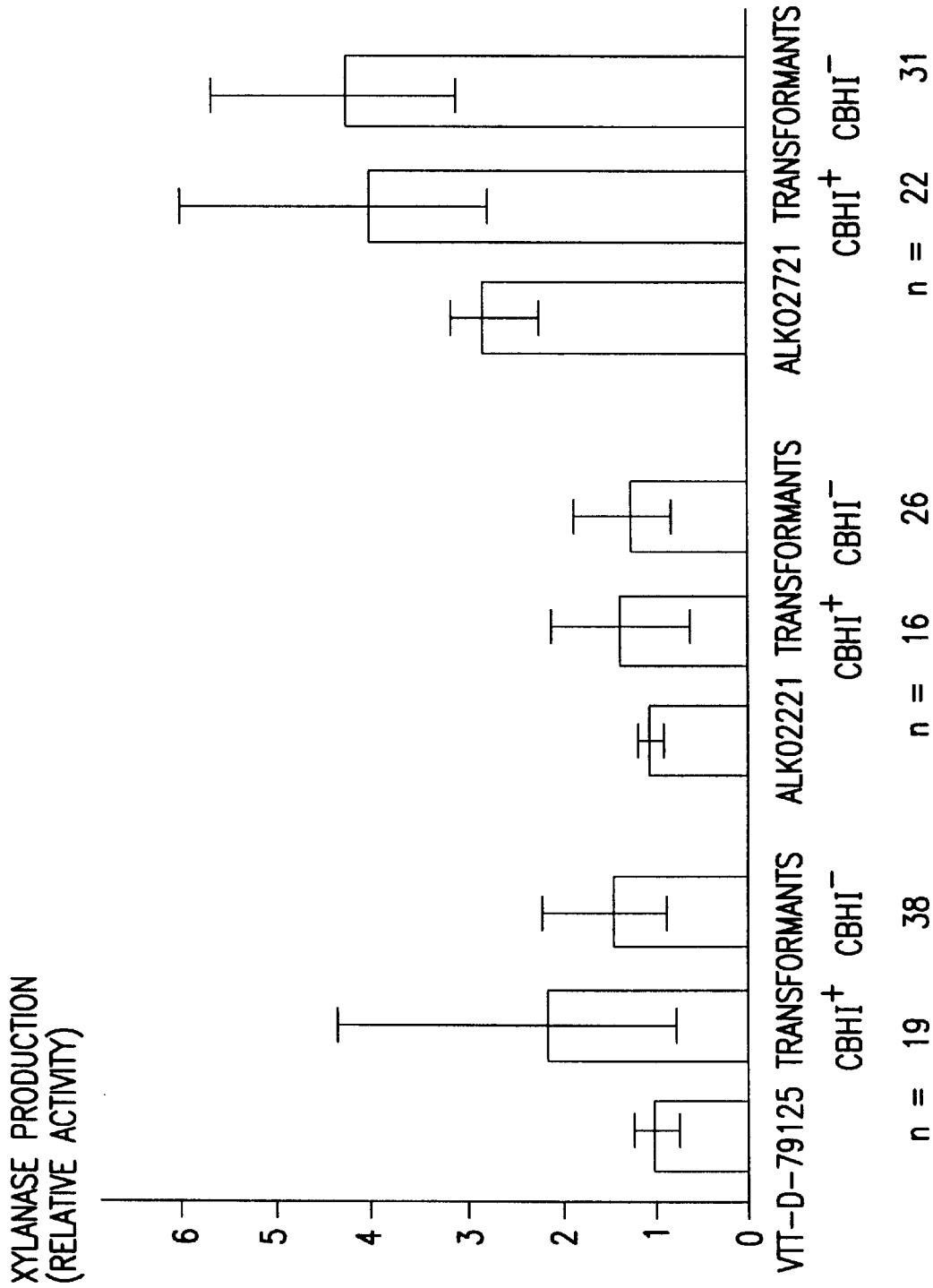
FIG. 6 shows XYLII transformants/pALK476 (xln2 gene with its own promoter) the relative xylanase production levels of the transformants are calculated relative to that of *T. reesei* VTT-D-79125. The columns show the mean values and the range of production levels among the transformants of each host strain. One flask of each transformant was grown. The numbers of transformants tested were (CBHI$^{+/}$-): *T. reesei* VTT-D-79125 19/38, ALK02221 16/26 and ALK02721 22/31.

FIG. 6 shows the relative xylanase activities of the transformants grouped according to their CBHI$^{+/-}$ phenotype. Increase in the xln2 copy number resulted in increased production of xylanase activity in both CBHI⁻ and CBHI⁺ transformants of each strain. The best transformants yielded about twofold (*T. reesei* ALK02221 and ALK02721) to 4.5-fold (*T. reesei* VTT-D-79125) xylanase activity compared with the respective host strains. The highest activities (nkat/ml) were obtained by using *T. reesei* ALK02721 as a host. The best transformants of *T. reesei* ALK02221 produced less than half the activity obtained with the best transformants of the two other strains. There was little difference in xylanase activity between the CBHI⁺ and CBHI⁻ phenotype in the transformants of *T. reesei* ALK02221 and ALK02721 (FIG. 6). Among the *T. reesei* VTT-D-79125 transformants, those with the CBHI⁺ phenotype were on average better producers of xylanase.

To evaluate the effect of the genetic background on the expression of the xln2 gene in the three hosts, the relative increase in xylanase activity in the CBHI⁻ transformants was calculated. The CBHI⁻ transformants were used to eliminate any effects of differences in the site of integration on gene expression. Within each host strain, most of the CBHI⁻ transformants (42–86%, Table 1) exhibited similar levels of increase in xylanase activity. Most of the transformants excluded from this comparison produced higher xylanase activities. From this we conclude that it is likely that the transformants shown in Table 1 have one extra copy of xln2 at the cbh1 locus, in addition to the natural xln2. The average xylanase activity of these transformants and the average increase compared with the host strain are shown in Table 1. The average increase ranged, depending on the host strain, from about 600 nkat/ml (ALK02221) to about 2700 nkat/ml (ALK02721).

TABLE 1

Relative Increase in Xylanase Production in a Chosen Set of CBHI⁻ transformants

| Strain | Average Activity (nkat/ml) | | Average Increase in activity (nkat/ml) |
|---|---|---|---|
| VTT-D-79125 | 3700 | (+/−20%) | |
| transformants (50%) | 5100 | (+/−20%) | 1400 |
| ALK02221 | 3800 | (+/−10%) | |
| transformants (85%) | 4400 | (+/−15%) | 600 |
| ALK02721 | 10200 | (+/−15%) | |
| transformants (42%) | 12900 | (+/−10%) | 2700 |

* The proportion (%) of CBHI⁻ transformants apparently having an extra copy of xln2 is shown in the parentheses.

Discussion

There are several reports on molecular cloning of bacterial xylanases (e.g., Ghangas, G. S., et al., *J. Bacteriol.* 171:2963–2969 (1989); Lin and Thomson, *Mol. Gen. Genet.* 228:55–61 (1991); Shareck, F., et al., *Gene* 107:75–82 (1991); Whitehead and Lee, *Curr. Microbiol.* 23:15–19 (1991)). Recently, reports on the cloning of xylanases of filamentous fungi have also been published, including those of *Aspergillus tubigensis* (van den Broeck, N., et al., "Cloning and Expression of Xylanase Genes from Fungal Origin," EP 0 463 706 A1 (1992)), A. niger var. awamori (Maat, J., et al., "Xylanases and Their Application in Bakery," in *Xylans and Xylanases*, Visser, J., et al., eds., Elsevier Science, Amsterdam, pp. 349–360 (1992)), A. kawachii (Ito, K., et al., *Biosci. Biotechnol. Biochem.* 56:906–912 (1992))

and *T. reesei* (Suominen, P., et al., "Genetic Engineering of Trichoderma reesei to Produce Suitable Enzyme Combinations for Applications in the Pulp and Paper Industry," in *Biotechnology in Pulp and Paper Industry*, Kuwahara and Shimada, eds., Uni Publishers Co., Ltd., Tokyo, Japan, pp. 439–445 (1992); Törrönen, A., et al., Bio/Technology 10: 1461–1465 (1992)). The genes for *T. reesei* xylanase II (pI 9) cloned of the wild-type strain QM6a by us (see also Suominen, P., et al., "Genetic Engineering of *Trichoderma reesei* to Produce Suitable Enzyme Combinations for Applications in the Pulp and Paper Industry," in *Biotechnology in Pulp and Paper Industry*, Kuwahara and Shimada, eds., Uni Publishers Co., Ltd., Tokyo, Japan, pp. 439–445 (1992)) and of the mutant strain RutC-30 by Törrönen, A., et al., *Bio/Technology* 10:1461–1465 (1992) were not completely identical. The main differences were between the sequences of pre-propeptides thus suggesting differences in the signal processing.

According to our results, the xln2 gene of *T. reesei* contains one long intron of 108 bp. The introns in filamentous fungi are usually smaller, around 50 bp in length, but, as shown by Vanhanen et al., *Curr. Genet.* 12:181–186 (1989) for the gene of 3-phosphoglycerate kinase in *T. reesei*, they can also be considerably longer. The fairly long pre-prosequence (33 amino acids) of the xln2 gene contains one primary cleavage site for the signal peptidase. This is compatible with a signal sequence of 19 amino acids followed by a propeptide of 14 amino acids, which may be post-translationally cleaved from the mature protein. Törrönen, A., et al., *Bio/Technology* 10:1461–1465 (1992) suggested that the signal pre-propeptide of the xylanase II (pI 9) of *T. reesei* RutC-30 consists of 32 amino acids and has two putative signal peptidase cleavage sites very close to the translation start site (5 and 11 amino acids, respectively). This would result in rather short signal sequences. Two-step protein processing, similar to what is proposed here for the xylanase II, has been shown to occur with *A. niger* glucoamylase (Innis, M. A., et al., *Science* 228:21–26 (1985)) and suggested to occur with *T. reesei* cellobiohydrolase II (Teeri, T., et al., *Gene* 51:43–52 (1987)). Overall structure similar to *T. reesei* xln2 is found in the *A. niger* xylanase gene (van den Broeck, N., et al., "Cloning and Expression of Xylanase Genes from Fungal Origin," EP 0 463 706 A1 (1992)) but not, for instance, in the *A. kawachii* xylanase A gene, which contains nine introns and codes for a larger (32.7 kDa) protein (Ito, K., et al., *Biosci. Biotechnol. Biochem.* 56:906–912 (1992)).

Production of xylanase could be increased in three *T. reesei* strains by increasing the copy number of he xln2 gene. Of these strains, *T. reesei* VTT-D-79125 is a high cellulase-producing mutant and ALK02721 was used as a host because of its pre-existent high xylanase production. We also wanted to produce xylanase in the low-protease *T. reesei* ALK02221, both to obtain a xylanase product with a low protease background and to increase the relative amount of xylanase in the culture medium.

The highest increase in xylanase activity ranged from about twofold to over fourfold compared with the respective host strain. Xylanase activities of the transformants of the low-protease strain ALK02221 and those of the genetically engineered host ALK02721 were independent of whether the xln2 gene was integrated into the cbh1 locus or elsewhere in the genome (CBHI$^{+/-}$ phenotype). For *T. reesei* VTT-D-79125 transformants, integration of the xln2 gene elsewhere (CBHI$^+$ phenotype) than into the cbh1 locus seemed to result in higher enzyme yield. These observations are somewhat contradictory to those of Harkki, A., et al., *Enzyme Microb. Technol.* 13:227–233 (1991), who suggested that for optimal expression the expression cassette would require its integration into the cbh1 locus. It should be noted, however, that in the present study the xln2 promoter was used for expression instead of the cbh1 promoter as done by Harkki, A., et al., *Enzyme Microb. Technol.* 13:227–233 (1991) with egl1 cDNA. This indicates that the cbh1 locus may not be the best environment for expression under the xln2 promoter.

The genetic background seemed to have a significant effect on xln2 expression, despite the fact tat the strains *T. reesei* ALK02221 and ALK02721 originate from kT-D-79125. The increase of xylanase production was highest in the transformants of the strain *T. reesei* ALK02721 (2700 nkat/ml) which also had the highest xylanase activity. The expression of one additional copy of xln2 ;varied over fourfold depending on the host (Table 1).

EXAMPLE 2

Increased production of XYLII: xln2 gene fused to the cbh1 promoter

Figure 7:
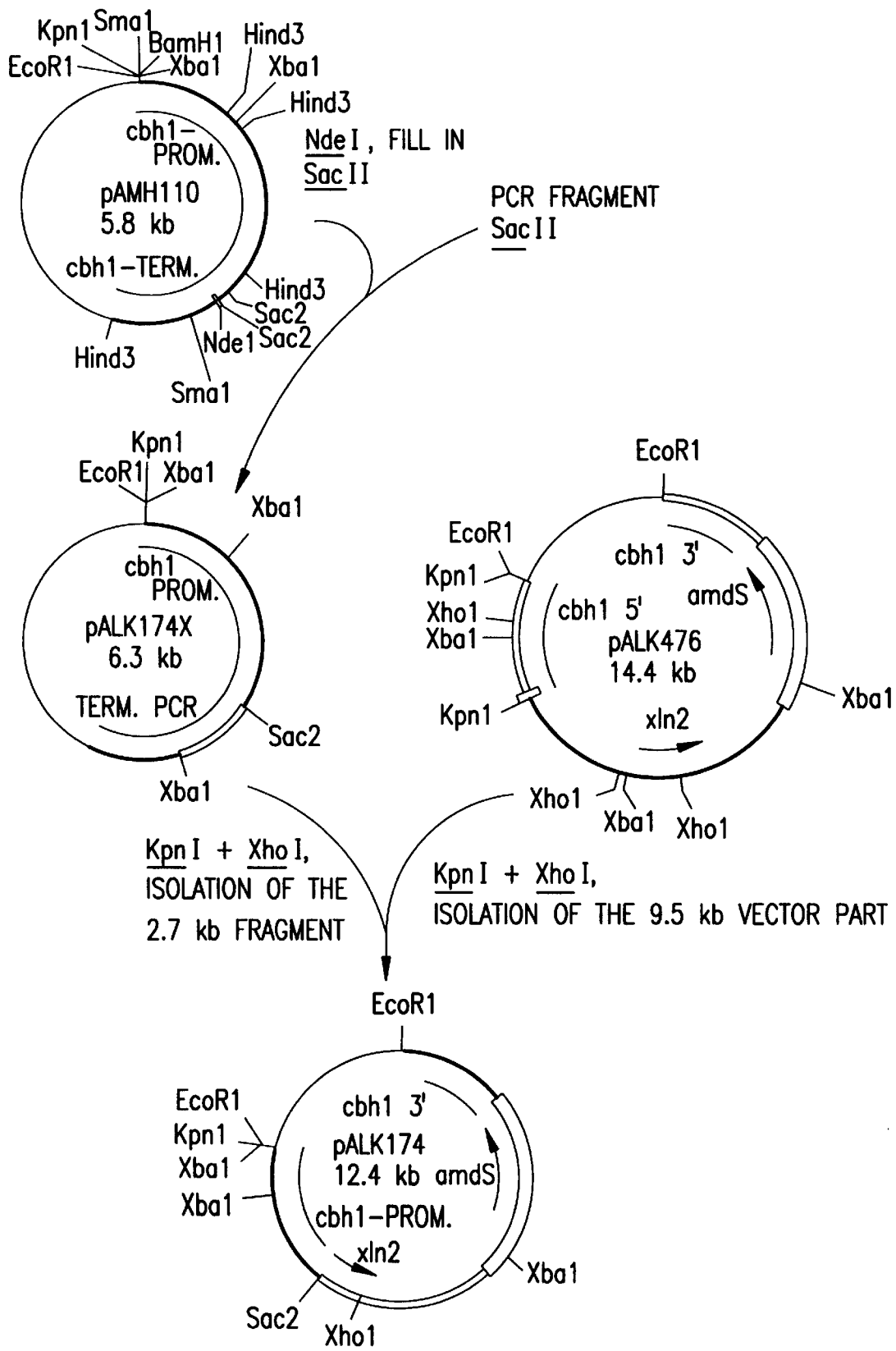
FIG. 7 shows the construction of pALK174 (xln2 gene is fused to the cbh1 promoter). Only the relevant restriction sites are shown.

Construction of pALK174 and transformation of three *Trichoderma reesei* strains Construction of pALK174 is shown in FIG. 7. First, a 674 bp PCR fragment containing an exact fusion of the cbh1 promoter to the xln2 signal sequence (and xln2 gene to the internal XhoI site) was synthesized Oby using plasmid pALK475 (FIG. 2) as a template. The oligonucleotides used were as shown below: 5'-primer contained the end of the cbh1 promoter and the sequence of the beginning of the putative xln2 signal sequence, 3'-primer had sequence from the xln2 gene including the gene's internal XhoI site (see the pALK476 map, FIG. 5 or the xln2 sequence).

5'-primer (39-mer) [SEQ ID No.:11:]:

5'- C AAC CGC GGA CTG CGC ATC ATG GTC TCC TTC ACC TCC CT
        SacII                     beginning of the putative
  end of the cbh1 promoter        xln2 signal sequence 3'-primer (26-mer) [SEQ ID No.:12:]:

5'-GGG AGC CGC TCG AGC GGT GGT TGC GG
               XhoI
           xln2 sequence The 100 μl PCR reaction contained in PCR buffer (10 mM Tris pH 8.3, 50 mM KCl, 1.5 mM MgCl$_2$, 0.01% gelatin, w/v) 50 pmol of each primer, 10 ng of the template DNA, 0.2 mM dNTP and 2U of Taq-polymerase (Boehringer Mannheim). The reaction conditions were: denaturation 1 min. at 95° C., annealing 1 minute at 60° C., extension 2 minutes at 72° C. for 30 cycles, final extension was 9 minutes.

The PCR fragment was purified by using the Mermaid® kit (BIO 101 Inc., La Jolla, Calif., USA). After treating it with the T4 DNA polymerase, it was cut with SacII for fusion to the cbh1 promoter.

The plasmid pAMH110, containing the cbh1 promoter, was cut with NdeI (filled in by Klenow) and SacII. The PCR fragment described above was ligated to the digested pAMH1 10 (pALK174X). The fusions and the sequence synthesized by PCR were ensured by sequencing. The plasmid pALK174 was constructed by replacing the xln2 promoter in pALK476 by the cbh1 promoter: the 2.9 kb KpnI-AoI fragment from the plasmid pALK174X, containing the cbh1 promoter fused to the xln2 gene and xln2 sequence to the internal XhoI, was ligated to the isolated vector containing fragment of pALK476, after cutting pALK476 with KpnI and XhoI.

The plasmid pALK174 contains, in addition to the amdS and cbh1 3'-areas as in pALK476 (FIG. 4), the xln2 gene, fused to the cbh1 promoter and 1.9 kb terminator (3'-area) of the xln2 gene.

The 9.7 kb EcoRI fragment (expression cassette free from the vector sequences) was used to transform three Trichoderma strains, VTT-D-79125, ALK02221 and ALK02721. The strains, transformation method and methods for purification, analyzing and growing the transformants were as described above and in Example 6.

2.2 Production of xylanase by the pALK174 transformants

Figure 8:
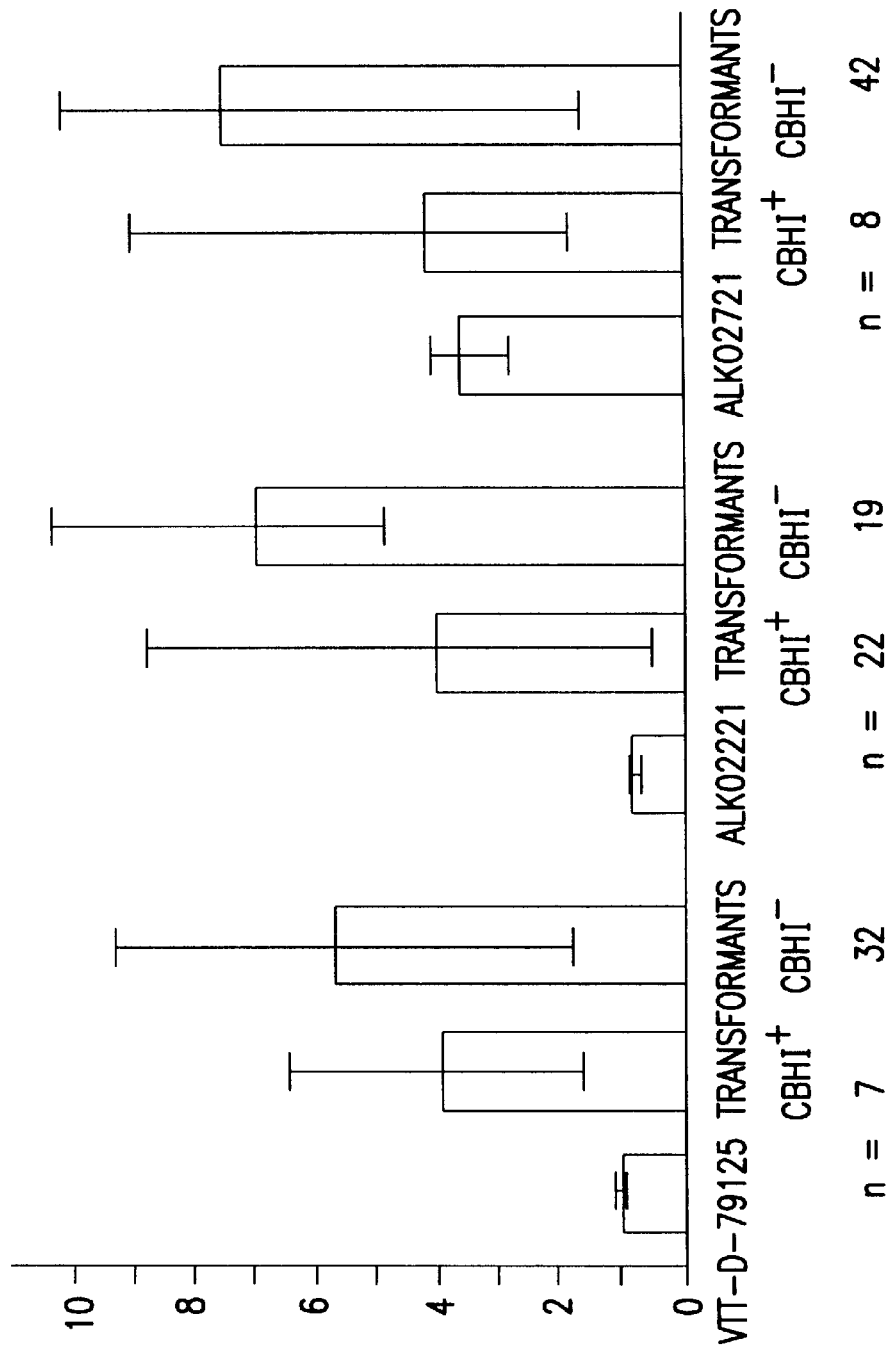
FIG. 8 shows the relative increase in production of xylanase activity in XYLII/pALK174 transformants, (xln2 under the control of the cbh1 promoter).

VTT-D-79125, ALK02221 and ALK02721 transformants, 39, 41 and 50, respectively, were purified and grown to measure the xylanase activities produced. The targeting frequencies to the cbh1 locus were, measured by using dot blot method and a CBHI specific monoclonal antibody (as in Example 4) 82, 46 and 84%, respectively. The production of xylanase activity, shown as relative activity compared to the activity produced by VTT-D-79125, of the CBHI+ and CBHI– transformants is shown in the FIG. 8. The columns show the mean values and the range of production levels among the transformants of each host strain. One flask of each transformant was grown. The xylanase activity was determined from the culture supernatants as described in Example 3 (cloning of xln1).

High production of xylanase was obtained in transformants of all the three Trichoderma strains. The best VTT-D-79125 and ALK02221 transformants produced about 10 times the amount of xylanase activity compared to their host strains. The best ALK02721 transformants produced about the same amount of xylanase activity as the best VTT-D-79125 and ALK02221 transformants and the increase compared to the host was over three fold. In average, the CBHI– transformants were better producers than those with the CBH+ phenotype. Naturally, in the CBHI– transformants the cellulolytic activity has decreased because of the deletion of the cbh1 gene.

The production levels of xylanase, when pALK174 construction was used, were higher compared to those obtained by using pALK476 (xln2 under the control of its own promoter, see Example 1).

EXAMPLE 3

Structure of the Endoxylanase I, xln1, Gene of Trichoderma reesei

In this example, the cloning of the *T. reesei* gene xln1 which codes for the low pI (5.5) endoxylanase I is presented.

Materials and Methods
Bacterial strains and plasmids

The plasmids used in this study were pBluecscript (Stratagene, San Diego, Calif., USA) and pCR1000 (Invitrogen, San Diego, Calif., USA). The plasmids were propagated in *Escherichia coli* strain XLI-Blue (Bullock, W. O. et al., *Bio/Techniques* 5:376–378 (1987)) or in *E. coli* INVLαF' (Invitrogen). *E. coli* cultures were grown at 37° C. overnight in L-broth (Maniatis, T. et al., *Molecular Cloning: A Laboratory Manual* (Cold Spring Harbor Laboratory, Cold Spring Harbor, N.Y.) (1982)) supplemented with ampicillin (50 μg/ml) as needed.

Peptide digestion and amino acid sequencing

Purified xylanase I (Tenkanen, M. et al., *Enzyme Microb. Technol.* 14:566–574 (1992)) from *T. reesei* (VTT-D-79125; Baily, M. J., Nevalainen, K. H. M., *Enzyme Microb. Technol.* 3:153–157 (1981)) was digested with 2% (w/w) trypsin (TPCK-treated, Sigma Chemical Company, St. Louis, Mo., USA) in 1% (w/v) ammonium bicarbonate at 37° C. for 2.5 h. After addition of 3% (w/w) trypsin to the sample, incubation was continued over night (13 h). The peptides were separated using high-performance liquid chromatography (HPLC) with a Rexchrom Prep-5/300 ODS reverse-phase column. Elution was performed at the rate of 1 ml/min in a linear solvent gradient running from 5% (v/v) acetonitrile (ACN) containing 0.1% trifluoroacetic acid (TFA) to 60% (v/v) ACN containing 0.06% TFA in 60 min at 24° C. Absorbance at 218 nm was measured. Amino terminals of the protein and the peptides were sequenced by degrading them in a gas-pulsed-liquid-phase sequencer (Kalkkinen, N., and Tilgmann, C., *J. Prot. Chem.* 7:242–243 (1988)). The released PTH-amino acids were analyzed on-line using narrow-bore reverse-phase HPLC.

DNA manipulation and transformations

Standard DNA methods described by Maniatis et al. (Maniatis, T. et al., *Molecular Cloning: A Laboratory Manual* (Cold Spring Harbor Laboratory, Cold Spring Harbor, N.Y.) (1982)) were used for the DNA constructions. Plasmid and cosmid DNAs were isolated using Qiagen columns (Diagen GmbH, Düsseldorf, Germany) according to the manufacturer's instructions. *E. coli* was transformed according to Hanahan (Hanahan, D., *J. Mol. Biol.* 166:557–580 (1983)).

RNA isolation

For RNA isolation, *T. reesei* (VTT-D-79125) was grown in a fermentor in a xylanase-inducing medium at 30° C. for three days (as described hereinfor the isolation of the xln2 gene). The mycelia were ground into a fine powder under liquid nitrogen. Total RNA and mRNA were isolated as described by Bartels and Thompson (Bartels, D., and Thompson, R. D., *Nucleic Acid Res.* 11:2961–2978 (1983)) and size-fractionated using DMSO-sucrose gradient centrifugation (Boedtker, H. et al., *Biochemistry* 15:4765–4770 (1976)).

Cloning of xylanase I cDNA

The synthesis of the first strand of cDNA and the subsequent PCR amplifications were performed as described herein for xln2 except that here an oligomer (5' AA(T/C)-TA(T/C)-GA(T/C)-CA(G/A)-AA(T/C)-TA(T/C)-GA 3') [SEQ ID No.:9:] deduced from the N-terminal sequence of the xylanase I protein was used as the gene-specific primer. The 0.6 kb PCR fragment obtained was subcloned into the pCR1000 vector and sequenced.

Isolation of xln1 gene

A *T. reesei* (QM6a, Mandels, M., Reese, E. T., *J. Bacteriol.* 73:269–280 (1957)) genomic cosmid library was screened with a digoxigenin-labelled PCR fragment of xylanase I cDNA (see Example 1) according to the supplier's instructions (Boehringer Mannheim, Mannheim, Germany). One positive cosmid clone was obtained. A restriction map of the xln1 area of the cosmid was prepared, and a 2.3 kb EcoRI fragment was subcloned into pBluescript (pALK572) for sequencing.

Nucleotide sequencing

The templates for nucleotide sequencing were generated by unidirectional deletions according to the manufacturer's instructions for the pBluescript Exo/Mung DNA sequencing system (Stratagene). DNA was sequenced in both directions by using ABI (Applied Biosystems, Foster City, USA) kits based on fluoresence-labelled T7 and T3 primers and a Taq cycle sequencing method according to the supplier's instructions. Sequencing reactions were analysed on an ABI 373A Sequencer.

Results

Cloning of *T. reesei* xln1 cDNA

The amino-terminal sequence of purified xylanase I was found to be Ala-Ser-Ile-Asn-Tyr-Asp-Gln-Asn-Tyr-Gln-Thr-Gly-Gly-Gln-Val-Ser-Tyr-(Ser)-Pro-(Ser)-Asn-Thr-Gly-Phe-Ser [SEQ ID No.:10:]. Five tryptic peptides were also obtained and directly sequenced (see FIG. 10A–10B for peptide sequences).

Northern hybridization using the oligomer deduced from the xylanase I N-terminal peptide sequence (see above) as a probe indicated that xylanase I mRNA was approximately 0.6 kb in size.

PCR amplification of the first strand of cDNA resulted in a fragment of 0.6 kb. The nucleotide sequence of this DNA when translated into a protein contained all the xylanase I peptide sequences, including the N-terminal (see FIG. 10A–10B). Plasmid pALK563 containing the xln1 cDNA in the TA cloning site of the vector pCR1000 (invitrogen) was deposited on Apr. 19, 1995 at DSMZ-Deutsche Samlung von Mikroorgansmen und Zellkulturen Gmbh, Braunschweig, Germany and given accession no. DSM 9926.

Isolation and nucleotide sequence of the *T. reesei* xln1 gene

Figure 9:
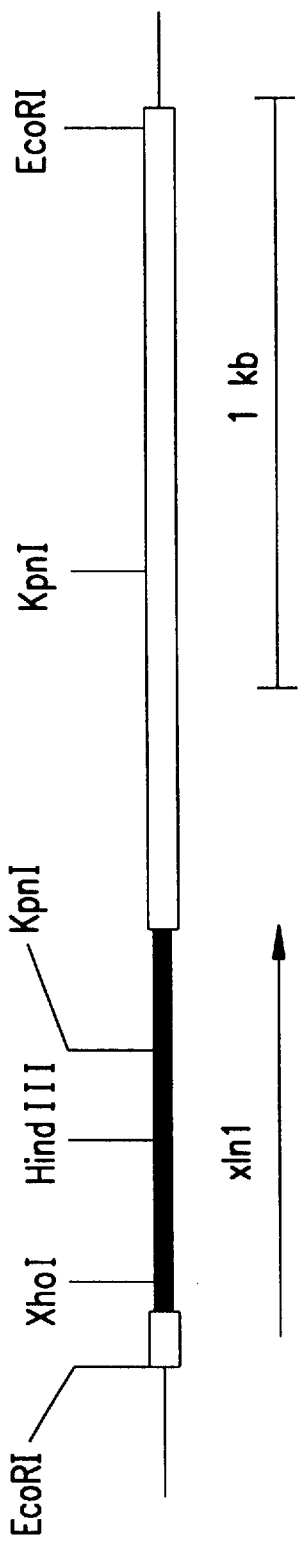
FIG. 9 shows the restriction map of the 2.3 kb EcoRI insert of pALK572. The location of xln1 gene is marked with an arrow.

One positive clone was isolated from a genomic cosmid library of *T. reesei*. The gene for xylanase I (xln1) was found in a 2.3 kb EcoRI fragment of the cosmid (FIG. 9).

The nucleotide sequence of the xln1 gene was determined and is presented in FIG. 10A–10B together with the deduced amino acid sequence. A TATA box was found approximately 90 nt upstream of the putative translation start site. Of the three different putative translation initiation sites preceding the N-terminus of the mature protein, only one was in an environment resembling the highly conserved consensus sequence 5' CA-C/A-A/C-ATG 3' for the translation start site among filamentous fungi (Ballance, J. D., in Leone, S. A., Berka, R. M., eds., *Molecular Industrial Mycology. Systems and applications for filamentous fungi* (Marcel Dekker, Inc., New York), pp. 1–29 (1991)). Thus the gene codes for a protein of 229 amino acids. In this protein, the N-terminal (obtained by direct peptide sequencing, see above) is preceded by a 51 amino acid long signal propeptide containing a primary signal sequence cleavage site (von Heijne, *Nucleic Acids Res.* 14:4683–4690 (1986)) between the amino acids Ala19 and Met20 (FIG. 10). Comparison of the genomic sequence with the cDNA sequence revealed one intron of 62 bp. On the basis of these data, it can be concluded that the mature xylanase I is a protein of 178 amino acids with a calculated molecular weight of 19.1 kDa. This is in good agreement with the 19 kDa obtained for purified xylanase I from *T. reesei* (Tenkanen, M. et al., *Enzyme Microb. Technol.* 14:566–574 (1992)). Unlike the gene of xylanase II (see herein), there is no sequence (Asn-X-Ser/Thr where X is not Pro; Gavel, Y., von Heijne, G., *Protein Engineering* 3:433–442 (1990)) for N-glycosylation.

Comparison of *T. reesei* xylanase I with other xylanases

Both of the proposed catalytic glutamic acids of xylanases (Katsube, Y. et al., *Proc. 2nd Int. Conference Protein Engineering* (Japan Scientific Societies Press, Tokyo), pp. 91–96 (1990); Wakarchuk, W. et al., in Visser J. et al., eds., *Xylans and Xylanases* (Elsevier Science, Amsterdam), pp. 439–442 (1991)) were found in xylanase I by sequence alignment, corresponding to Glu75 and Glu164 of the mature enzyme (FIG. 10A–10B). Table 2 presents a sequence alignment comparison showing the percent identity between different xylanases. The upper right half of the matrix shows the results of an alignment of complete mature sequences, and the lower left half of the sequences between the proposed active site glutamic acids of xylanases.

TABLE 2

Identity % of sequence of alignments between different xylanases expressed as a matrix. Upper right half: mature enzyme sequence alignments. Lower left half: sequence alignments between the two proposed active site glutamic acids.
TI, *T. reesei* xylanase I; TII, *T. reesei* xylanase II; TV, *T. viride* (Yaguchi, M. et al., in Visser, J. et al., eds., Xylans and Xylanases (Elsevier Science, Amsterdam), pp. 149–154 (1992a)); TH, *T. harzianum* (Yaguchi, M. et al., in Visser, J. et al., eds., Xylans and Xylanases (Elsevier Science, Amsterdam), pp. 435–438 (1992b)); AT, *A. tubigensis* (van den Broeck, H. et al., "Cloning and expression of xylanase genes from fungal origin," EP 0 463 706 A1 (1992)); SC, *Schizophyllum commune* (Oku, T. et al. Canadian Fed. Biol. Soc. Annu. Meet. (Quebec City), Abst. 676 (1988)); AK, *A. kawachii* (Ito, K. et al., Biosci. Biotec. Biochem. 56:906–912 (1992), the first 190 amino acids were aligned); BC, *Bacillus circulans* (Yang, R.C.A. et al., Nucleic Acids Res. 16:7187 (1988)); BP, *P. pumilus* (Fukasaki, E. et al., FEBS Lea. 171:197–201 (1984)); BS, *B. subtilis* (Paice, M.G. et al., Arch. Microbiol 144:201–206 (1986)); CA, *Clostridium acetobutylicum* (Zappe H. et al., Nucleic Acids Res. 18:2179 (1990)); SS, Streptomyces sp. 36a (Nagashima, M. et al., Trends Actinomycetologia: 91–96 (1989)).

|     | TI  | TII | TVI | TH  | AT  | SC  | AK  | BC  | BP  | BS  | CA  | SS  |
| --- | --- | --- | --- | --- | --- | --- | --- | --- | --- | --- | --- | --- |
| TI  | 100 | 52  | 52  | 51  | 47  | 42  | 16  | 49  | 40  | 49  | 40  | 43  |
| TII | 60  | 100 | 98  | 94  | 43  | 54  | 17  | 52  | 48  | 52  | 46  | 52  |
| TV  | 60  | 99  | 100 | 94  | 43  | 54  | 25  | 52  | 49  | 52  | 46  | 51  |
| TH  | 57  | 98  | 97  | 100 | 43  | 56  | 19  | 52  | 48  | 52  | 44  | 51  |
| AT  | 62  | 57  | 57  | 58  | 100 | 38  | 17  | 40  | 34  | 40  | 32  | 33  |
| SC  | 52  | 51  | 51  | 52  | 50  | 100 | 15  | 52  | 42  | 52  | 44  | 50  |
| AK  | 20  | 21  | 20  | 21  | 23  | 21  | 100 | 14  | 18  | 14  | 20  | 19  |

TABLE 2-continued

| BC | 53 | 54 | 54 | 56 | 53 | 54 | 16 | 100 | 48 | 100 | 45 | 58 |
|----|----|----|----|----|----|----|----|-----|----|-----|----|----|
| BP | 52 | 57 | 57 | 58 | 47 | 48 | 17 | 59 | 100 | 48 | 71 | 49 |
| BS | 53 | 54 | 54 | 56 | 53 | 54 | 14 | 99 | 60 | 100 | 45 | 58 |
| CA | 52 | 51 | 52 | 52 | 42 | 47 | 19 | 57 | 73 | 58 | 100 | 46 |
| SS | 50 | 53 | 53 | 53 | 46 | 49 | 18 | 64 | 56 | 64 | 52 | 100 |

It can be seen that *T. reesei* xylanase II (pI 9.0) is almost identical with the *T. viride* and *T. harzianum* small, high pI xylanases (Yaguchi, M. et al., in Visser, J. et al., eds., *Xylans and Xylanases* (Elsevier Science, Amsterdam), pp. 149–154 (1992); Yaguchi, M. et al., in Visser, J. et al., eds., *Xylans and Xylanases* (Elsevier Science, Amsterdam), pp. 435–438 (1992)). Alignment of the region between the two active site glutamic acids resulted in most cases in a higher identity than when complete mature sequences where aligned.

Discussion

*T. reesei* produces at least two different xylanases, xylanase I with a pI of 5.5 and xylanase II with a pI of 9, which are small proteins of 19 kDa and 20 kDa, respectively (Tenkanen, M. et al., *Enzyme Microb. Technol.* 14:566–574 (1992)). The corresponding genes xln1 and xln2 have been cloned and described herein. In overall structure the xln1 and xln2 genes are very similar; they are about the same size and both contain only one intron and a long pre-propeptide. However, these two xylanases only show a 54% identity at the DNA level and a 52% identity at the amino acid level. Thus, they are clearly different not only in primary structure but also in enzymatic properties such as tolerance of different pH values or temperatures and kinetic parameters as shown by Tenkanen et al. (Tenkanen, M. et al., *Enzyme Microb. Technol.* 14:566–574 (1992)).

Based on hydrophobic cluster analysis, xylanases have been divided into two subfamilies, F and G (Henrissat, B. et al., *Gene* 81:83–95 (1989)). Subfamily F comprises the high-MW xylanases whereas the low-MW xylanases belong to subfamily G. Henrissat (Henrissat B., in Visser, J. et al., eds., *Xylans and Xylanases*, Proc. Int. Symp. Wageningen (Elsevier, Amsterdam), pp. 97–110 (1991)) suggests that the xylanases of these two subfamilies undergo different folding. The high identity of *T. reesei* xylanases I and II to all other xylanases compared (Table 2), except the *A. kawachii* xylase A, suggests that they too, like the other low-MW xylanases, belong to subfamily G. In the case of the *A. kawachii* xylanase A (Ito, K. et al., *Biosci. Biotec. Biochem.* 56:906–912 (1992)), an identity of only about 20% to the *T. reesei* xylanases was found. This xylanase has a higher MW of 32.7 kDa, and it has been proposed to belong to subfamily F (Ito, K. et al., *Biosci. Biotec. Biochem.* 56:906–912 (1992)).

EXAMPLE 4

Increased production of XYLI by Trichoderma transformed with the construction containing the xln1 gene fused to the cbh1 promoter (pALK807)

Construction of the plasmid pALK807 and transformation of the Trichoderma strain ALK02221

Figure 11:
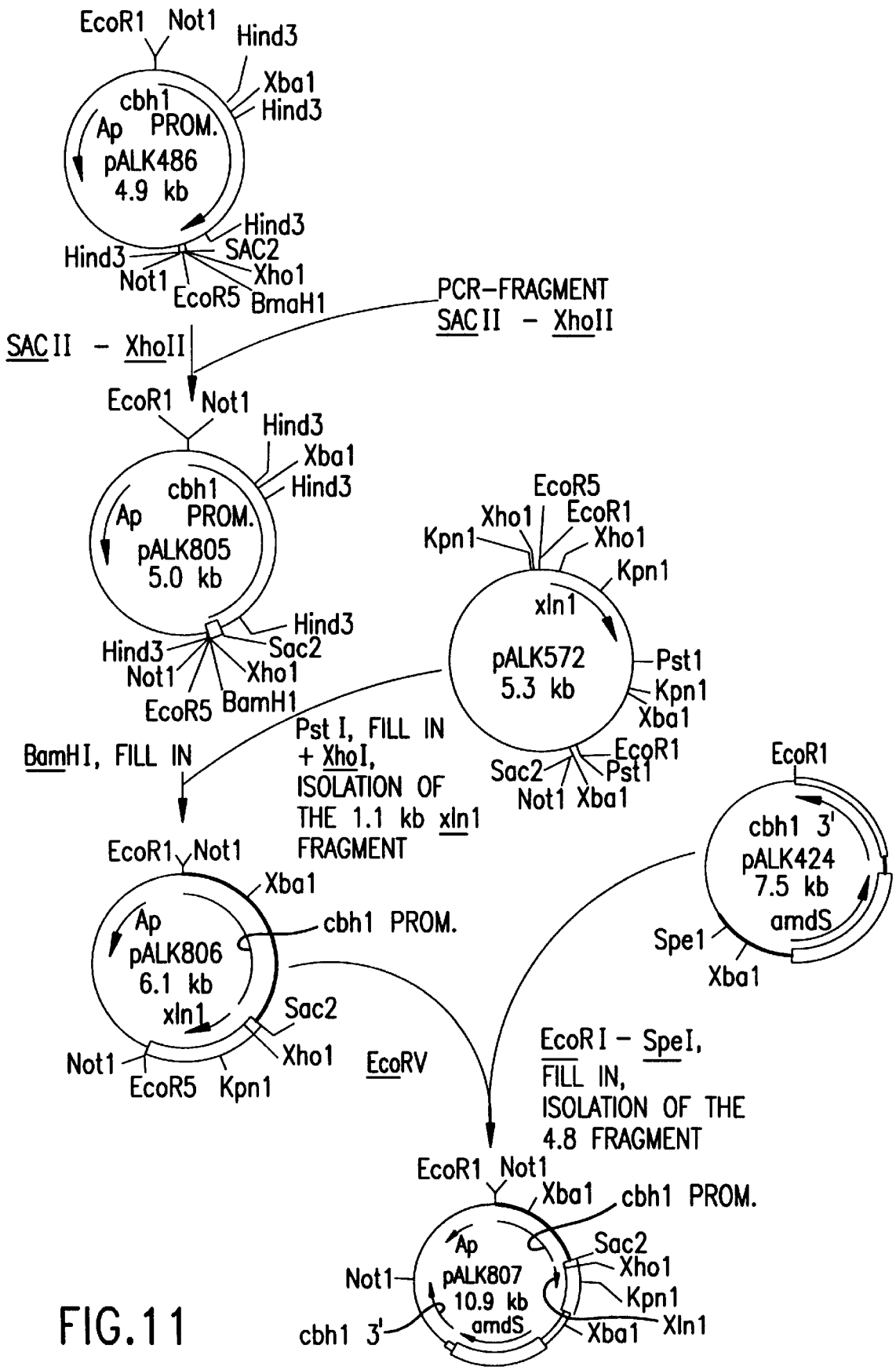
FIG. 11 shows the construction of plasmid pALK807 (xln1 gene is fused to the cbh1 promoter). Only the relevant restriction sites are shown.

The plasmid pALK807 was constructed by using the same strategy as in construction pALK174 (FIG. 11). The 98 bp PCR fragment containing the fusion of the cbh1 promoter to the putative xln1 signal sequence and xln1 sequence to the internal XhoI site (see the pALK572 map in FIG. 2 or the xln1 sequence) was made by PCR using the following oligonucleotides:

5'-primer (39-mer) [SEQ ID No. :13:]:

5'- C AAC CGC GGA CTG CGC ATC ATG GTT GCC TTT TCC AGC CT
       ‾‾‾‾‾‾‾‾
         SacII                    beginning of the putative
    end of the cbh1 promoter       xln1 signal sequence 3'-primer (30-mer) [SEQ ID No.:14:]:

5'-CAG GCT CGA GGC CTG TGG GCA TCG CCA GAG
       ‾‾‾‾‾‾‾‾
         XhoI
       xln1 sequence Plasmid pALK572 containing the xln1 gene was used as a template for the PCR reaction. The reaction and purification of the product were done like in constructing pALK174. To obtain pALK805, the purified and SacII-XhoI digested PCR fragment was ligated to the SacII-XhoI cut plasmid pALK486 containing the cbh1 promoter. To construct pALK806, the xln1 sequence downstream from the XhoI site was isolated from the plasmid pALK572 by PstI (filled by T4 DNA polymerase)-XhoI digestion and the fragment was ligated to the BamHI (filled in with Klenow)-XhoI digested pALK805. pALK805 was obtained by ligating the EcoRI-SpeI fragment (filled in by Klenow) from pALK424, containing the amdS gene and the cbh1 3'-flanking region (as in pALK174), into the EcoRV cut pALK806.

*T. reesei* strain ALK02221 was transformed with the 8.2 kb NotI fragment from the plasmid pALK807.

Production of xylanase by the pALK807 transformants

Total of 51 pALK807 transformants were purified, analyzed and grown as in Example 2. Targeting efficiency to the cbh1 locus was 35%. The xylanase activity was measured as in Example 2, but at the pH 4.3 which is at the optimum pH range for the XYLI activity (Tenkanen et al., *Enzyme Microb. Technol.* 14:566–574 (1992)). The results, as an increase in xylanase activity produced compared to that of the host strain ALK02221 are shown in the Table 3. Thirty best xylanase producers obtained are included. One bottle of each transformant was grown.

The best transformants produced over 10 fold the amount of xylanase activity compared to the parent. Differing from the XYLII (pALK174) transformants, the best xylanase producers were CBHI[+].

TABLE 3

| transformant number | CBHI+/− (dot blot) | X compared to ALKO2221 |
|---|---|---|
| (control) ALKO2221 | (+) | |
| 20 | (+) | 11.8 |
| 5 | (+) | 11.7 |
| 18 | (+) | 10.4 |
| 4 | (+) | 9.8 |
| 33 | (+) | 9.5 |
| 32 | (−) | 9.2 |
| 21 | (+) | 8.9 |
| 3 | (+) | 8.9 |
| 46 | (+) | 8.8 |
| 40 | (+) | 8.2 |
| 1 | (+) | 8.2 |
| 43 | (+) | 8.0 |
| 10 | (+) | 8.0 |
| 19 | (+) | 8.0 |
| 8 | (+) | 7.9 |
| 51 | (+) | 7.8 |
| 39 | (+) | 7.6 |
| 12 | (−) | 7.5 |
| 7 | (−) | 7.2 |
| 36 | (+) | 6.9 |
| 41 | (−) | 6.8 |
| 35 | (+) | 6.8 |
| 49 | (−) | 6.6 |
| 29 | (−) | 6.6 |
| 24 | (+) | 6.3 |
| 50 | (−) | 5.9 |
| 14 | (−) | 5.9 |
| 26 | (+) | 5.8 |
| 15 | (−) | 5.8 |
| 52 | (+) | 5.1 |

EXAMPLE 5

A. Inactivation of the Major Cellulase cbh1 Gene

The cbh1 gene which encodes the major cellulase in *T. reesei* was inactivated by homologous recombination with plasmid pMS4 containing a 0.8 kb internal fragment of the cbh1 cDNA bearing a frame shift mutation. The pMS4 plasmid was prepared on the following way: the plasmid pTTc01 (Teeri et al., *Anal. Biochem.* 164:60–67 (1987); Penttilä et al., *Gene* 63:103–112 (1988)), which contains the full length cDNA clone of the cbh1 gene in the pUC8 vector (Vieira and Messing, *Gene* 19:259–268 (1982)), was digested with BglI cutting in the signal sequence (Shoemaker et al., *Bio/Technology* 1:691–696 (1983)) and with BglII. The resulting 0.8 kb DNA fragment bearing the 5' region of the cbh1 cDNA was made blunt-ended with $S_1$ nuclease and was ligated to an EcoRI cut, blunt-ended pUC18 vector (Yanish-Perron et al., *Gene* 33:103–119 (1985)). The clone obtained was cut in the middle of the cbh1 fragment with EcoRI. TheEcoRI generated termini were then filled in and back-ligated. The resulting plasmid pMS4 thus contains a frameshift mutation in the middle of the truncated cbh1 cDNA fragment.

*T. reesei* VTT-D-79125 (Bailey and Nevalainen, *Enzyme Microb. Technol.* 3:153–157 (1981)) was cotransformed with pMS4 and p3SR2. p3SR2 carries a 5 kb DNA fragment containing the *A. nidulans* amdS gene cloned into pBR322 (Kelly and Hynes, EMBO J. 4:475–479 (1985)). Transformants were selected on the basis of the AmdS$^+$ phenotype after which they were purified from conidia. About 600 clones from 200 independent transformants were then grown on microtiter plates and their cellulase phenotype was tested by the Ouchterlony immunodiffusion (Ouchterlony, *Progr. Allergy* 5:1–78 (1958)) using undiluted growth medium and the CBHI specific sheep antiserum.

Figure 12A:
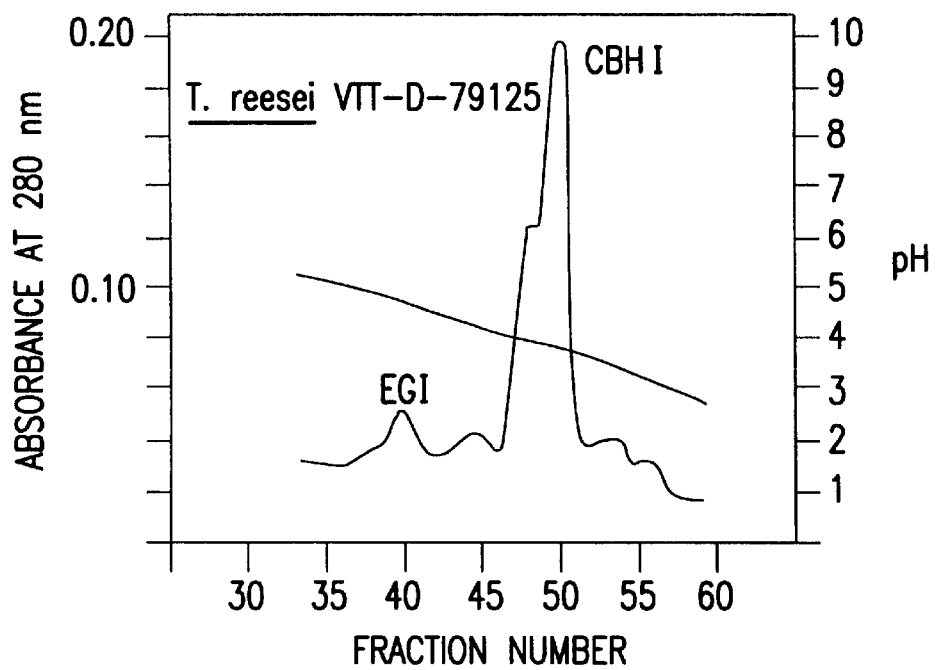
FIG. 12A shows an FPLC analysis of the CBHI negative transformant VTT-D-87312.
Figure 12B:
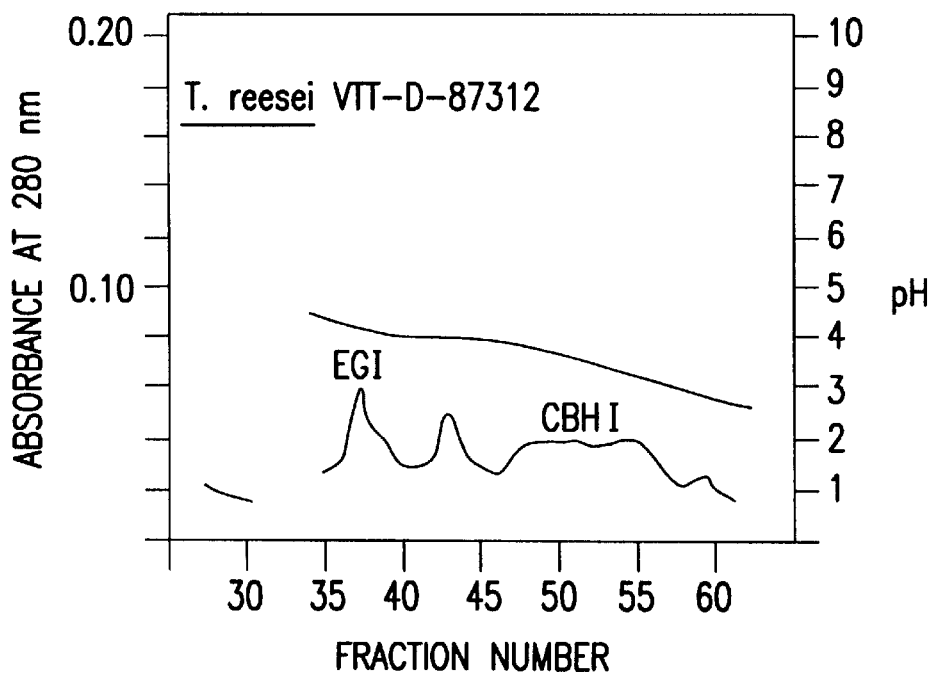
FIG. 12B shows its comparison to the untransformed host.

A number of strains produced no detectable CBHI. The CBHI negative character of one of these strains VTT-D-87312 was confirmed by analyzing the growth medium in SDS-PAGE and in FPLC, in which no peak corresponding to CBHI was seen (compare FIG. 12A and FIG. 12B). The amount of total secreted protein of the CBHI negative strain was about half of that secreted by the *T. reesei* VTT-D-79125. The filter paper degrading activity, FPU (Mandels et al., "Measurement of Saccharifying Cellulase," in: *Biotechnol. Bioeng. Symp.* no. 6., p. 21–33, Gaden, E. L., Mandels, M. H., Reese, E. T., and Spano, L. A. (eds.), John Wiley and Sons, New York, 1976) activity detected in the culture supernatant fraction of the strain VTT-D-87312 was significantly reduced and was about 20% of normal. The lack of the major cellobiohydrolase which normally represents about 60% of the total secreted protein did not notably change the growth properties of the strain.

B. Deletion of the cbh2 Gene with Its Promoter

Figure 13:
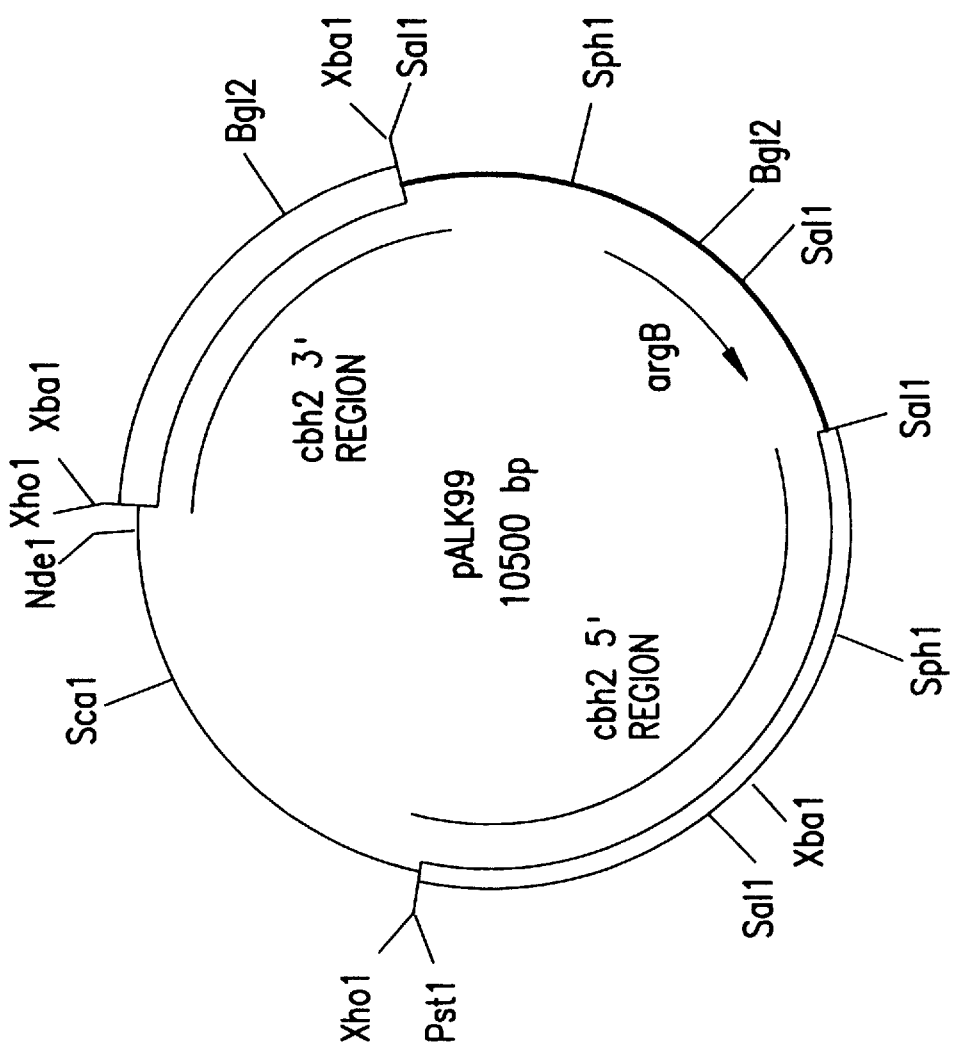
FIG. 13 shows a diagram of the plasmid pALK99.
Figure 14:
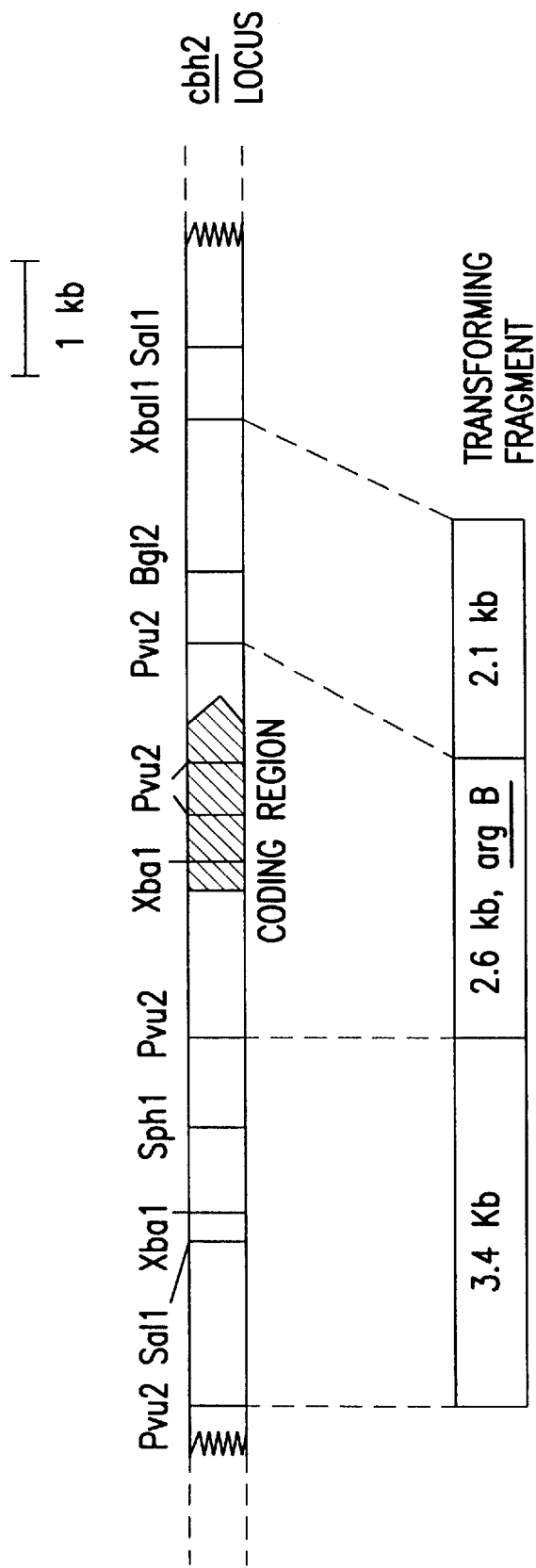
FIG. 14 shows a diagram of the replacement of the chromosomal cbh2 gene with the argB gene.

The cbh2 gene of Trichoderma was replaced with the Aspergillus argB gene as described below. Plasmid pALK99 was constructed to be the source of the transforming fragment (FIG. 13). Plasmid pALK99 was constructed in the following way. The PvuII fragment (containing the multilinker) of the plasmid pUC19 was replaced by a new synthetic multilinker fragment containing recognition sites for the following restriction enzymes: XhoI-StuI-SmaI-XbaI-PvuII-SalI-XhoI. The new plasmid was called pALK96. This plasmid was cut with XbaI and PvuII and a 2.1 kb XbaI-PvuII fragment from the 3' region of the cbh2 gene (see FIG. 14) was ligated into it. The resulting plasmid was cut with PvuII and HincII and ligated with the 3.4 kb PvuII-fragment from the 5' area of the cbh2-gene (see FIG. 14). Both the 3' and 5' fragments were originally from the λ clone cbh2lambdal (Teeri et al., *Gene* 51:43–52 (1987)). The resulting plasmid was called pALK98. The *Aspergillus nidulans* argB gene (2.6 kb SalI fragment) was then ligated between the 3' and 5' regions of the cbh2 gene into the unique PvuII site of plasmid pALK98. The resulting plasmid was called pALK99. Thus, the transforming fragment which is isolated from pALK99 as a XhoI fragment contains the Aspergillus argB gene as a 2.6 kb SalI fragment (Berse et al., *Gene* 25:109–117 (1983)) between 3.4 kb (PvuII-PvuII fragment) of the 5' flanking region and 2.1 kb (PvuII-XbaI fragment) of the 3' flanking region of the cbh2 gene (see FIG. 14). *T. reesei* VTT-D-87305 ArgB$^-$ mutant strain (Penttila et al., 1987, Gene 61:155–164) was transformed with this fragment using selection for arginine prototropy. ArgB$^+$ transformants were then screened for CBHII$^-$ phenotype by WesteTn blotting using monoclonal antibody against CBHII. Replacement of the cbh2 locus by the transforming fragment in the CBHII$^-$ transformants was then confirmed by Southern blots. Strain ALKO 2564 is an example of this kind of "replacement" strain and thus does not contain the cbh2 gene any more.

With the method described above, the cbh2 gene of Trichoderma was replaced with the Aspergillus trpC gene.

The *Aspergillus nidulans* trpC gene (4.2 kb XhoI fragment blunt-ended with Klenow enzyme) was ligated between the 3' and 5' regions of the cbh2 gene into the unique PvuII site of the plasmid pALK98. The resulting plasmid was called pALK402. The transforming fragment which is isolated from pALK402 as XhoI fragment contains *A. nidulans* trpC gene as a 4.2 kb XhoI fragment (Yelton et al., PNAS, 91:1470–1474 (1984)) between the 3.4 kb of the 5' flanking region and 2.1 kb of the 3' flanking region of the cbh2 gene. T. reesei ALK02319 trpC⁻ mutant strain was transformed with this fragment using selection for tryptophane prototrophy. TrpC⁺ transformants were screened for CBHII⁻ phenotype by Western blotting using monoclonal antibody against CBHII. Replacement of the cbh2 locus by the transforming fragment in the CBHII⁻ transformants was confirmed by Southern blots. Strain ALK02721 is an example of this kind of "replacement" strain and thus does not contain the cbh2 gene any more.

EXAMPLE 6

Construction of a CBHI Negative Trichoderma Strain Producing Elevated Amounts of EGI The CBHI negative strain VTT-D-87312 described in Example 5 was transformed with the plasmid pAMH 111 to enhance EGI expression in a CBHI negative background. The plasmid pAMH 111 was constructed using the general expression vector pAMH 110 (both of these plasmids are described in EP 244,234). pAMH 110 was built from pUC19 (Yanish Perron et al., Gene 33:103–119 (1985)). First the single NdeI site of pUC19 was destroyed by filling in the recessed ends with Klenow polymerase, and then the plasmid was digested with EcoRI and PstI and ligated to cbh1 promoter and terminator fragments to make an expression cassette. The promoter fragment was a 2.6 kb EcoRI-PstI fragment from the plasmid pAMH 102 (Harkki et al., Bio/Technology 7:596–603 (1989)). The terminator was a 0.75 kb AvaII fragment contained in a PstI fragment which also included an adaptor with the TAA stop codon in all three reading frames. pAMH 110 was then digested with SacII and NdeI to remove a piece of DNA between the cbh1 promoter and terminator, and the digested ends were made blunt-ended with $S_1$ nuclease and Klenow polymerase. The egl1 cDNA to be expressed was taken from the plasmid pTTc11 ((Teeri et al., Anal. Biochem. 164:60–67 (1987); Penttilä et al., Yeast 3:175–185 (1987); as a 1.6 kb EcoRI-BamHI fragment, made blunt-ended with Klenow polymerase, and ligated into the expression cassette to give plasmid pAMH 111. Transformation was carried out as a cotransformation with pAMH 111 and the plasmid pAN8-1 (Mattern et. al., "Transformations of Aspergillus oryzae," In: Abstracts of the 19th Lunteren Lectures of Molecular Genetics of Yeasts and Filamentous Fungi and its Impact on Biotechnology, Lunteren, the Netherlands, p.34, (1987)) carrying the phleomycin resistance gene of Steptoallotheicus hindustanus under the A. nidulans gpd promoter. Another marker must be used if, as in this example, the strain VTT-D-87312 was already AmdS⁺. Transformants were purified and tested for endoglucanase production in shake flasks cultures. In about 20% of the transformants, the level of hydroxyethylcellulose (HEC) hydrolyzing activity was higher than in the recipient strain. The amount of EGI protein (Table 4) in the shake culture supernatant fraction was analyzed from three transformants showing high HEC activity. Southern blot analysis of these transformants showed that in the best endoglucanase producing clone (ALKO 2466) the expression cassette containing the egl1 cDNA between the cbh1 promoter and terminator sequences was integrated in the chromosomal cbh1 locus through the terminator sequences on the insert.

The amount of secreted EGI protein in this transformant strain (ALKO 2466) was increased about four fold over that of the control (Table 4).

TABLE 4

Characterization of EGI production in T. reesei VTT-D-87312 (CBHI negative transformant of VTT-D-79125) and in ALKO 2493, ALKO 2466 and ALKO 2494 which arise from VTT-D-87312 transformed with the plasmid pAMH111. TT-D-79125 is the untransformed high-cellulose producing T. reesei mutant strain. All strains were grown in shake flasks as described in the Materials and Methods. The amount of EGI protein and total secreted protein were measured after 7 days cultivation as described in the Materials and Methods.

|  | EG1 protein (mg/ml) | Total secreted protein (mg/ml) | % EGI % of the total secreted protein |
|---|---|---|---|
| VTT-D-87312 | 0.35 | 4.5 | 7.7 |
| ALKO 2493 | 1.25 | 5.2 | 24.0 |
| ALKO 2466 | 1.90 | 5.8 | 32.8 |
| ALKO 2494 | 1.40 | 5.9 | 23.7 |
| VTT-D-79125 | 0.75 | 10.6 | 7.1 |

EXAMPLE 7

Figure 15:
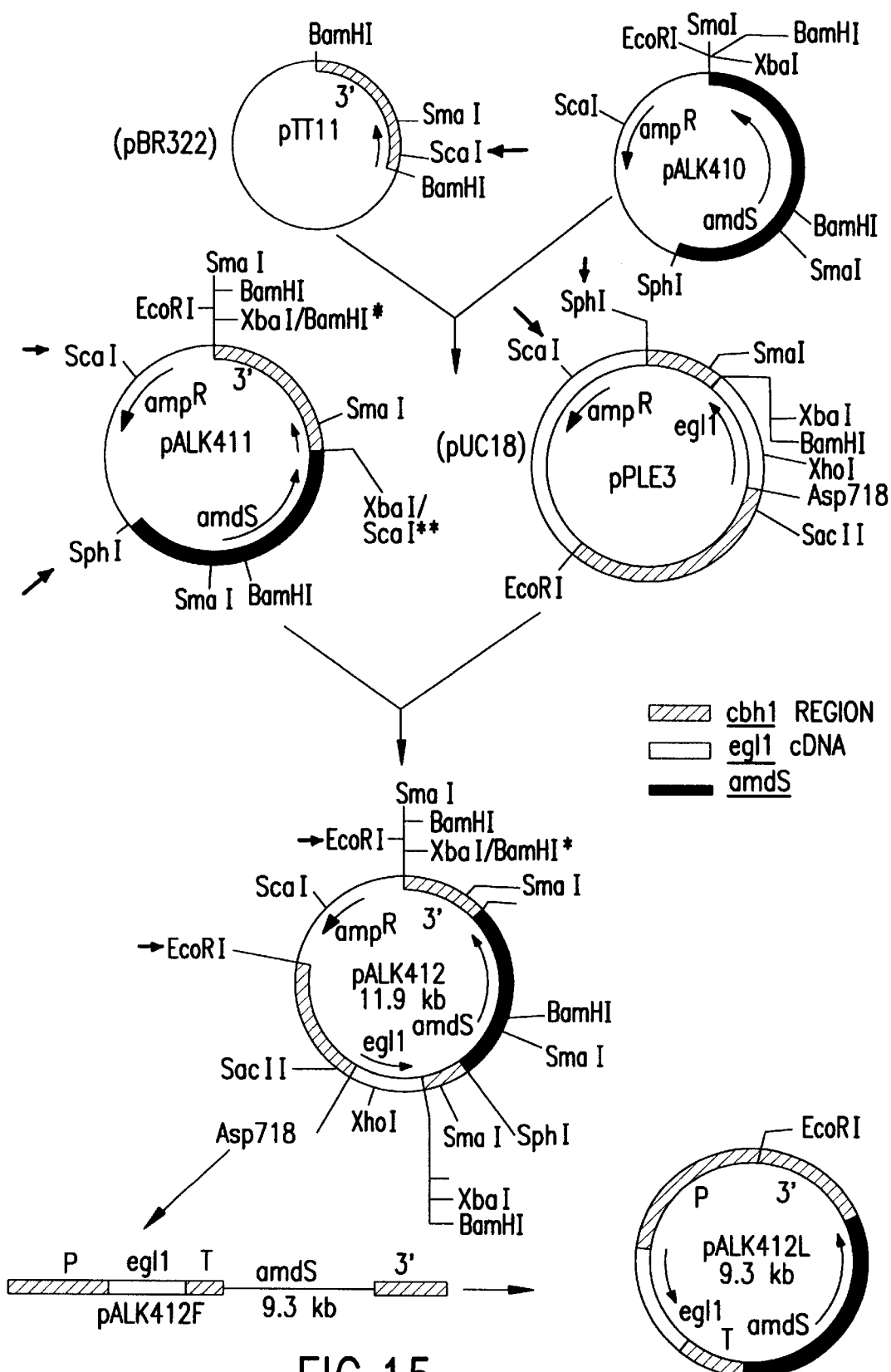
FIG. 15 shows the construction of the plasmid pALK412. An asterisk next to the restriction site means this/these enzymes no longer recognize that site.

Simultaneous Inactivation of the cbh1 Gene and Multiplication of the egl1 Copy Number The cbh1 gene of T. reesei VTT-D-79125 was replaced with the Trichoderma egl1 cDNA and amdS gene. The egl1 cDNA was ligated between the promoter and terminator of cbh1 gene. Plasmid pALK412 was constructed to be the source of the transforming fragment. The plasmid pALK412 was prepared as in FIG. 15.

The plasmid p3SR2 which contains the Aspergillus nidulans amdS gene cloned into pBR322 (Kelly and Hynes, EMBO J. 4:475–479 (1985)) was digested with SphI and with XbaI. The resulting 3.2 kb DNA fragment bearing the whole amdS gene was ligated to the SphI and XbaI cut pUC19 vector (Yanisch-Perron et al., Gene 33:103–119 (1985)). The resulting plasmid was called pALK410.

A DNA fragment containing 1.65 kb of the 3' region of the cbh1 gene starting from the ScaI site in the coding region was isolated as a ScaI-BamHI fragment and blunt-ended with Klenow-enzyme. This fragment was ligated to the XbaI site (blunt-ended with Klenow enzyme) of the plasmid pALK410. In this case the 3' fragment was isolated from the plasmid pTT11.

Plasmid pTT11 (Teeri et al., Bio/Tech 1:696–699 (1983)) contains 1.8 kb fragment of the cbh1 region, 3' from the BamHI site in the coding region, cloned into the BamHI site of pBR322. The gene can also be isolated from other sources, for example, from a X clone 44A (Teeri et al., Bio/Tech 1:696–699).

Figure 16:
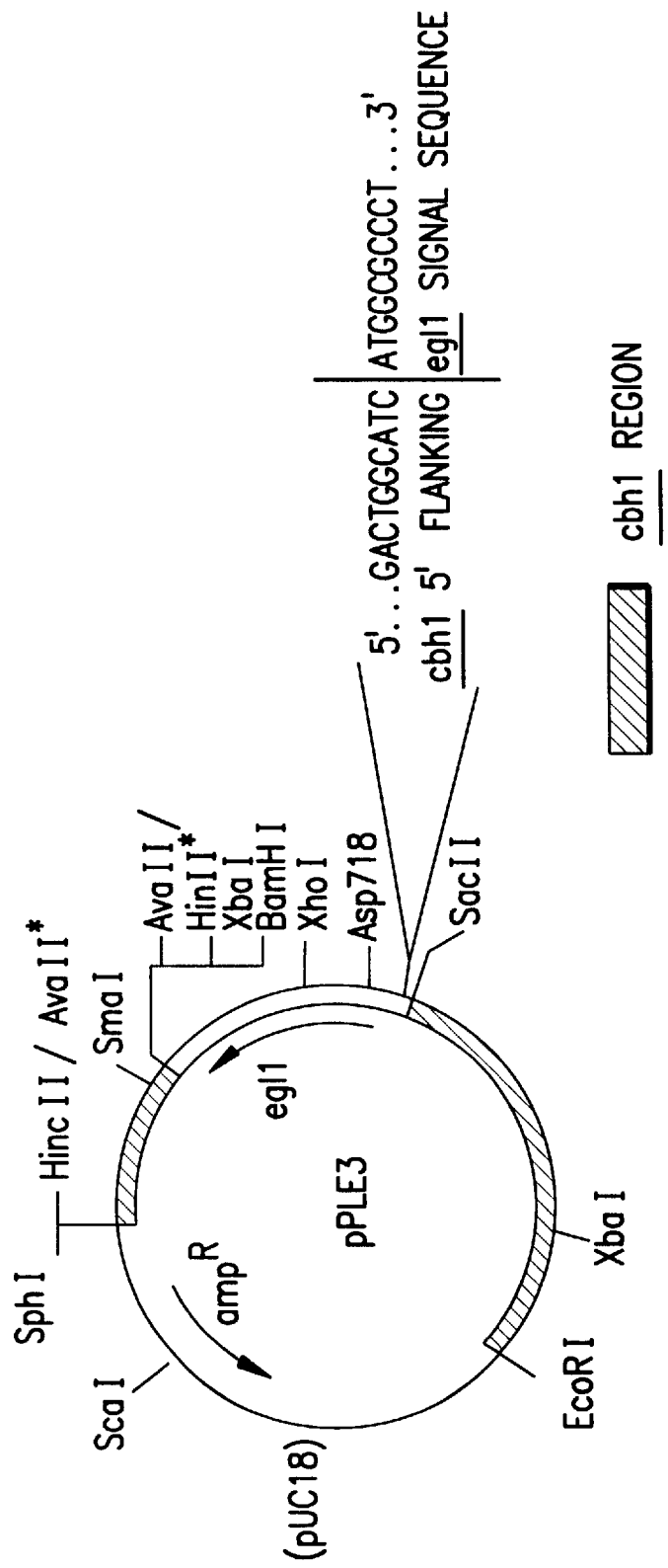
FIG. 16 shows a diagram of plasmid pPLE3.

The plasmid obtained was pALK411. It was digested with ScaI and with SphI. The 5.8 kb fragment was ligated to ScaI and SphI cut plasmid pPLE3 (Nevalainen, et al., In: Molecular Industrial Mycology: Systems and Applications for Filamentous Fungi, Leong et al., eds., pp. 129–148 (1990)) which contains egl1 cDNA between the promoter and terminator regions of cbh1 gene cloned into pUC18 (FIG. 16). The promoter and terminator regions are from the expression vector pAMH110 (Nevalainen et al., In: Molecular Industrial Mycology: Systems and Applications for Filamentous Fungi, Leong et al., eds., pp. 129–148 (1990)).

The resulting plasmid pALK412 was cut with EcoRI to remove the bacterial DNA. The 9.3 kb pALK412F fragment was also backligated to form plasmid pALK412L.

*T. reesei* VTT-D-79125 (Bailey and Nevalainen, *Enzyme Microb. Technol.* 3:153–157 (1981)) was transformed with plasmid pALK412, with pALK412F linear fragment, with backligated pALK412L and with pALK412F and pALK412L at the same time with a molar ratio of 5:1 respectively. Transformants were selected on the basis of the amdS+ phenotype and purified from conidia on selective medium containing acetamide as a sole nitrogen source.

Purified transformants were grown on microtiter plates and were screened for CBHI− phenotype by Western blotting using polyclonal antibody against CBHI protein. About one third of the pALK412F transformants produced no detectable CBHI. There was one CBHI− transformant among forty strains that had been transformed with the plasmid pALK412.

CBHI− transformants were tested for endoglucanase production in shake flasks cultures. In all of these transformants the level of hydroxyethylcellulose (HEC) hydrolyzing activity was higher than in the recipient strain. The best transformants secreted 4–5 times the endoglucanase activity of the recipient strain.

Southern blot analysis of the CBHI− transformants showed that their cbh1 locus was replaced by the vector fragment. The chromosomal DNA of the transformants was digested with XhoI and hybridized with the 0.5 kb fragment of the cbh1 coding region probe.

The best endoglucanase producing strains had more than one copy of the vector fragment which carries the gene of interest inserted into the Trichoderma genome.

EXAMPLE 8

Construction of a cellobiohydrolase negative *T. reesei* strain

The hypercellulolytic mutant VTT-D-79125 (Bailey, M. J. et al., *Enzyme Microb. Technol.* 3:153–157 (1982)) is a good cellulase producer, and also, has a markedly better viability and increased capability to produce secreted protein as a result of the mutagenesis program that created it. Thus, we wanted to make use of the high protein production capacity of this mutant to produce xylanases free of cellobiohydrolases to be used in pulp bleaching.

Figure 17:
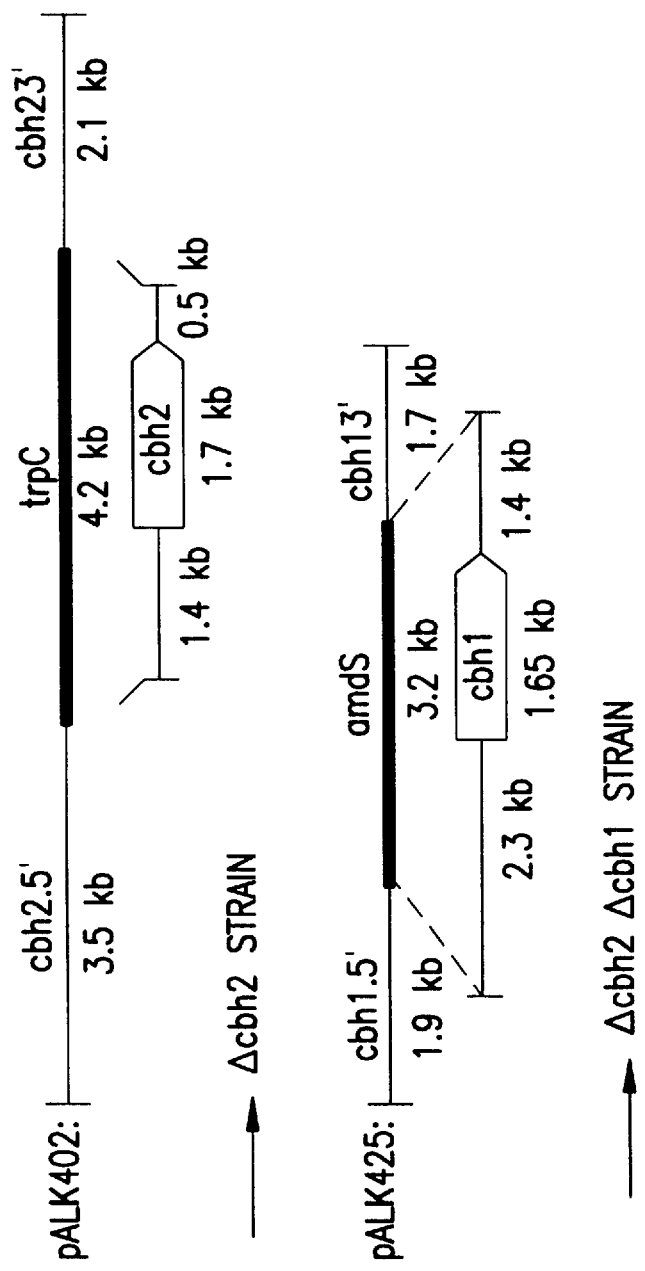
FIG. 17 shows the construction of a Δcbh1 Δcbh2 strain; tipC-mutant of VTT-D-79125 (UV).

An UV-induced tryptophan auxotrophic mutant of VTT-D-79125 was transformed with a linear fragment of DNA (FIG. 17), on which the cbh2 flanking regions were used to target the transforming fragment into the cbh2 locus. Purified TrpC+ transformants were grown on microtiter plates and were screened for CBHII− phenotype by Western blotting using monoclonal antibody against CBHII. Replacement of the cbh2 locus by the transforming fragment was confirmed by Southern blotting. One such cbh2 negative transformant was transformed with a second DNA fragment. This time cbh1 flanking regions were used in order to replace the wild type cbh1 locus with the amdS marker for acetamidase. Purified amdS+ transformants were grown on microtiter plates and screened for CBHI− phenotype by Western blotting using polyclonal antibody against CBHI protein. The replacement was again confirmed by Southern blotting. The resulting strain has neither the cbh1 nor the cbh2 gene and thus is unable to produce cellobiohydrolases in any conditions.

Figure 18:
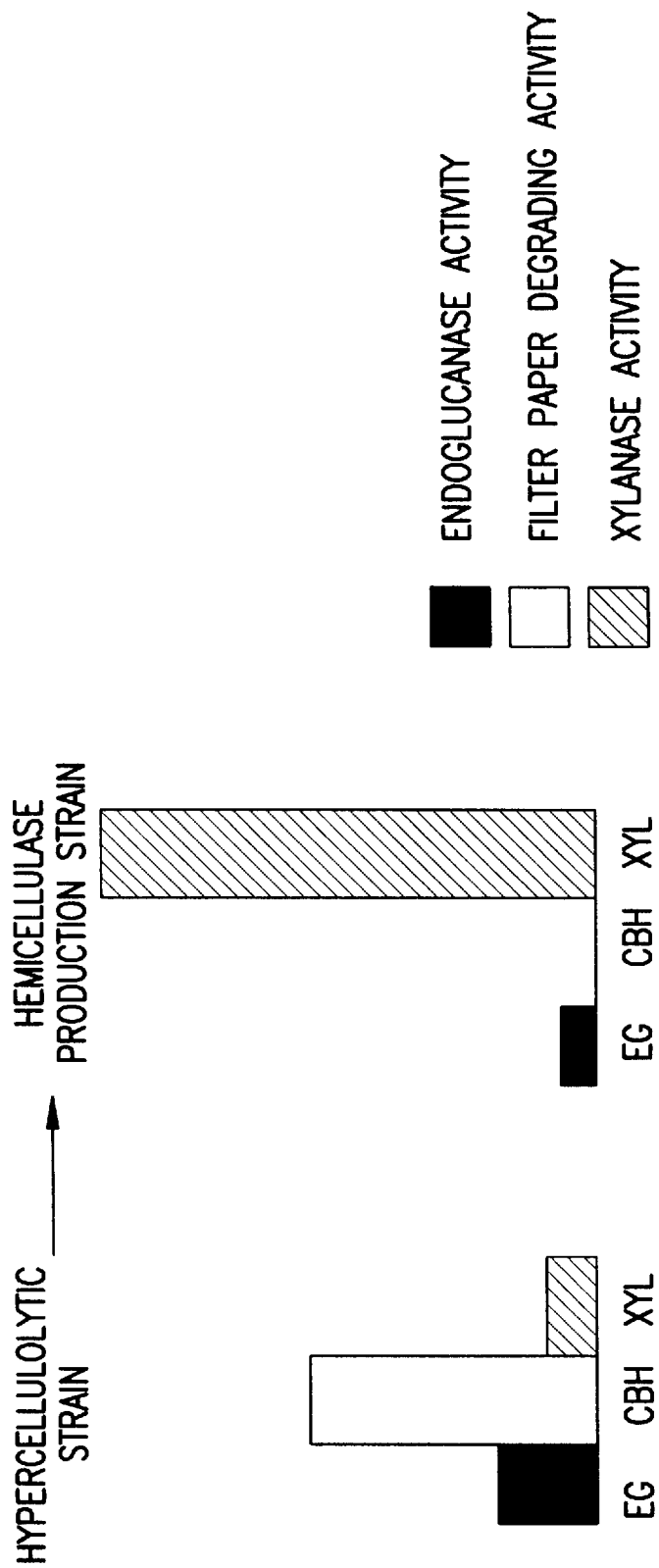
FIG. 18 shows the enzyme profiles of the hypercellulolytic mutant strain of *T. reesei* VTT-D-79125 (UV) and the genetically engineered derivative of that strain that lacks cellobiohydrolase.

FIG. 18 illustrates the enzyme production profiles of the hypercellulolytic strain and its cellobiohydrolase negative derivative. Production of endoglucanases is lowered by choosing suitable fermentation conditions as well known in the art. With the new strain xylanase can be produced as an enzyme composition secreted from the host cell, such enzyme composition not containing cellobiohydrolases, and thus lacking activity against crystalline cellulose. The very small amount of endoglucanase activity still present does not have any harmful effects on the pulp properties when this kind of preparation is used in enzyme aided pulp bleaching.

EXAMPLE 9

Construction of Strains Producing Different Combinations of Cellulases

Using similar gene replacement strategy as in the previous strain constructions (FIG. 17), sets of *T. reesei* strains have been constructed that produce different combinations of cellulases (Table 5). In the first set, strains A–D, one cellulase is eliminated at a time. Strains A–D synthesize everything the parent strain does except for CBHI (strain A), CBHII (strain B), EGI (strain C) or EGII (strain D). The second set, strains E–J, provides mutants missing all pairs of the four cellulases. Strain E lacks CBHI and CBHII. Strain F lacks CBHI and EGI. Strain G lacks CBHI and EGII. Strain H lacks CBHII and EGI. Strain I lacks CBHII and EGII. Strain J lacks EGI and EGII.

When genes for both EGI and EGII (strain J, Table 5) are deleted, the activity against hydroxyethylcellulose drops to less than 10% of the activity produced by the parent hypercellulolytic strain, VTT-D-79125. Lack of CBHI or CBHII proteins (strain E, Table 5) can be assayed by examining for activity against filter paper as known in the art. When both CBHI and CBHII are eliminated, no measurable activity is produced. One of skill in the art would recognize that further modifications, such as to eliminate three or more activities may also be constructed by the same strategy.

TABLE 5

| Strain type | CBHI | CBHII | EGI | EGII |
|---|---|---|---|---|
| \multicolumn{5}{c}{Genetically Engineered Strains to Produce Novel Cellulase Mixtures} | | | | |
| A | − | + | + | + |
| B | + | − | + | + |
| C | + | + | − | + |
| D | + | + | + | − |
| E | − | − | + | + |
| F | − | + | − | + |
| G | − | + | + | − |
| H | + | − | − | + |
| I | + | − | + | − |
| J | + | + | − | − |
| K | + | − | − | − |
| L | − | − | + | − |

Figure 19:
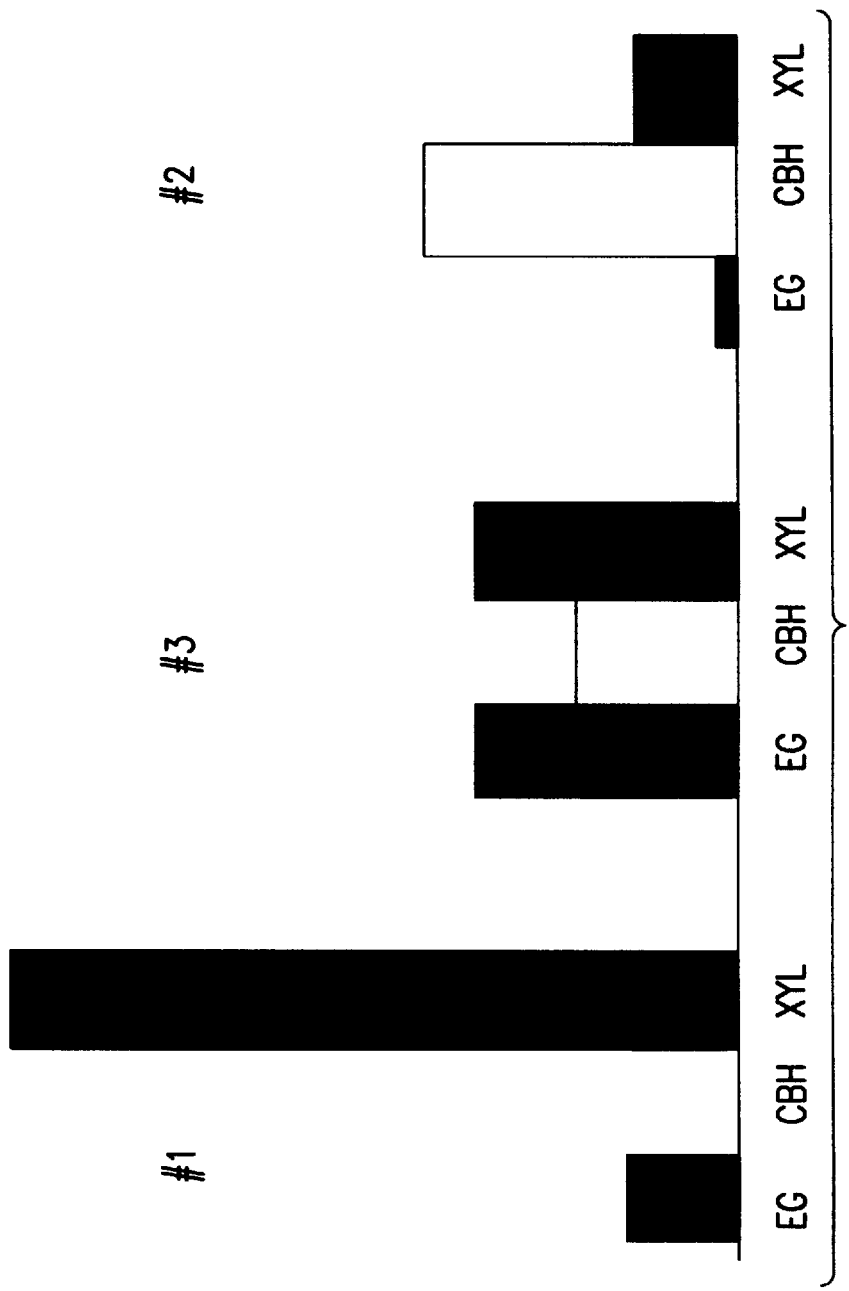
FIG. 19 shows modified enzyme profiles of the genetically engineered *T. reesei* strains #1, #2 and #3.

FIG. 19 illustrates the powerfulness of gene technology to produce the compositions of the invention. Genetic engineering has been successfully used to construct derivatives of the hypercellulolytic mutant to produce different cellulase-xylanase mixtures. In strain 3, the cbh1 gene coding sequence is replaced with the egl1 gene coding sequence, which in strain 3 is expressed under the cbh1 promoter. Thus, the proportion of endoglucanases produced and secreted by these hosts is increased.

Strain 1 produces xylanases as the main activity, and in different production conditions, as known in the art, endoglucanases without any cellobiohydrolases can be produced. In the enzyme mixture produced by strain 3, the proportion of endoglucanases is increased, and strain 2 produces cellobiohydrolases essentially free of endoglucanases.

EXAMPLE 10

Use of the Enzyme Preparations in Biobleaching

It is known that treatment of cooked (kraft) pulp with xylanase improves its bleachability. Xylanase enzyme preparations that are going to be used to treat pulp must not contain activities that would attack cellulose because such activities would weaken the strength properties of the pulp.

The previous bleaching experiments had been performed with xylanase preparations that had been produced by deletion strains of Trichoderma (strains having one or two cellulase genes deleted). The treated pulps had been conventionally cooked pulps (kappa number 31-32) without oxygen-delignification. The bleaching after enzyme treatment contained both elemental chlorine and chlorine dioxide.

In this experiment however, several different parameters were tested. First, the biobleaching effects of an enzyme preparations produced by a Trichoderma overproducer of xylanase (in which one cellulase gene was also deleted, $xyl2^+$, $cbh1^-$) was compared with the effects of an enzyme preparation produced by a cellulase deletion strain of Trichoderma ($cbh1^-cbh2^-$), especially regarding whether the same effect in bleachability was obtained using the same xylanase activity from both preparations.

The xylanase/cellulase ratio is larger in xylanase overproducers than it is in mere deletion strains. This means that when a constant dose of xylanase is used, the overproducer enzyme contains less cellulase side activities. Thus, the strength properties should be better.

It was also desired to test a type of pulp that is becoming more and more common, oxygen-delignified pulp. In addition, since many mills in this industry desire to omit elemental chlorine from their bleaching sequence (because of environmental reasons), a bleaching sequence was chosen that did not contain any elemental chlorine.

The pH optimum of the xylanase activities in the two enzyme preparations, A (produced from a xylanase II overproducer ($xyl2^+$, $cbh1^-$)) and B (produced from a deletion strain $cbh1^-cbh2^-$) was determined to be 4.5 and 5.5, respectively. However, as used here, it is better to operate at a higher pulp pH because it means that less acid is necessary to adjust the pulp pH. Pulp pH 6 was chosen on the basis of preliminary experiments on the relative activities of these enzyme preparations at different pH values and on the basis of the reducing the acid need.

Oxygen-delignified softwood kraft mill pulp (kappa 16.1, brightness 35.4% ISO) was used. The pulp pH was adjusted with sulphuric acid to 6. The pulp samples of 250 g dry matter were treated with enzyme "enzyme A"-(xylanase overproducer ($XYLII^+CBH1^-$)) or "enzyme B" (deletion strain $CBHI^- CBHII^-$)) so that the xylanase dosage was 100 nkat/g pulp dry matter, at pH 6 for 55° C. for 2 hours and washed. Then they were bleached using a typical ECF (elemental chlorine free) bleaching sequence $D_0$ (EO) DED. Reference pulp was bleached without enzyme treatment.

The following standard methods were used: brightness (ISO 2470), kappa number (ISO 302), viscosity (ISO 5351/1) and pc (post-coloring) number (TAPPI 260 pm-81). Pulps were beaten with a PFI mill (ISO 5264/2), handsheets were made according ISO 5269/1 and the strength properties were tested (ISO 5270).

The enzyme treated pulps were bleached using 25% lower $ClO_2$ dosage in the first bleaching stage than in the reference pulp. Enzyme pretreated pulp achieved the full brightness with about 15% less aCl in total (Table 6). This is about the same as we achieved in earlier experiments using deletion strains and conventionally cooked pulps (kappa number 31–32) without oxygen-delignification and bleaching sequences containing elementary chlorine (Lahtinen, T., et al., In: *Biotechnology in Pulp and Paper Industry*, Kuwahara, M., Shimada, M. (eds.), Uni Publishers Co., Tokyo, Japan, pp. 129–137 (1992)). Therefore, the same effect on the improvement of the bleachability could be achieved.

The strength properties (viscosity and tear index) correlated with the cellulolytic side activities: with low side activities of the overproducer, enzyme A, strength properties similar to the reference were obtained. Table 6 shows the viscosity and tear results. However, with the deletion strain B, these values were lower, indicating a weaker fiber quality.

Optical properties were also comparable to reference, with the exception of the pc-number (the measure of brightness reversion) which was even better in enzyme treated pulps.

TABLE 6

ECF Bleaching Experiments

| | Enzyme | | |
|---|---|---|---|
| | A | B | Reference |
| Total | | | |
| Consumption of $ClO_2$, act. Cl kg/t | 47.7 | 47.4 | 54.9 |
| Consumption of $ClO_2$, act. Cl kg/t, at ISO 90%[1] | 46.9 | 49.4 | 56.1 |
| Reduction | 16% | 12% | — |
| Final | | | |
| Brightn, % ISO | 90.2 | 89.5 | 89.7 |
| pc number | 0.45 | 0.54 | 0.87 |
| Viscosity | 830 | 810 | 840 |
| Pulp properties after refining (at Tensile Index 70 Nm/g) | | | |
| PFI revs | 1123 | 945 | 871 |
| Tear, $mNm^2/g$ | 13.8 | 12.2 | 14.2 |
| Light scatt. coeff. $m^2/kg$ | 20.7 | 20.6 | 21.6 |
| Light abs. coeff. $m^2/kg$ | 0.06 | 0.08 | 0.06 |
| Fiber length | | | |
| mm | 2.00 | 1.99 | 1.97 |
| <0.20 mm, % | 3.23 | 3.22 | 3.39 |

[1]assuming that 4 kg aCl increases brightness by 1 ISO unit

Bleaching Conditions:

| Stage | D0 | (E0) | D1 | E | D2 |
|---|---|---|---|---|---|
| Consistency, % | 3 | 10 | 9 | 9 | 9 |
| Temperature, °C. | 55 | 75 | 70 | 70 | 70 |
| Time, min. | 60 | 60 | 180 | 60 | 180 |
| End pH | 2.9–3.2 | 10.8 | 3.7–4.0 | 10.8 | 3.5–3.8 |
| $ClO_2$ dose, kg/t active Cl | 24.2 | — | 17 | — | 8 |
| $O_2$ pressure, bar | — | 2 | — | — | — |
| NaOH dose, kg/t | — | 17 | 2.5 | 9 | — |

Having now fully described the invention, it will be understood by those with skill in the art that the scope may be performed within a wide and equivalent range of conditions, parameters and the like, without affecting the spirit or scope of the invention or any embodiment thereof. All references cited herein are fully incorporated herein by reference.

What is claimed is:

1. An isolated nucleic acid molecule comprising a nucleic acid sequence encoding the amino acid sequence of the *T. reesei* pI 5.5 xylanase shown in SEQ ID No. 4.

2. The isolated nucleic acid molecule of claim 1, wherein said nucleic acid sequence is that of the DNA sequence of SEQ ID No. 3.

3. An isolated nucleic acid molecule comprising a nucleic acid sequence encoding the amino acid sequence of the *T. reesei* pI 9 xylanase shown in SEQ ID No. 2.

4. The isolated nucleic acid molecule of claim 3, wherein said nucleic acid sequence is that of SEQ ID 1.

5. An isolated nucleic acid molecule, comprising a nucleic acid sequence encoding the amino acid prosequence of *T. reesei* pI 5.5 xylanase of SEQ ID NO:4, said prosequence lacking the signal sequence of SEQ ID. No. 4.

6. The isolated nucleic acid molecule of claim 5, wherein said nucleic acid sequence is SEQ ID No.3 lacking that part of the sequence encoding the signal sequence.

7. An isolated nucleic acid molecule, comprising a nucleic acid sequence encoding the amino acid presequence of *T. reesei* pI 9.0 xylanase of SEQ ID NO:2, said proseqence lacking the signal sequence of SEQ ID, No.2.

8. The isolated nucleic acid molecule of claim 7, wherein said nucleic acid sequence is SEQ ID No.1 lacking that part of the sequence encoding the signal sequence.

9. An isolated nucleic acid molecule, comprising a nucleic acid sequence encoding the amino acid sequence of the mature *T. reesei* pI 5.5 xylanase of SEQ ID No.4, said mature xylanase sequence lacking the preprosequence of SEQ ID. No. 4.

10. The isolated nucleic acid molecule of claim 9, wherein said nucleic acid sequence is the DNA sequence of SEQ ID No. 3 lacking that part of the sequence encoding the pre-prosequence.

11. An isolated nucleic acid molecule, comprising a nucleic acid sequence encoding the amino acid sequence of the mature *T. reesei* pI 9.0 xylanase of SEQ ID NO:2, said mature xylanase sequence lacking the preprosequence of SEQ ID. No.2.

12. The isolated nucleic acid molecule of claim 11, wherein said nucleic acid sequence is SEQ ID No.1 lacking that part of the sequence encoding the preprosequence.

13. An isolated nucleic acid molecule comprising a nucleic acid sequence encoding the amino acid sequence of the *T reesei* pI 5.5 xylanase shown in SEQ ID No. 4 or the *T. reesei* pI 9 xylanase shown in SEQ ID No. 2, wherein the homologous signal sequence is replaced with a heterologous sequence that allows secretion of the xylanase.

14. An isolated nucleic acid molecule consisting of nucleic acid sequence encoding the amino acid sequence of the *T. reesei* pI 5.5 xylanase signal sequence.

15. An isolated nucleic acid molecule consisting of nucleic acid sequence encoding the amino acid sequence of the *T. reesei* pI 9.0 xylanase signal sequence.

16. A recombinant vector comprising the isolated nucleic acid molecule of any one of claims 1–4 or 14–13.

17. The recombinant vector of claim 16, wherein said vector is selected from the group consisting of a plasmid and a linear DNA.

18. A recombinant host transformed with the recombinant vector of claim 16.

19. The recombinant host of claim 18, wherein said host belongs to the genus Trichoderma.

20. The recombinant host of claim 19, wherein said host is *T. reesei*.

21. A recombinant vector comprising the isolated nucleic acid molecule of any one of claims 1–4 or 14–13, wherein said nucleic acid sequence is operably linked to a *T. reesei* promoter selected from the group consisting of the xln1 promoter, the xln2 promoter, the cbh1 promoter, the cbh2 promoter, the egl1 promoter, and the egl2 promoter.

22. A recombinant host transformed with the recombinant vector of claim 21.

23. The recombinant host of claim 22, wherein said host belongs to the genus Trichoderma.

24. The recombinant host of claim 23, wherein said host is *T. reesei*.

25. A method for the production of an enzyme preparation enriched in xylanase activity, said method comprising:

(1) transforming a host cell with a recombinant construct encoding *T. reesei* xln1 and/or *T. reesei* xln2;

(2) culturing said host cell under conditions that express said xln1 and/or said xln2 from said host cell of step (1); and (3) collecting said culture medium.

26. The method of claim 25, wherein said host cell is genetically incapable of expressing one or more endogenous cellulolytic enzymes.

27. The method of claim 26, wherein said cellulolytic enzyme is selected from the group consisting of CBHI, CBHII, EGI and EGII.

28. The method of claim 27, wherein said cellulolytic enzyme is CBHI.

29. The method of any one of claims 25–28, wherein said host is Trichoderma.

30. The method of claim 29, wherein said Trichoderma is *T. reesei*.

31. An enzyme preparation obtained from culture medium after culture of a host transformed with a vector, said vector comprising a nucleic acid sequence encoding at least that portion of SEQ ID No. 4 that encodes the amino acid sequence of mature *T reesei* pI 5.5 xylanase and said culture medium containing the xylanase expression product encoded by said nucleic acid sequence.

32. An enzyme preparation obtained from culture medium after culture of a host transformed with a vector, said vector comprising a nucleic acid sequence encoding at least that portion of SEQ ID No. 2 that encodes the amino acid sequence of mature *T. reesei* pI 9.0 xylanase and said culture medium containing the xylanase expression product encoded by said nucleic acid sequence.

33. The enzyme preparation as in claim 31 or 32, wherein said vector is selected from the group consisting of a plasmid and a linear DNA.

34. The enzyme preparation of claim 33, wherein said host belongs to the genus Trichoderma.

35. The enzyme preparation of claim 34, wherein said host is *T reesei*.

36. The enzyme preparation of claim 33 wherein the host is a filamentous fungus other than *T. reesei*.

37. The enzyme preparation of claim 33 wherein the host is a yeast or bacterium.

* * * * *